(12) United States Patent
Laurent et al.

(10) Patent No.: US 11,033,263 B2
(45) Date of Patent: Jun. 15, 2021

(54) LOCKOUT ENGAGEMENT FEATURES FOR SURGICAL STAPLER

(71) Applicant: Ethicon LLC, Guaynabo, PR (US)

(72) Inventors: Ryan J. Laurent, Loveland, OH (US); Jason M. Rector, Maineville, OH (US); Robert J. Simms, Liberty Township, OH (US); Jeffrey C. Gagel, Loveland, OH (US); Nicholas Fanelli, Morrow, OH (US); Douglas B. Hoffman, Harrison, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 126 days.

(21) Appl. No.: 16/266,592

(22) Filed: Feb. 4, 2019

(65) Prior Publication Data
US 2019/0239873 A1 Aug. 8, 2019

Related U.S. Application Data

(63) Continuation of application No. 14/314,298, filed on Jun. 25, 2014, now Pat. No. 10,314,577.

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/07292* (2013.01);
(Continued)

(58) Field of Classification Search
CPC ............ A61B 17/068; A61B 17/07207; A61B 2090/0814
See application file for complete search history.

(56) References Cited

U.S. PATENT DOCUMENTS

| 4,805,823 A | 2/1989 | Rothfuss |
| 5,275,323 A | 1/1994 | Schulze et al. |
| (Continued) | | |

FOREIGN PATENT DOCUMENTS

| AU | 2002 300 129 B2 | 6/2005 |
| CN | 103429170 A | 12/2013 |
| (Continued) | | |

OTHER PUBLICATIONS

U.S. Appl. No. 14/314,298.
(Continued)

*Primary Examiner* — Chelsea E Stinson
(74) *Attorney, Agent, or Firm* — Frost Brown Todd LLC

(57) ABSTRACT

A surgical instrument comprises a body, shaft, and end effector. The shaft couples the end effector and body together. The end effector comprises an anvil and lower jaw configured to receive a surgical staple cartridge. The anvil is configured to pivot toward and away from the staple cartridge and lower jaw. The shaft assembly comprises a knife member configured to longitudinally translate to thereby substantially simultaneously cut clamped tissue and staple the severed tissue. The end effector may comprise lockout features configure to prevent longitudinal translation of the knife member. The end effector or staple cartridge may comprise lockout bypass features configured to prevent lockout of the knife member.

20 Claims, 98 Drawing Sheets

(51) Int. Cl.
*A61B 17/10* (2006.01)
*A61B 90/00* (2016.01)
*A61B 17/00* (2006.01)
*A61B 50/30* (2016.01)
*A61B 17/29* (2006.01)

(52) U.S. Cl.
CPC ............ *A61B 17/105* (2013.01); *A61B 50/30* (2016.02); *A61B 2017/0023* (2013.01); *A61B 2017/0046* (2013.01); *A61B 2017/00389* (2013.01); *A61B 2017/00424* (2013.01); *A61B 2017/00734* (2013.01); *A61B 2017/07271* (2013.01); *A61B 2017/07278* (2013.01); *A61B 2017/2923* (2013.01); *A61B 2017/2927* (2013.01); *A61B 2017/2946* (2013.01); *A61B 2050/314* (2016.02); *A61B 2090/0814* (2016.02)

(56) References Cited

U.S. PATENT DOCUMENTS

| | | | |
|---|---|---|---|
| 5,415,334 | A | 5/1995 | Williamson et al. |
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,792,135 | A | 8/1998 | Madhani et al. |
| 5,814,055 | A | 9/1998 | Knodel et al. |
| 5,817,084 | A | 10/1998 | Jensen |
| 5,878,193 | A | 3/1999 | Wang et al. |
| 6,131,789 | A | 10/2000 | Schulze et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,303,108 | B2 | 12/2007 | Shelton, IV |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,524,230 | B2 | 4/2009 | Thai |
| 7,644,848 | B2 | 1/2010 | Swayze et al. |
| 7,691,098 | B2 | 4/2010 | Wallace et al. |
| 7,721,930 | B2 | 5/2010 | McKenna et al. |
| 7,806,891 | B2 | 10/2010 | Nowlin et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,479,969 | B2 | 7/2013 | Shelton, IV |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,608,046 | B2 | 12/2013 | Laurent et al. |
| 8,616,431 | B2 | 12/2013 | Timm et al. |
| 8,636,766 | B2 | 1/2014 | Milliman et al. |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,060,770 | B2 | 6/2015 | Shelton, IV et al. |
| 9,186,142 | B2 | 11/2015 | Fanelli et al. |
| 9,301,759 | B2 | 4/2016 | Spivey et al. |
| 9,307,989 | B2 | 4/2016 | Shelton, IV et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,867,615 | B2 | 1/2018 | Fanelli et al. |
| 10,064,620 | B2 | 9/2018 | Gettinger et al. |
| 10,092,292 | B2 | 10/2018 | Boudreaux et al. |
| 10,314,577 | B2 | 6/2019 | Laurent et al. |
| 2014/0166724 | A1 | 6/2014 | Schellin et al. |
| 2014/0166725 | A1 | 6/2014 | Schellin et al. |
| 2014/0263567 | A1* | 9/2014 | Williams et al. .... A61B 17/068 |
| 2015/0374360 | A1 | 12/2015 | Scheib et al. |
| 2015/0374361 | A1 | 12/2015 | Gettinger et al. |
| 2015/0374363 | A1 | 12/2015 | Laurent et al. |
| 2015/0374373 | A1 | 12/2015 | Rector et al. |

FOREIGN PATENT DOCUMENTS

| | | |
|---|---|---|
| CN | 105120770 A | 12/2015 |
| EP | 2 100 562 A2 | 9/2009 |
| EP | 2 532 312 A2 | 12/2012 |

OTHER PUBLICATIONS

Chinese Office Action, Notification of the First Office Action, and Search Report dated Sep. 11, 2018 for Application No. CN 201580034314.6, 4 pgs.
European Search Report, Partial, and Written Opinion dated Nov. 30, 2015 for Application No. EP 15173666.7, 9 pgs.
European Examination Report dated Dec. 21, 2016 for Application No. EP 15173666.7, 4 pgs.
European Examination Report dated Nov. 14, 2017 for Application No. EP 15173666.7, 5 pgs.
International Search Report and Written Opinion dated Jan. 25, 2016 for Application No. PCT/US2015/034095, 17 pgs.
Chinese Office Action dated May 7, 2019 for Application No. 201580034314.6, 6 pages.
Chinese Supplementary Search dated Jul. 31, 2019 for Application No. 201580034314.6, 1 page.
Chinese Office Action dated Aug. 30, 2019 for Application No. 201580034314.6, 5 pages.

\* cited by examiner

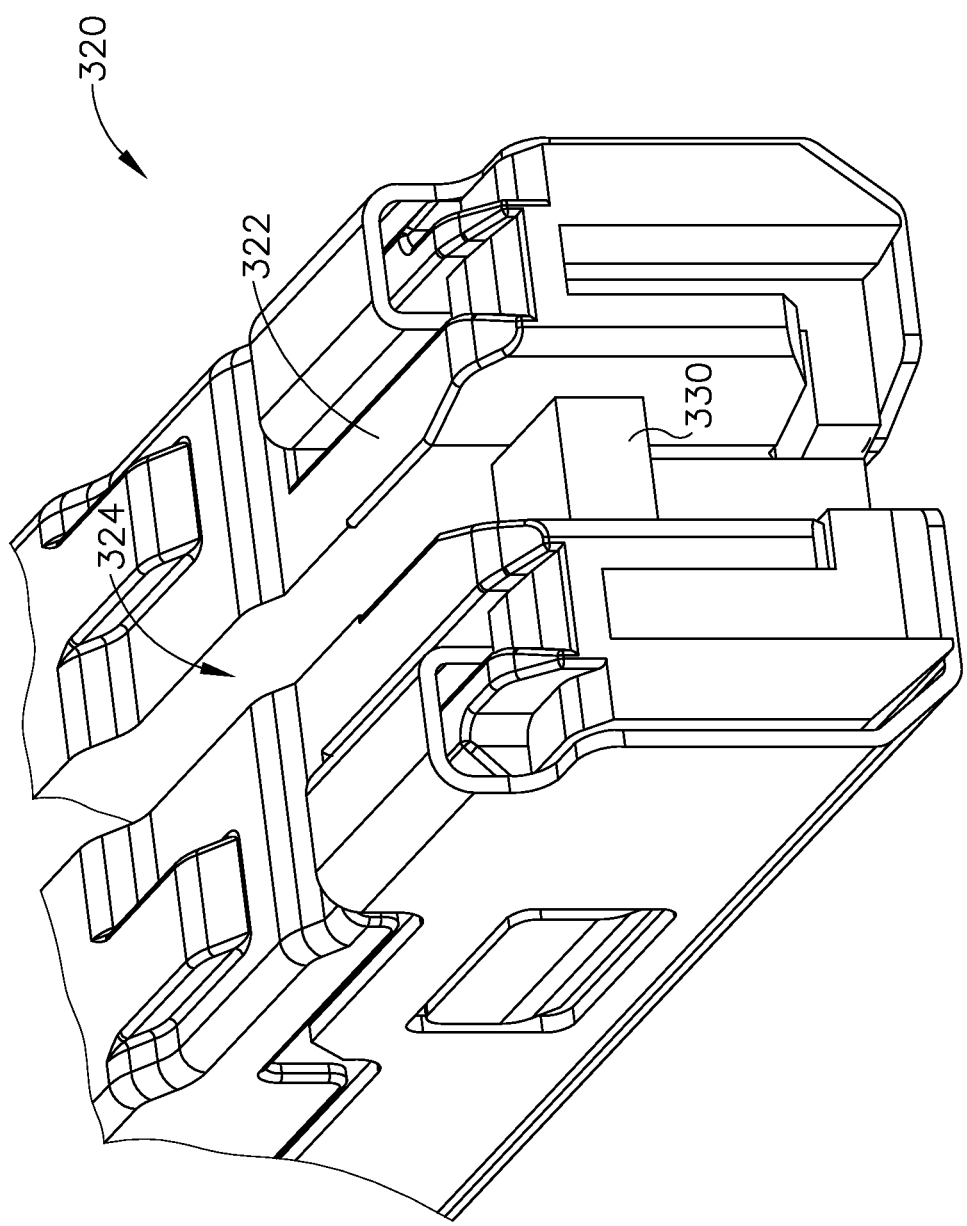

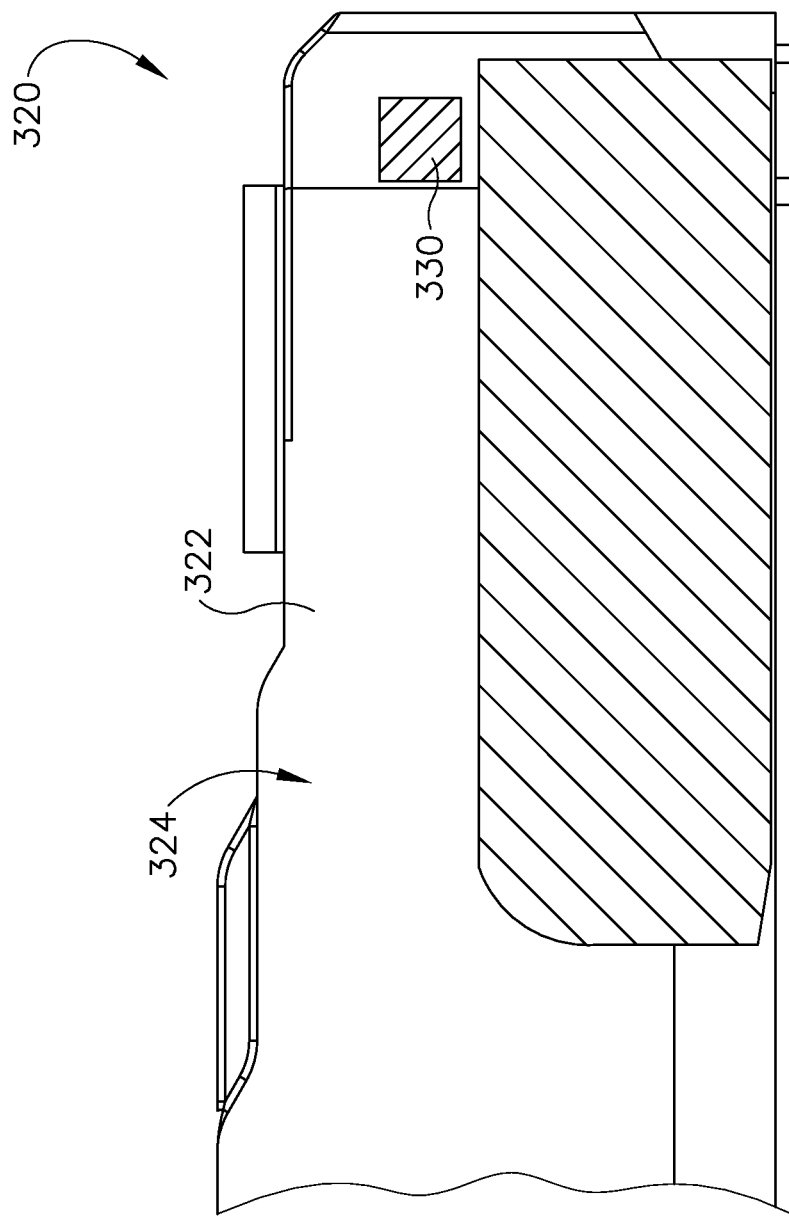

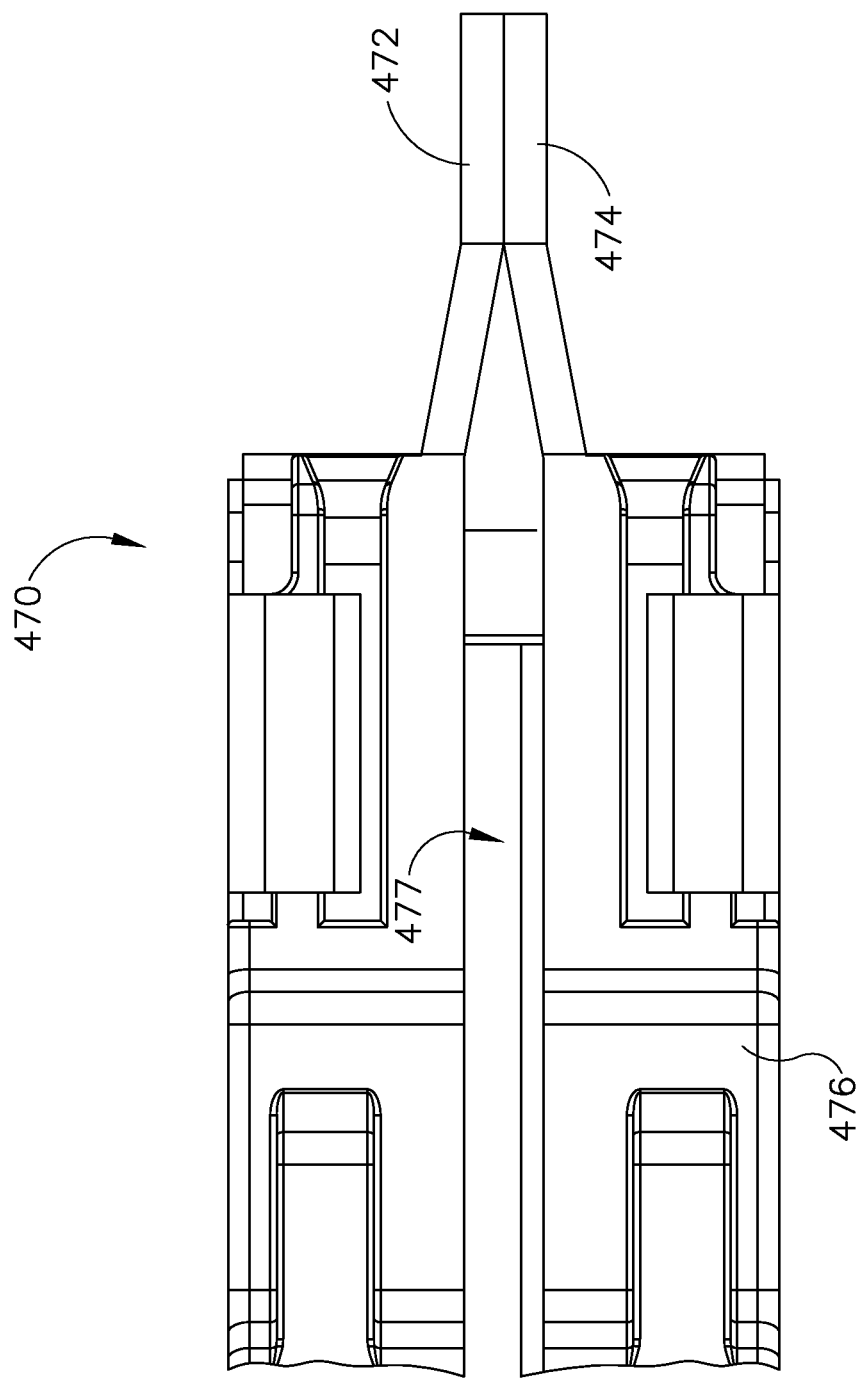

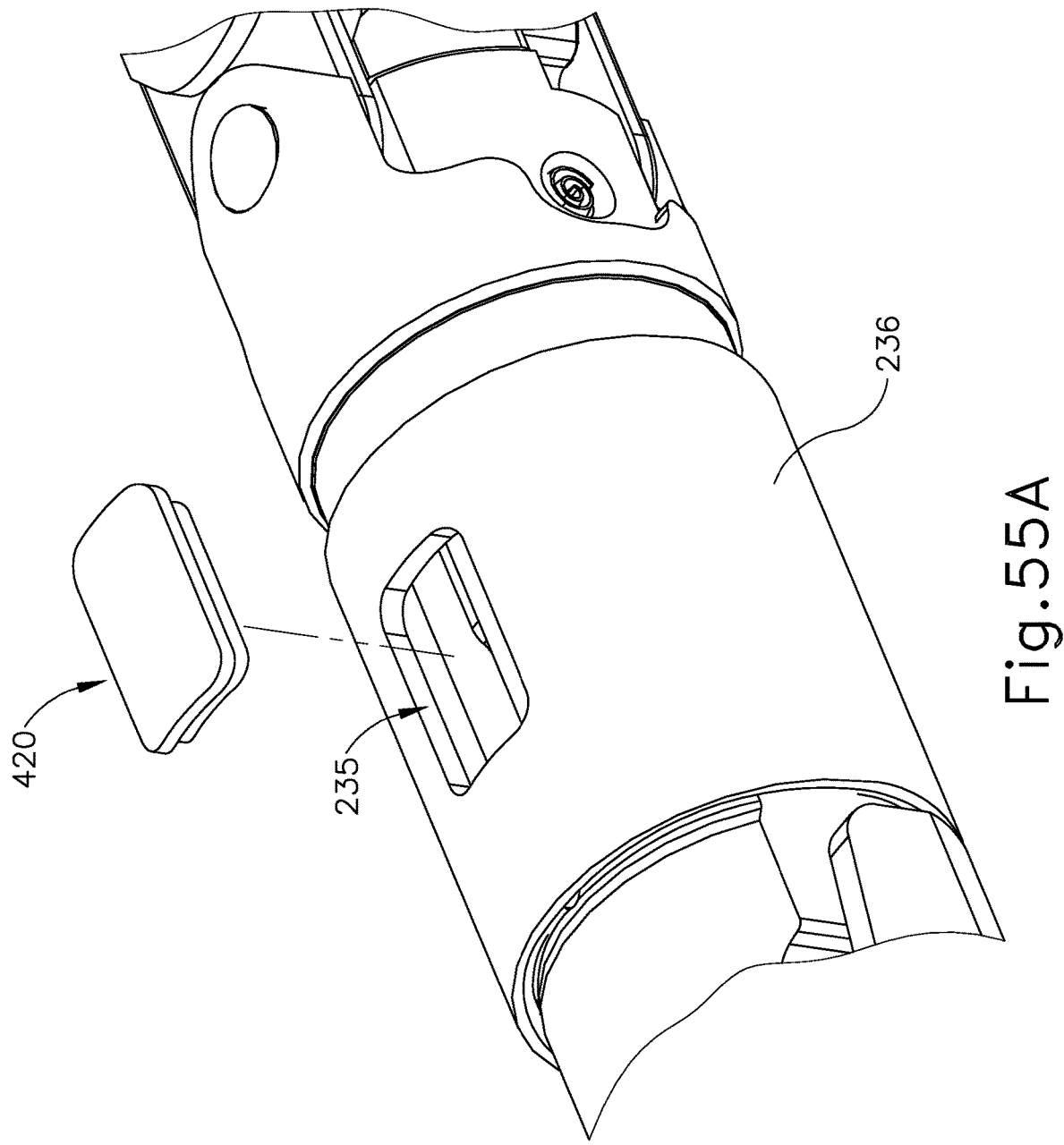

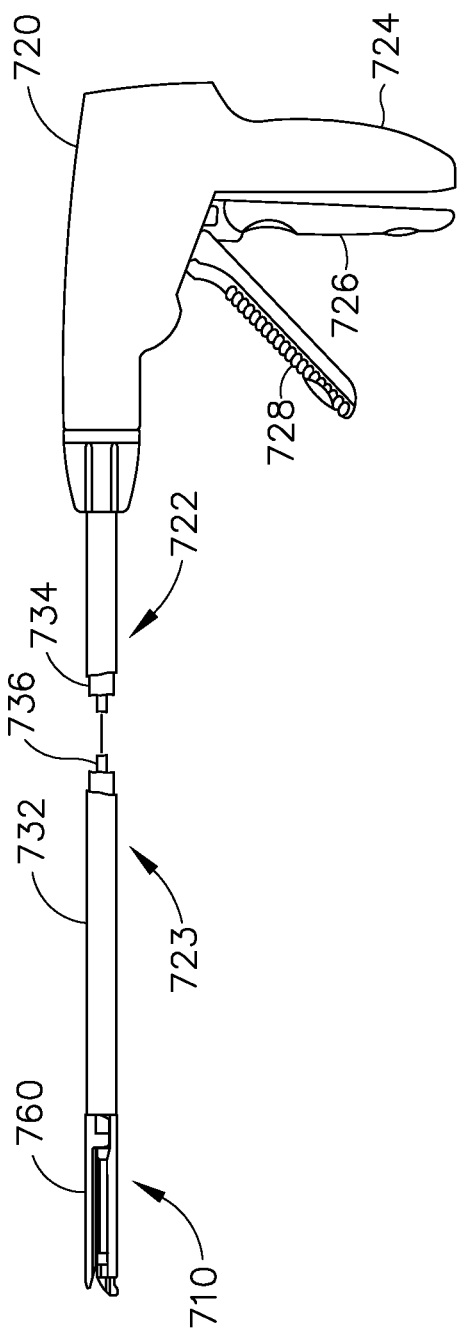
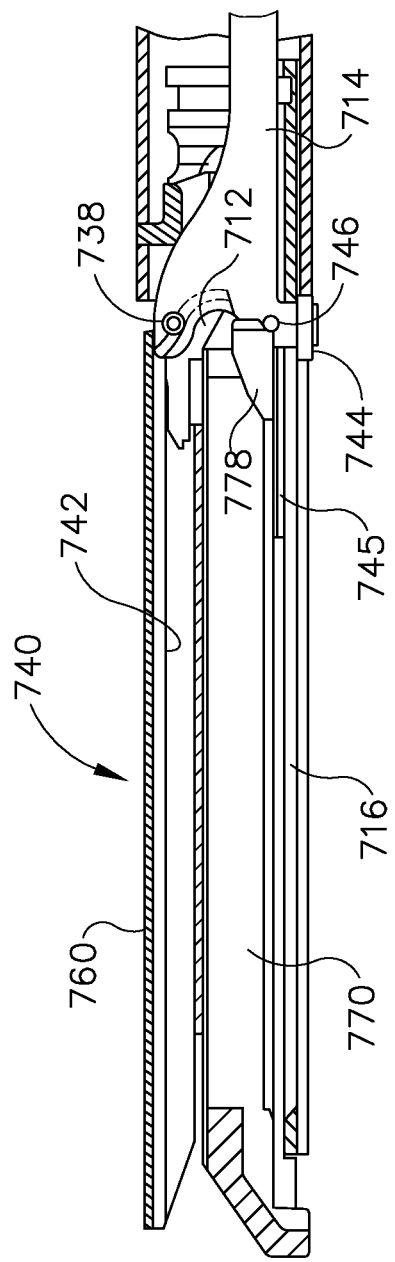
Fig. 64
Fig. 65

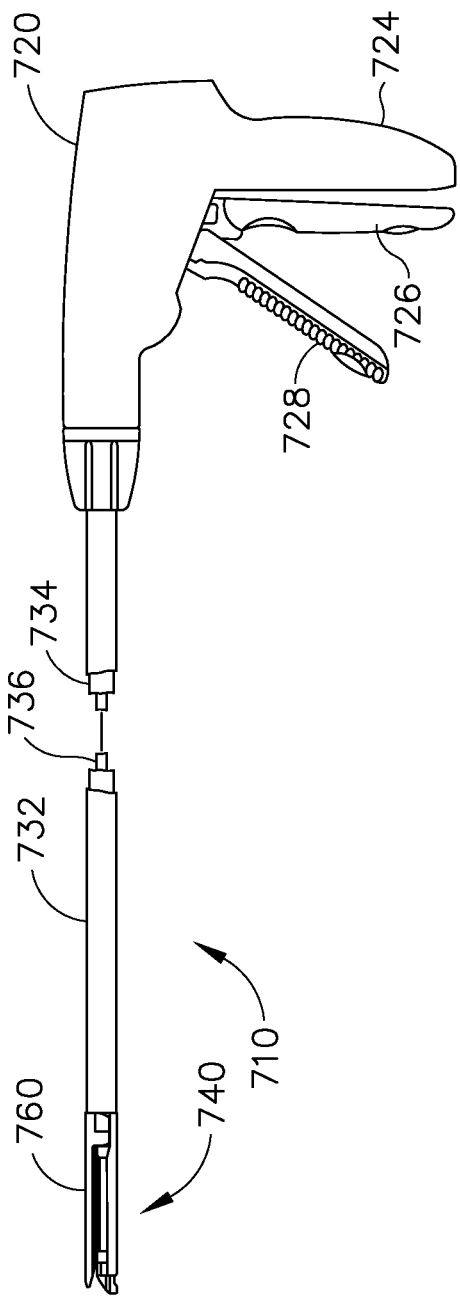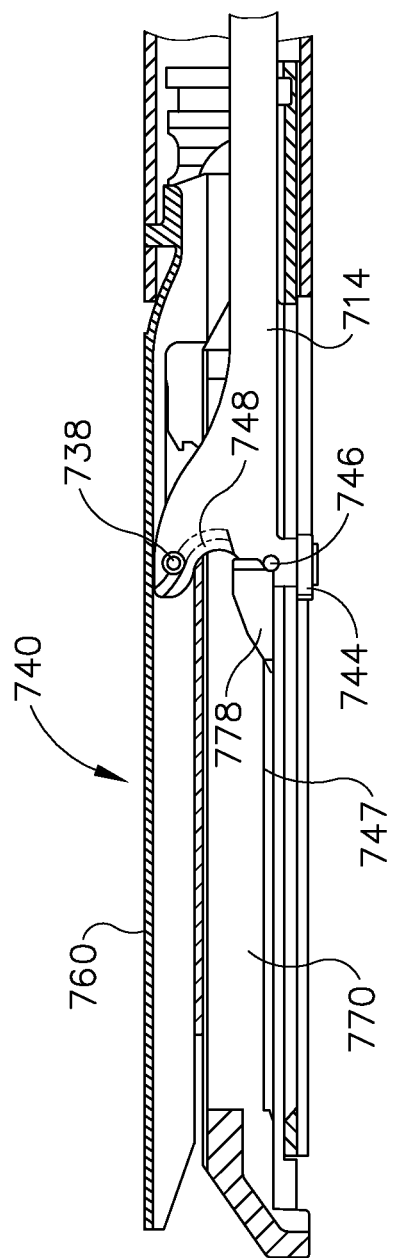

LOCKOUT ENGAGEMENT FEATURES FOR SURGICAL STAPLER

This application is a continuation of U.S. patent application Ser. No. 14/314,298, entitled "Lockout Engagement Features for Surgical Stapler," filed Jun. 25, 2014 and published as U.S. Pat. Pub. No. 2015/0374363 on Dec. 31, 2015, issued as U.S. Pat. No. 10,314,577 on Jun. 11, 2019.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to cut and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 13/780,067, entitled "Surgical Instrument End Effector Articulation Drive with Pinion and Opposing Racks," filed Feb. 28, 2013, now U.S. Pat. No. 9,186,142, issued Nov. 17, 2015; U.S. patent application Ser. No. 13/780,082, entitled "Lockout Feature for Movable Cutting Member of Surgical Instrument," filed Feb. 28, 2013, now U.S. Pat. No. 9,717,497, issued Aug. 1, 2017; U.S. patent application Ser. No. 13/780,106, entitled "Integrated Tissue Positioning and Jaw Alignment Features for Surgical Stapler," filed Feb. 28, 2013, now U.S. Pat. No. 9,517,065, issued Dec. 13, 2016; U.S. patent application Ser. No. 13/780,120, entitled "Jaw Closure Feature for End Effector of Surgical Instrument," filed Feb. 28, 2013, now U.S. Pat. No. 9,839,421, issued Dec. 12, 2017; U.S. patent application Ser. No. 13/780,162, entitled "Surgical Instrument with Articulation Lock having a Detenting Binary Spring," filed Feb. 28, 2013, now U.S. Pat. No. 9,867,615, issued Jan. 16, 2018; U.S. patent application Ser. No. 13/780,171, entitled "Distal Tip Features for End Effector of Surgical Instrument," filed Feb. 28, 2013, now U.S. Pat. No. 9,622,746, issued Apr. 18, 2017; U.S. patent application Ser. No. 13/780,379, entitled "Staple Forming Features for Surgical Stapling Instrument," filed Feb. 28, 2013, now U.S. Pat. No. 10,092,292, issued Oct. 9, 2018; U.S. patent application Ser. No. 13/780,402, entitled "Surgical Instrument with Multi-Diameter Shaft," filed Feb. 28, 2013, now U.S. Pat. No. 9,795,379, issued Oct. 24, 2017; and U.S. patent application Ser. No. 13/780,417, entitled "Installation Features for Surgical Instrument End Effector Cartridge," filed Feb. 28, 2013 now U.S. Pat. No. 9,808,248, issued Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 30 depicts a perspective view of the proximal end of another exemplary alternative cartridge that may be incorporated into the end effector of FIG. 13;

FIG. 31 depicts a cross-sectional side view of the proximal end of the cartridge of FIG. 30;

FIG. 45A depicts a top view of the proximal end of the cartridge of FIG. 44A with the guide fins in the closed position;

FIG. 55A depicts a perspective view of the end effector of FIG. 13, with the tab insert of FIG. 54 positioned to couple with the end effector;

FIG. 64 depicts a side view of the surgical stapling instrument of FIG. 59, with the end effector in the closed position;

FIG. 65 depicts a cross-sectional side view of the end effector of FIG. 60 in the closed position with tissue properly compressed;

FIG. 66 depicts a side view of the surgical stapling instrument of FIG. 59 in a partially fired position;

FIG. 67 depicts a cross-sectional side view of the end effector of FIG. 60 in the partially fired position;

Figure 1:
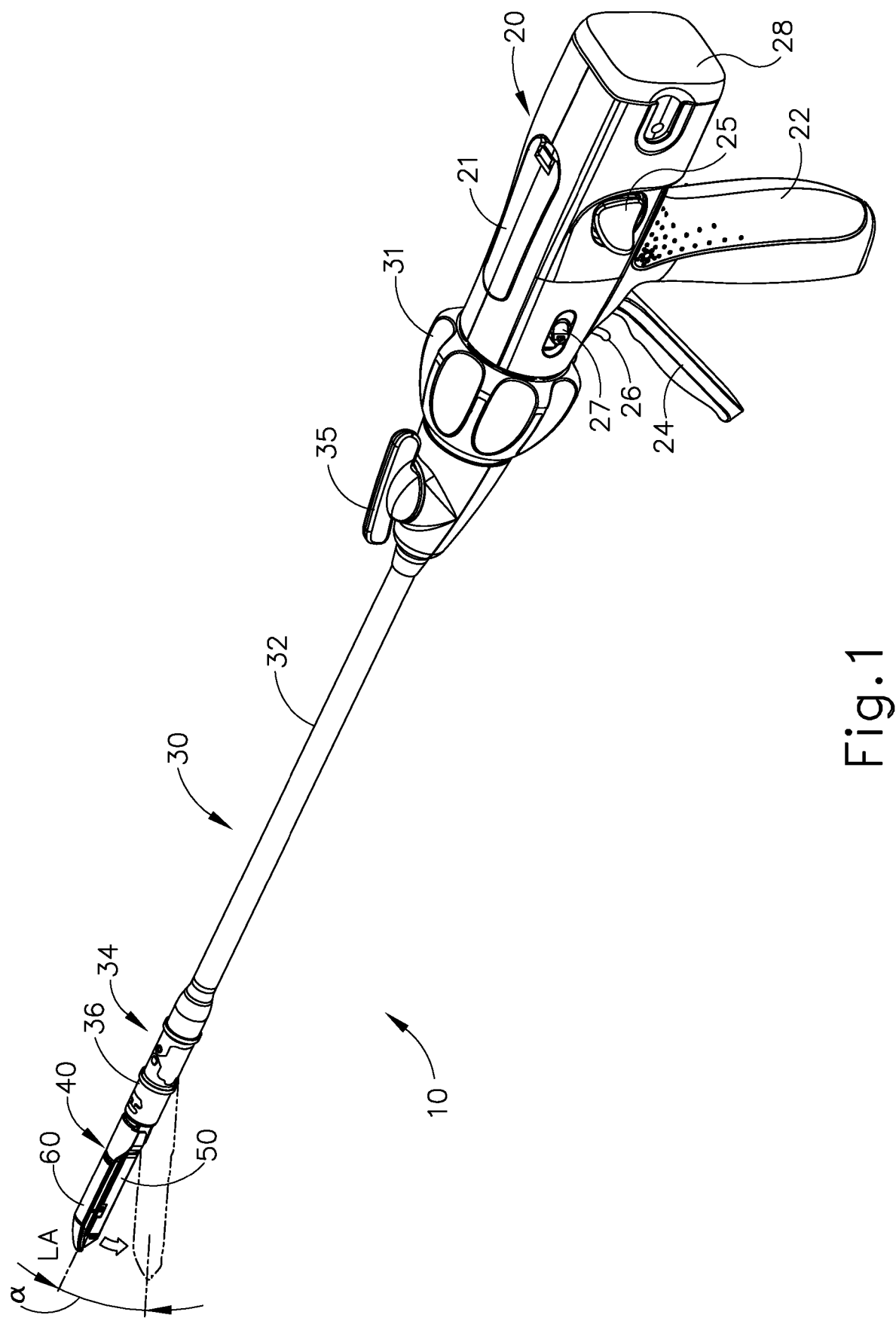
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIG. 1 depicts an exemplary surgical stapling and cutting instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
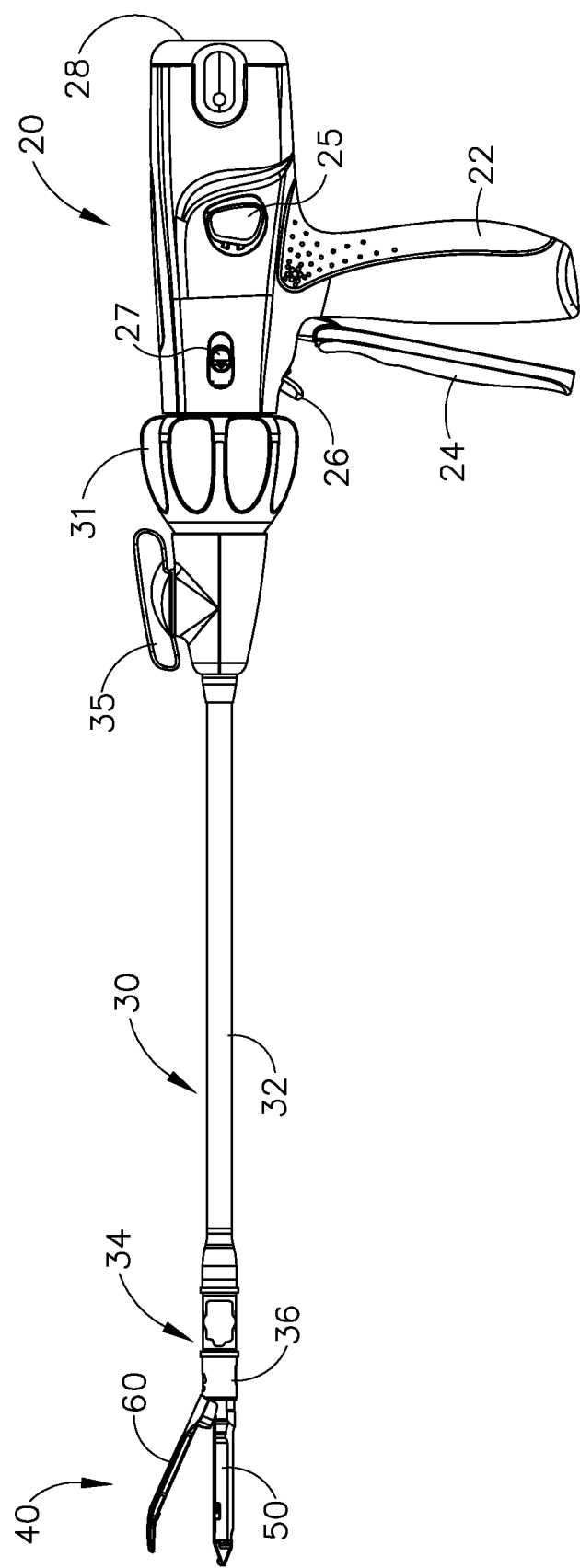
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
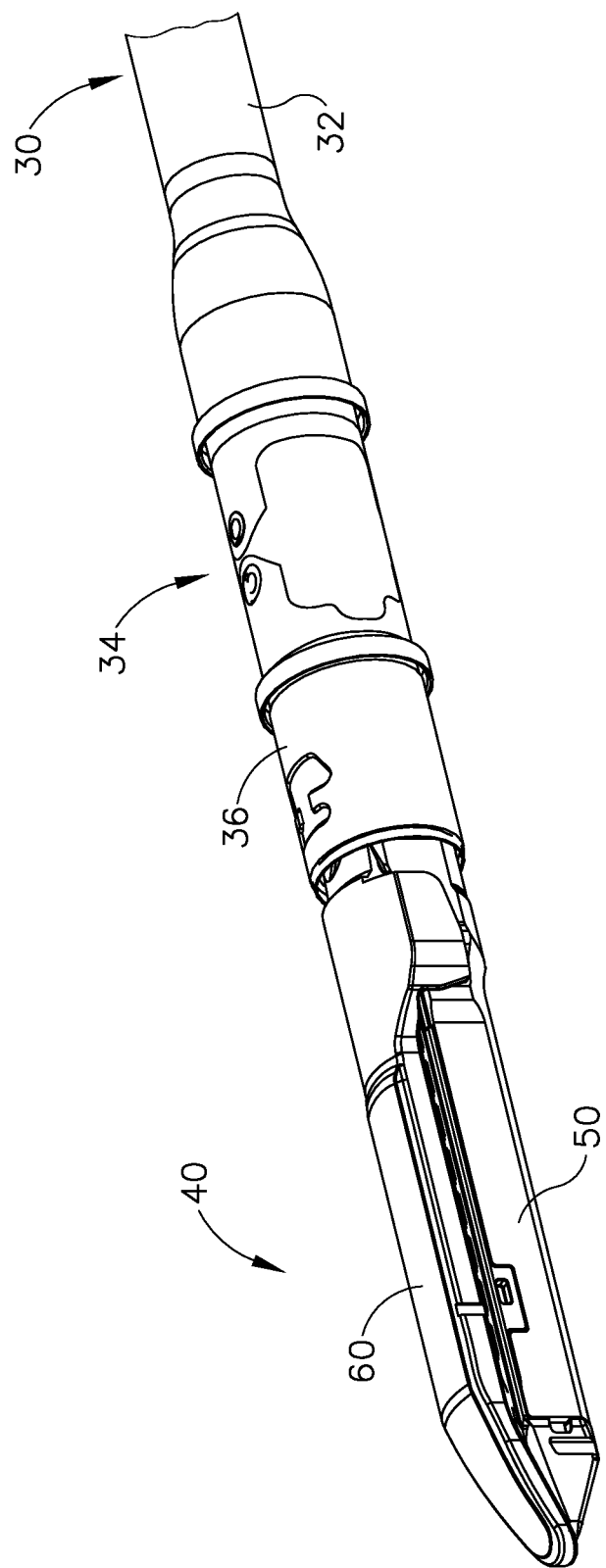
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, now U.S. Pat. No. 9,186,142, issued Nov. 17, 2015, the disclosure of which is incorporated by reference herein. Articulation section (34) may also be constructed and operable in accordance with at least some of the teachings of U.S. patent application Ser. No. 14/314,125, filed Jun. 25, 2014, published as U.S. Patent Pub. No. 2015/0374360 on Dec. 31, 2015, issued as U.S. Pat. No. 10,292,701 on May 21, 2019, entitled "Articulation Drive Features for Surgical Stapler," , the disclosure of which is incorporated by reference herein; and/or U.S. patent application Ser. No. 14/314,276, filed Jun. 25, 2014, now U.S. patent Ser. No. 10/064,620, issued Sep. 4, 2018, entitled "Method of Unlocking Articulation Joint in Surgical Stapler," filed on even date herewith, the disclosure of which is incorporated by reference herein. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. patent application Ser. No. 13/780,402, entitled "Surgical Instrument with Multi-Diameter Shaft," filed Feb. 28, 2013, now U.S. Pat. No. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. patent application Ser. No. 13/780,417, entitled "Installation Features for Surgical Instrument End Effector Cartridge," filed Feb. 28, 2013 now U.S. Pat. No. 9,808,248, issued Nov. 7, 2017, the disclosure of which is incorporated by reference herein. Other suitable forms that lower jaw (50) may take will be apparent to those of ordinary skill in the art in view of the teachings herein.

Figure 4:
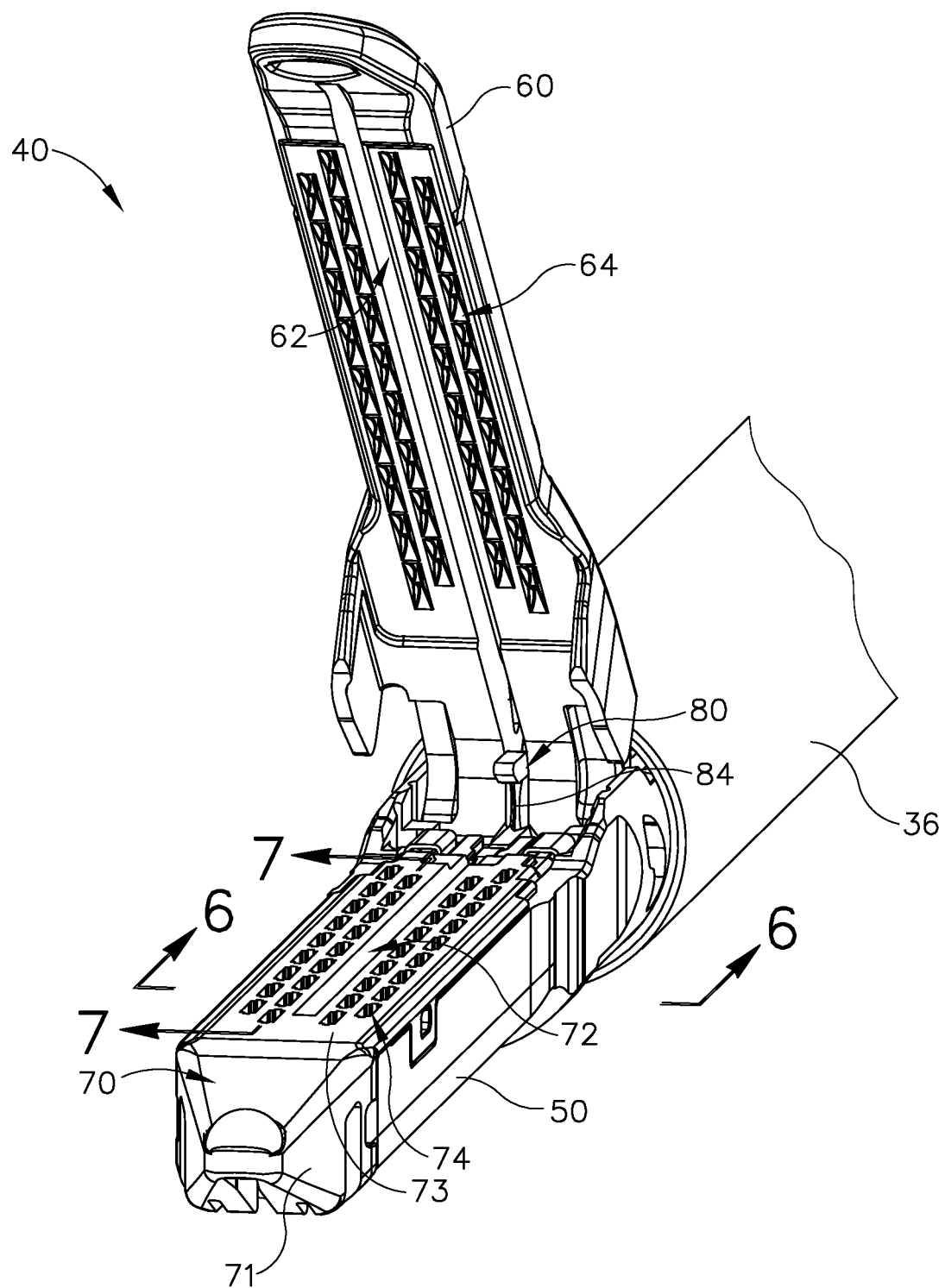
FIG. 4 depicts a perspective view of the end effector of FIG. 3, with the end effector in an open configuration.
Figure 5:
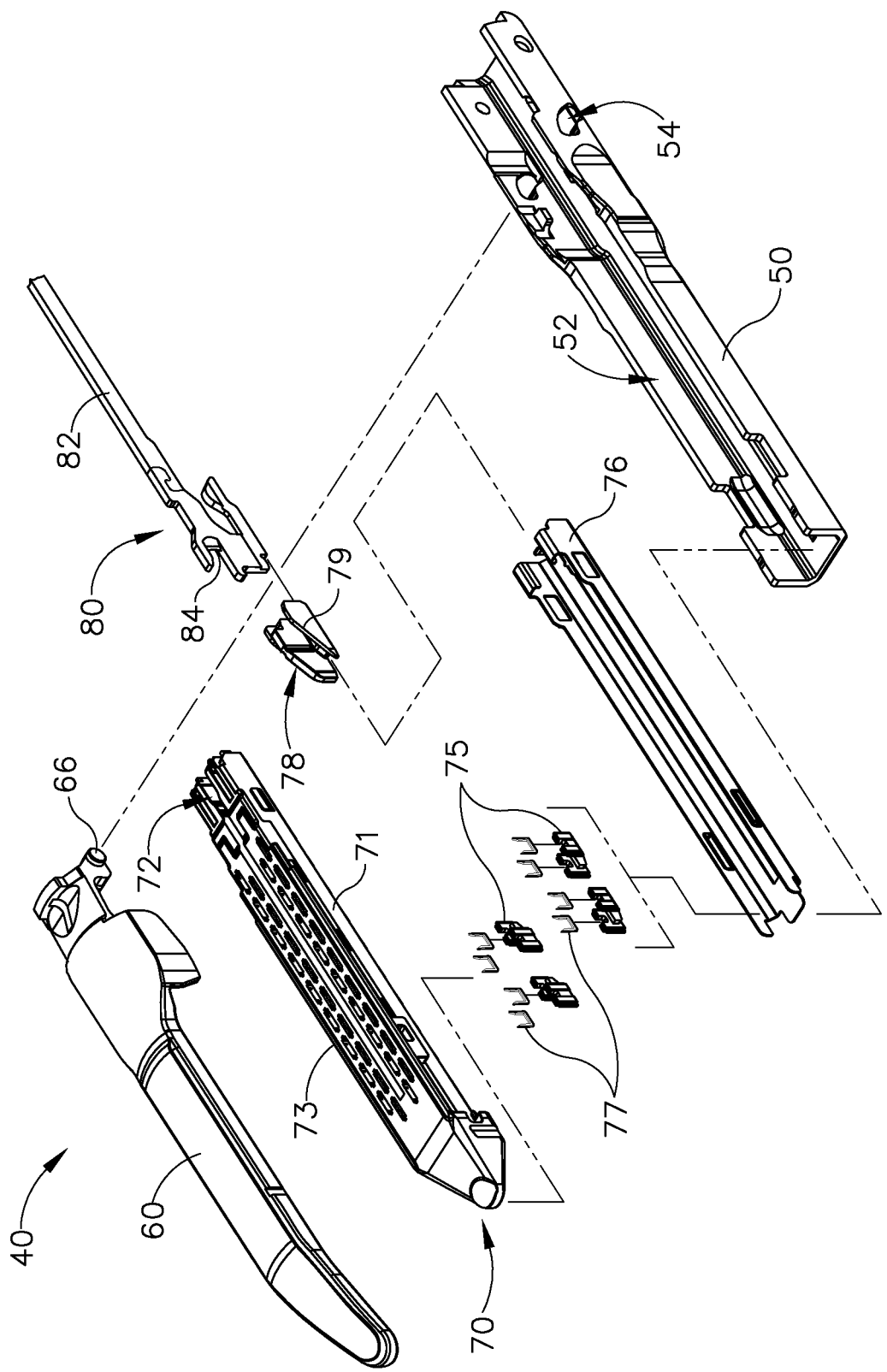
FIG. 5 depicts an exploded perspective view of the end effector of FIG. 3.
Figure 6:
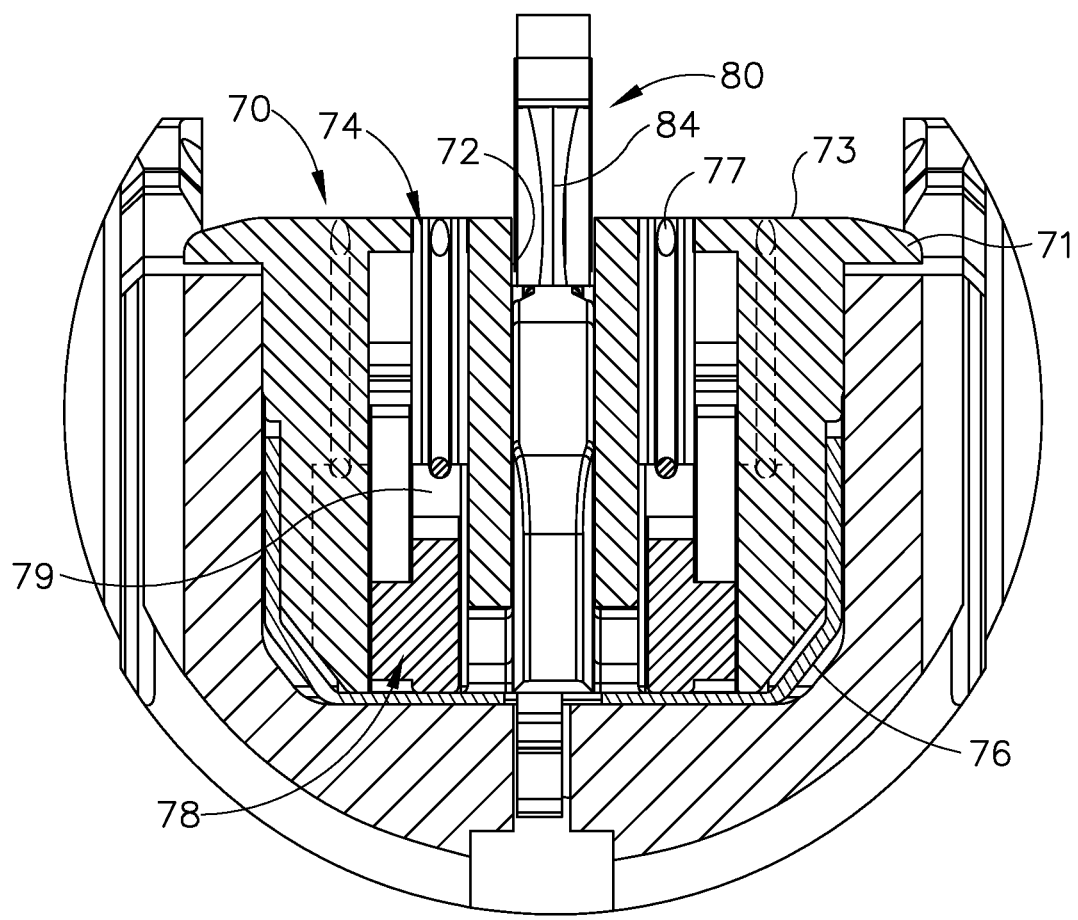
FIG. 6 depicts a cross-sectional end view of the end effector of FIG. 3, taken along line 6-6 of FIG. 4.
Figure 7A:
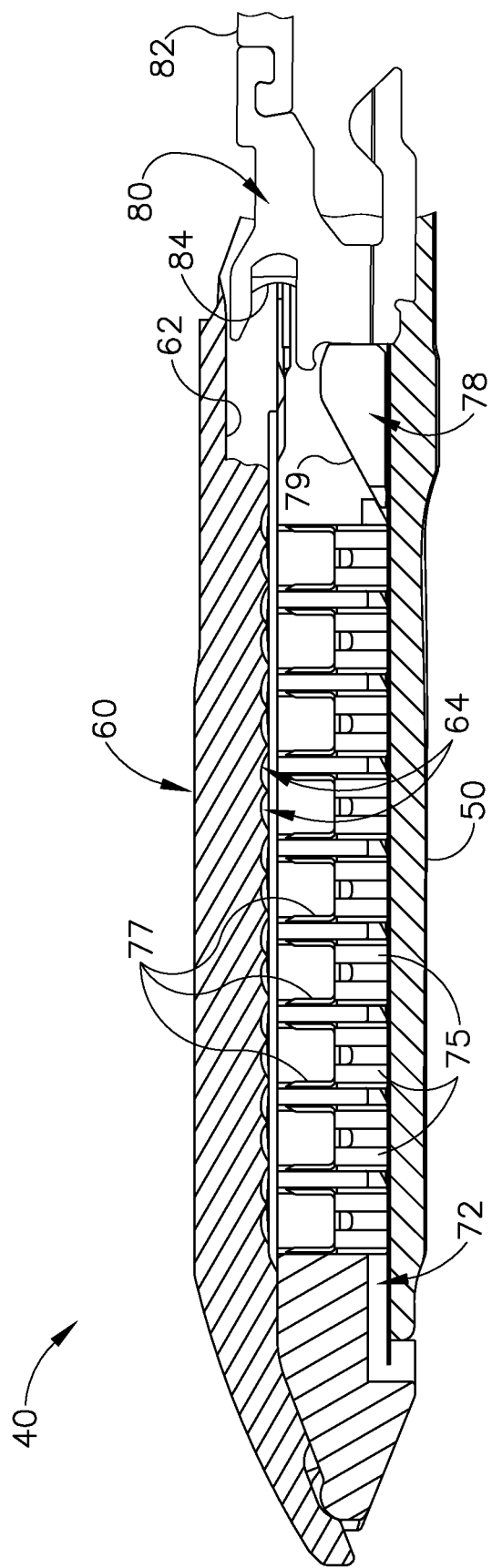
FIG. 7A depicts a cross-sectional side view of the end effector of FIG. 3, taken along line 7-7 of FIG. 4, with the firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (74) are located in staple pockets (74). As wedge sled (78) is driven to the distal position shown in FIG. 7B by a translating knife member (80), wedge sled (78) drives staple drivers (75) upwardly, thereby driving staples (74) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. patent application Ser. No. 13/780,106, entitled "Integrated Tissue Positioning and Jaw Alignment Features for Surgical Stapler," filed Feb. 28, 2013, now U.S. Pat. No. 9,517,065, issued Dec. 13, 2016, the disclosure of which is incorporated by reference herein. In addition or in the alternative, staple cartridge (70) may be constructed and operable in accordance with at least some of the teachings of U.S. patent application Ser. No. 13/780,417, entitled "Installation Features for Surgical Instrument End Effector Cartridge," filed Feb. 28, 2013, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, now U.S. Pat. No. 9,517,065, issued Dec. 13, 2016; at least some of the teachings of U.S. patent application Ser. No. 13/780,120, entitled "Jaw Closure Feature for End Effector of Surgical Instrument," filed Feb. 28, 2013, now U.S. Pat. No. 9,839,421, issued Dec. 12, 2017; and/or at least some of the teachings of U.S. patent application Ser. No. 13/780,379, entitled "Staple Forming Features for Surgical Stapling Instrument," filed Feb. 28, 2013, now U.S. Pat. No. 10,092,292, issued Oct. 9, 2018, the disclosure of which is incorporated by reference herein. Other suitable forms that anvil (60) may take will be apparent to those of ordinary skill in the art in view of the teachings herein.

Figure 7B:
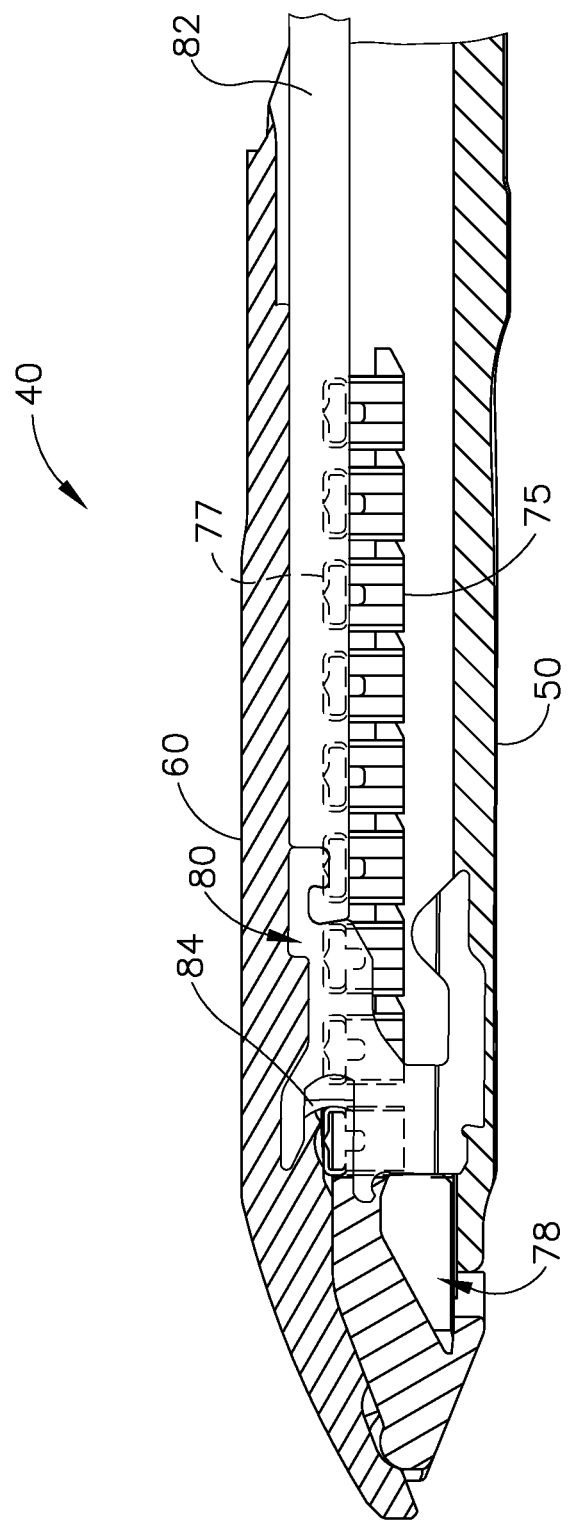
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to cut tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (74) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. patent application Ser. No. 13/780,082, entitled "Lockout Feature for Movable Cutting Member of Surgical Instrument," filed Feb. 28, 2013, now U.S. Pat. No. 9,717,497, issued Aug. 1, 2017, the disclosure of which is incorporated by reference herein; and/or at least some of the teachings below. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. patent application Ser. No. 13/780,120, entitled "Jaw Closure Feature for End Effector of Surgical Instrument," filed Feb. 28, 2013, now U.S. Pat. No. 9,839,421, issued Dec. 12, 2017, the disclosure of which is incorporated by reference herein; and/or in accordance with at least some of the teachings of U.S. patent application Ser. No. 14/314,164, filed Jun. 25, 2014, published as U.S. Patent Pub. No. 2015/0374361 on Dec. 31, 2015, issued as U.S. Pat. No. 10,456,132 on Oct. 29, 2019, entitled "Jaw Opening Feature for Surgical Stapler," , the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

Figure 9:
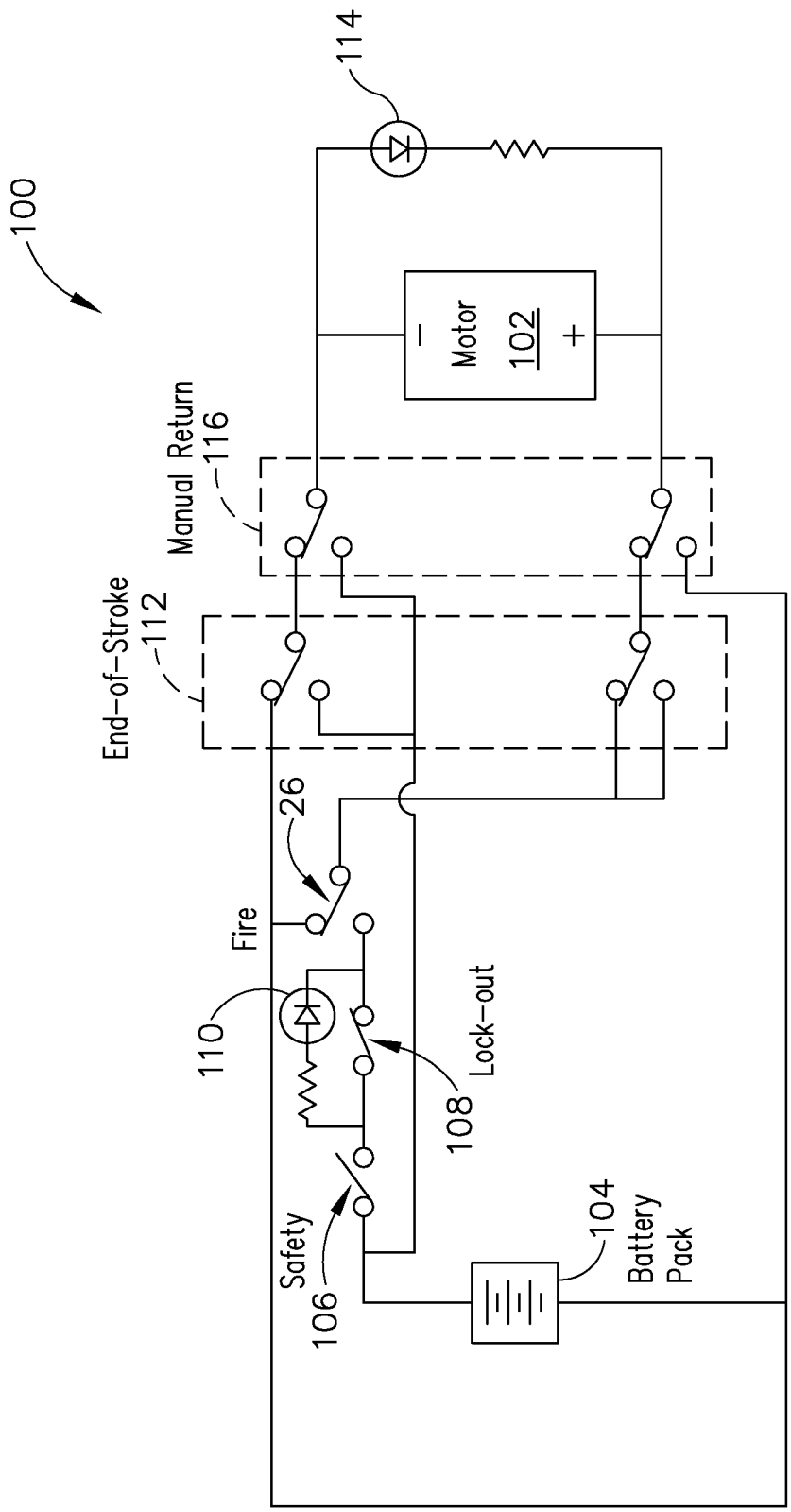
FIG. 9 depicts a schematic view of an exemplary control circuit for use in the instrument of FIG. 1.

In the present example, instrument (10) provides motorized control of firing beam (82). FIGS. 9-12 show exemplary components that may be used to provide motorized control of firing beam (82). In particular, FIG. 9 shows an exemplary control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Figure 12:
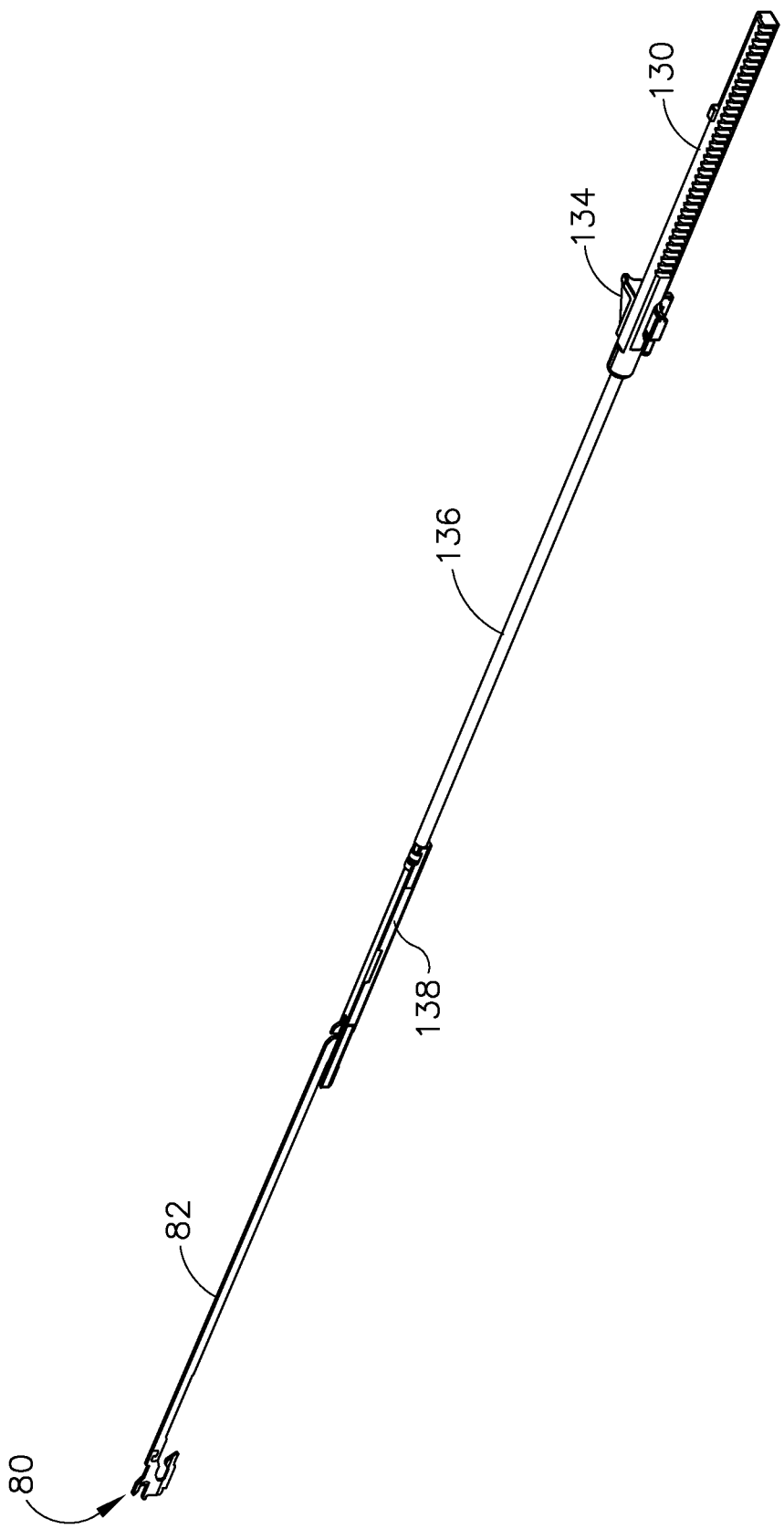
FIG. 12 depicts a perspective view of an elongate member from the drive assembly of FIG. 11, coupled with the firing beam.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (74) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 10:
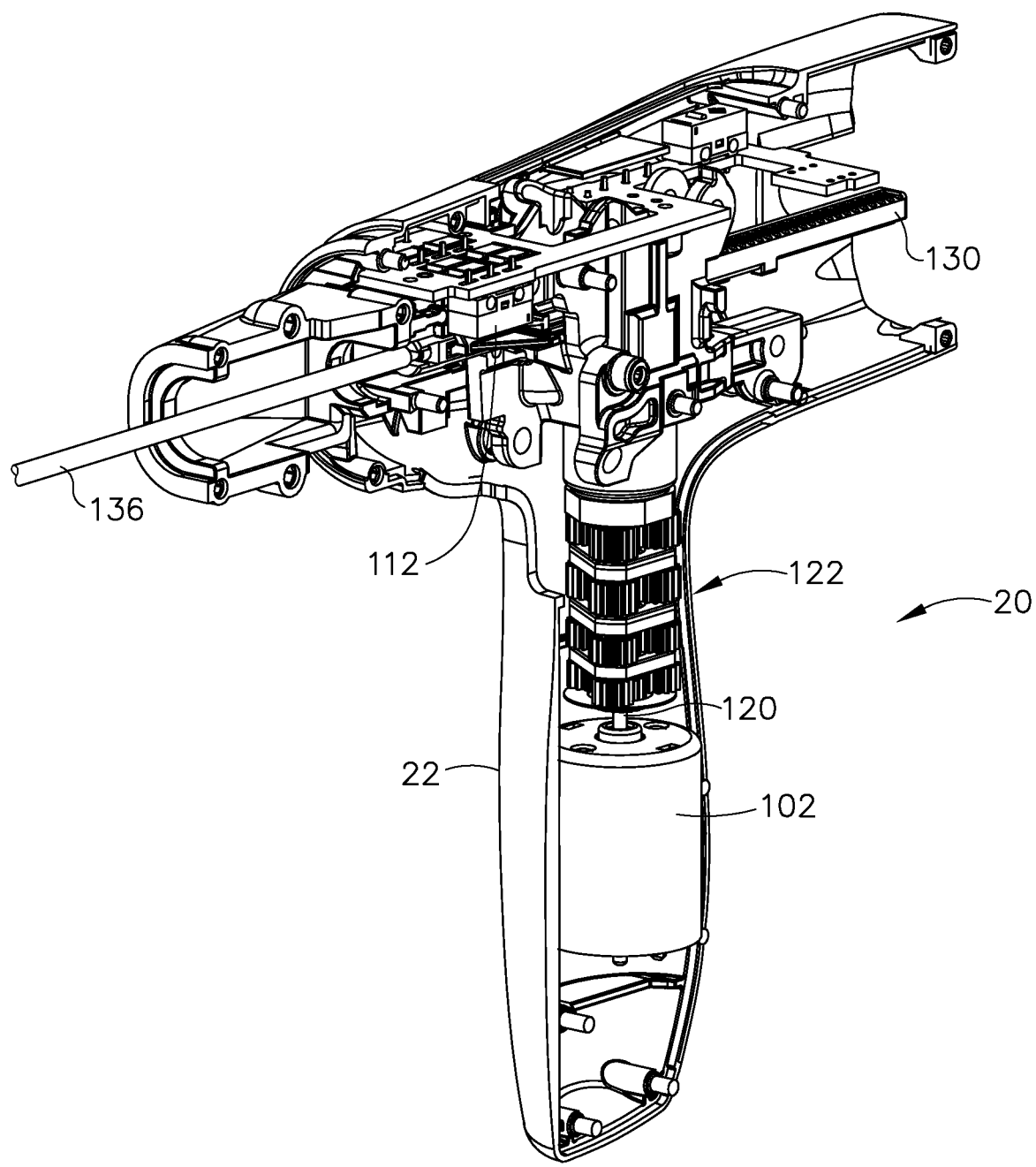
FIG. 10 depicts a perspective view of the handle assembly of the instrument of FIG. 1, with a housing half and some internal components removed.
Figure 11:
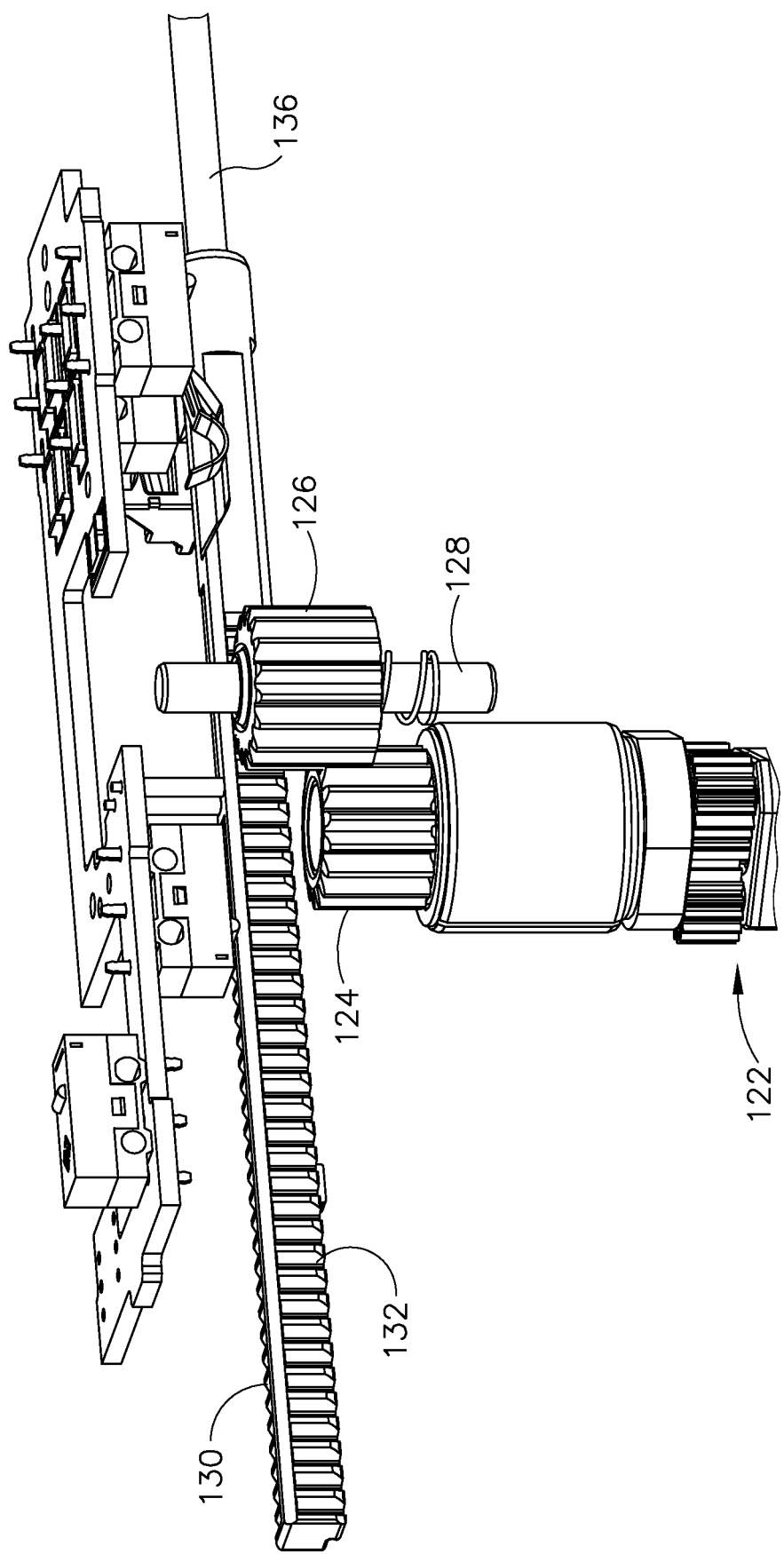
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (130). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
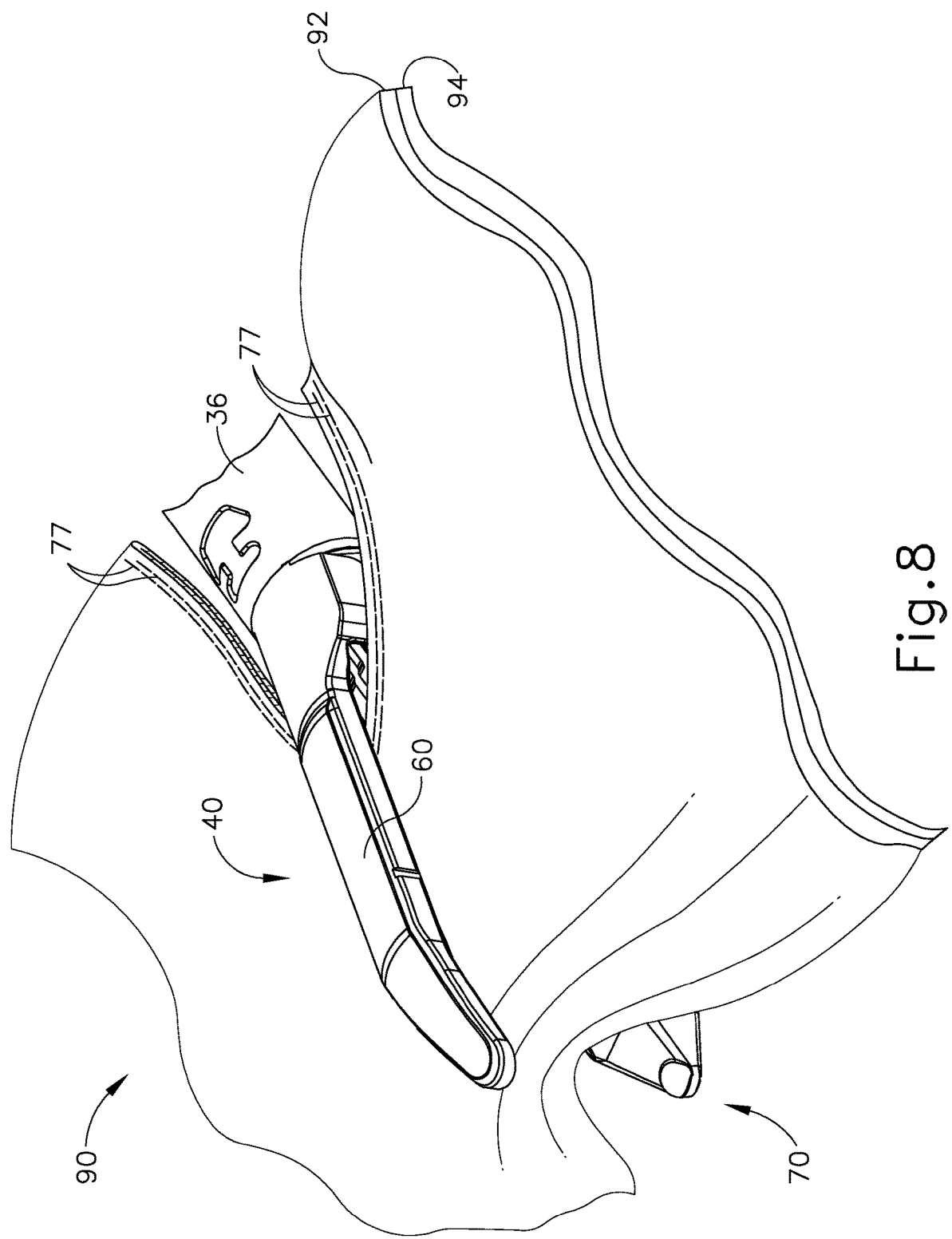
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY END EFFECTOR LOCKOUT FEATURES

In some instances, it may be desirable to provide a lockout feature for end effector (40) to prevent inadvertent firing (i.e.

distal advancement) of firing beam (82) and cutting edge (84) so that tissue positioned between anvil (60) and lower jaw (50) is not severed without being stapled. For example, it may be desirable to prevent firing beam (82) and cutting edge (84) from firing if a staple cartridge (70) has not been loaded within end effector (40) or after staples (77) have been driven from staple cartridge (70). Accordingly, lockout features may be provided within end effector (40) to prevent inadvertent firing of firing beam (82) and cutting edge (84). The examples below include several merely illustrative versions of lockout features that may be readily introduced to an end effector (40).

Figure 13:
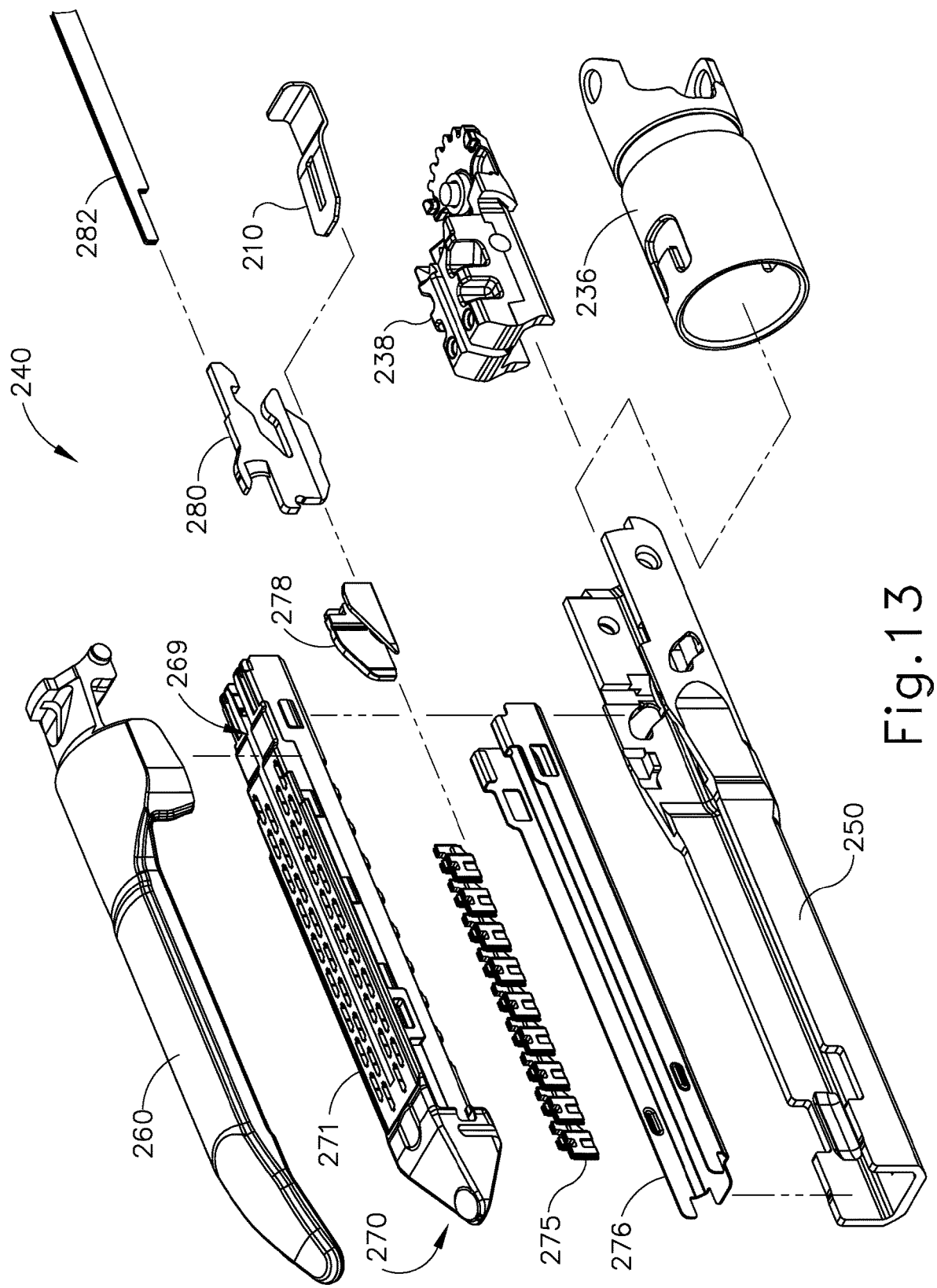
FIG. 13 depicts an exploded view of an exemplary alternative end effector that may be incorporated into the instrument of FIG. 1.

FIG. 13 shows an exemplary end effector (240) that may be readily incorporated into instrument (10). End effector (240) comprises a lower jaw (250), a pivotable anvil (260), and a closure ring (236), which are similar to lower jaw (50), anvil (60), and closure ring (36) of end effector (40). A staple cartridge (270) may be removably installed into a channel of lower jaw (250). Staple cartridge (270) of the present example is similar to staple cartridge (70) of end effector (40). Staple cartridge (270) comprises a cartridge body (271) that is coupled with a lower cartridge tray (276). A wedge sled (278) and a plurality of staple drivers (275) are captured between cartridge body (271) and tray (276), with wedge sled (278) being located proximal to staple drivers (275). Wedge sled (278) is slidably disposed within a channel (269) of cartridge body (271). Although staples, similar to staples (47), have been omitted from FIG. 13 for clarity, it should be understood that staples (277) would be positioned directly above staple drivers (275). Wedge sled (278) and staple drivers (275) are similar to wedge sled (78) and staple drivers (75) of end effector (40) such that wedge sled (278) is configured to urge staple drivers (275) upwardly as wedge sled (278) is driven distally through channel (269) of staple cartridge (270) to drive staples (not shown in FIG. 13) vertically and into tissue positioned between anvil (260) and lower jaw (250). Wedge sled (278) of the present example is driven distally by a translating knife member (280), which is positioned proximally of wedge sled (278). A firing beam (282) is coupled to knife member (280) (e.g., by welding). Firing beam (282) is similar to firing beam (82) and is configured to drive knife member (280) distally and/or proximally. A resilient member (210) is proximal of knife member (280) and is configured to removably engage knife member (280). Knife member (280) and resilient member (210) are positioned within a frame member (238). Frame member (238) is positioned within closure ring (236) and coupled to a proximal end of lower jaw (250) such that frame member (238) couples with articulation section (234) of shaft assembly (230).

Articulation section (234) and shaft assembly (230) are similar to articulation section (34) and shaft assembly (30). By way of example only, articulation section (234) and/or shaft assembly (230) may be constructed in accordance with at least some of the teachings of U.S. patent application Ser. No. 13/780,067, entitled "Surgical Instrument End Effector Articulation Drive with Pinion and Opposing Racks," filed Feb. 28, 2013, now U.S. Pat. No. 9,186,142, issued Nov. 17, 2015, the disclosure of which is incorporated by reference herein; and/or U.S. patent application Ser. No. 13/780,402, entitled "Surgical Instrument with Multi-Diameter Shaft," filed Feb. 28, 2013, now U.S. Pat. No. 9,795,379, issued Oct. 24, 2017, the disclosure of which is incorporated by reference herein. Alternatively, articulation section (234) and/or shaft assembly (230) may have any other suitable configurations.

Figure 14:
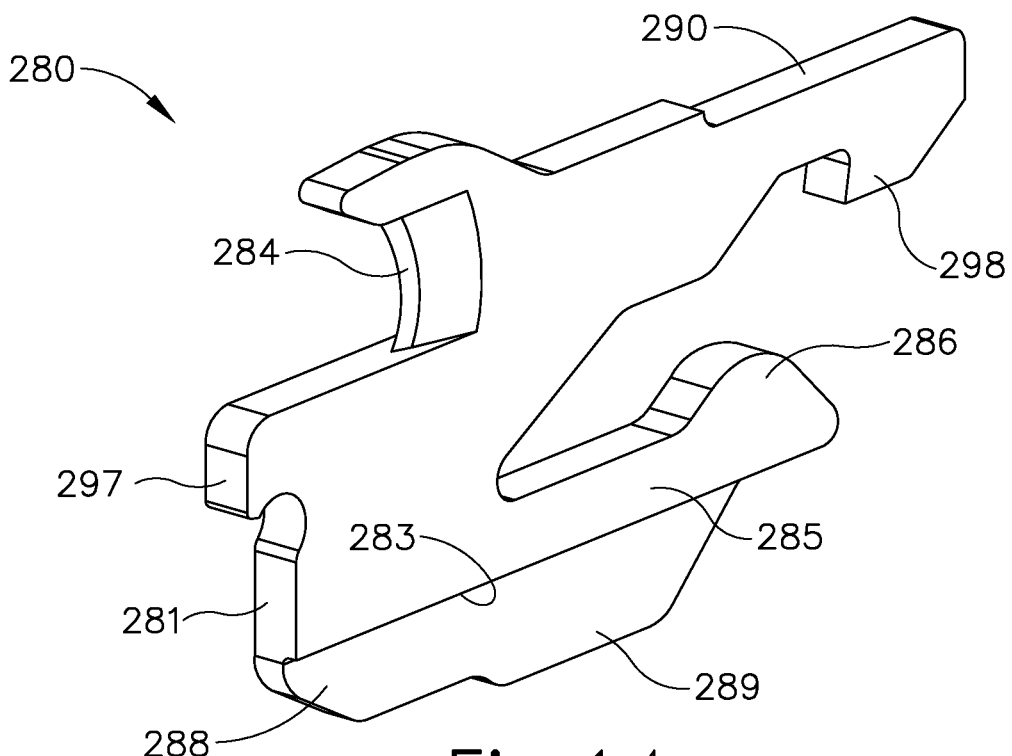
FIG. 14 depicts a perspective view of an exemplary blade of the end effector of FIG. 13.
Figure 15:
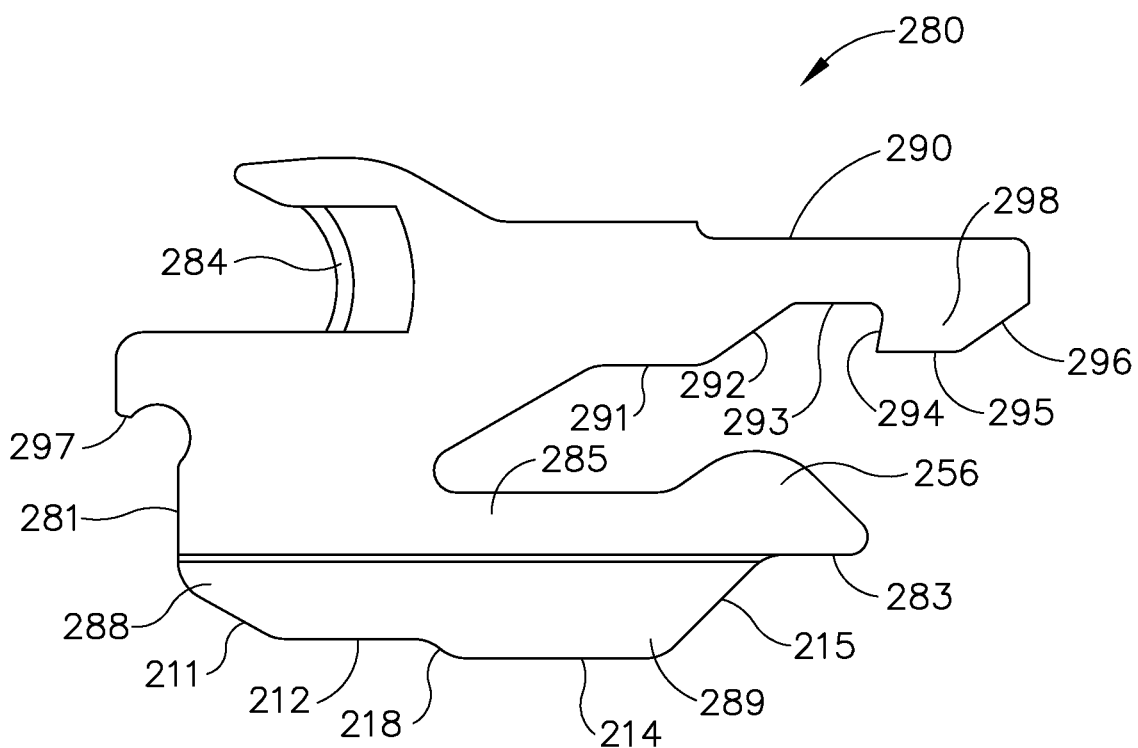
FIG. 15 depicts a side view of the blade of FIG. 14.

FIGS. 14-15 show knife member (280) in more detail. Knife member (280) comprises a cutting edge (284), an upper extension (290), and a lower extension (285). Cutting edge (284) is positioned on an upper distal portion of knife member (280) such that cutting edge (284) severs tissue as knife member (280) translates distally through lower jaw (250). Upper extension (290) extends proximally from cutting edge (284). Upper extension (290) comprises walls (291, 292, 293, 294, 295, 296) on a bottom surface of upper extension (290). Wall (291) extends proximally to wall (292). Wall (292) ramps upwardly to wall (293). Wall (293) extends proximally to wall (294), which extends downwardly to wall (295). Walls (292, 293, 294) together form a notch. Wall (295) extends proximally to wall (296), which ramps upwardly. Walls (294, 295, 296) form tab (298) that extends downwardly from upper extension (290). Tab (298) is configured to engage frame member (238) such that frame member (238) may prevent tab (298) and knife member (280) from advancing distally without a loaded staple cartridge (270), as will be described in greater detail below.

Lower extension (285) extends proximally from underneath cutting edge (284). A distal tip (297) and a distal wall (281) are positioned on a distal portion of lower extension (285). Distal tip (297) extends distally and downwardly from lower extension (285) such that distal tip (297) is configured to engage a top surface of wedge sled (278), as will be described in greater detail below. Distal wall (281) is vertically positioned on the distal portion of lower extension (285) beneath distal tip (297) such that distal wall (281) is configured to engage a proximal surface of wedge sled (278), as will also be described in greater detail below. Accordingly, distal tip (297) and distal wall (281) releasably engage wedge sled (278) when knife member (280) is translated distally within lower jaw (250) to thereby drive wedge sled (278) distally within lower jaw (250). A rounded tab (286) extends upwardly from a proximal portion of lower extension (285). Tab (286) is configured to engage resilient member (210) such that resilient member (210) may bias tab (286) and knife member (280) downwardly such that tab (286) of knife member (280) engages frame member (238) to prevent tab (286) and knife member (280) from advancing distally without a loaded staple cartridge (270).

Figure 17:
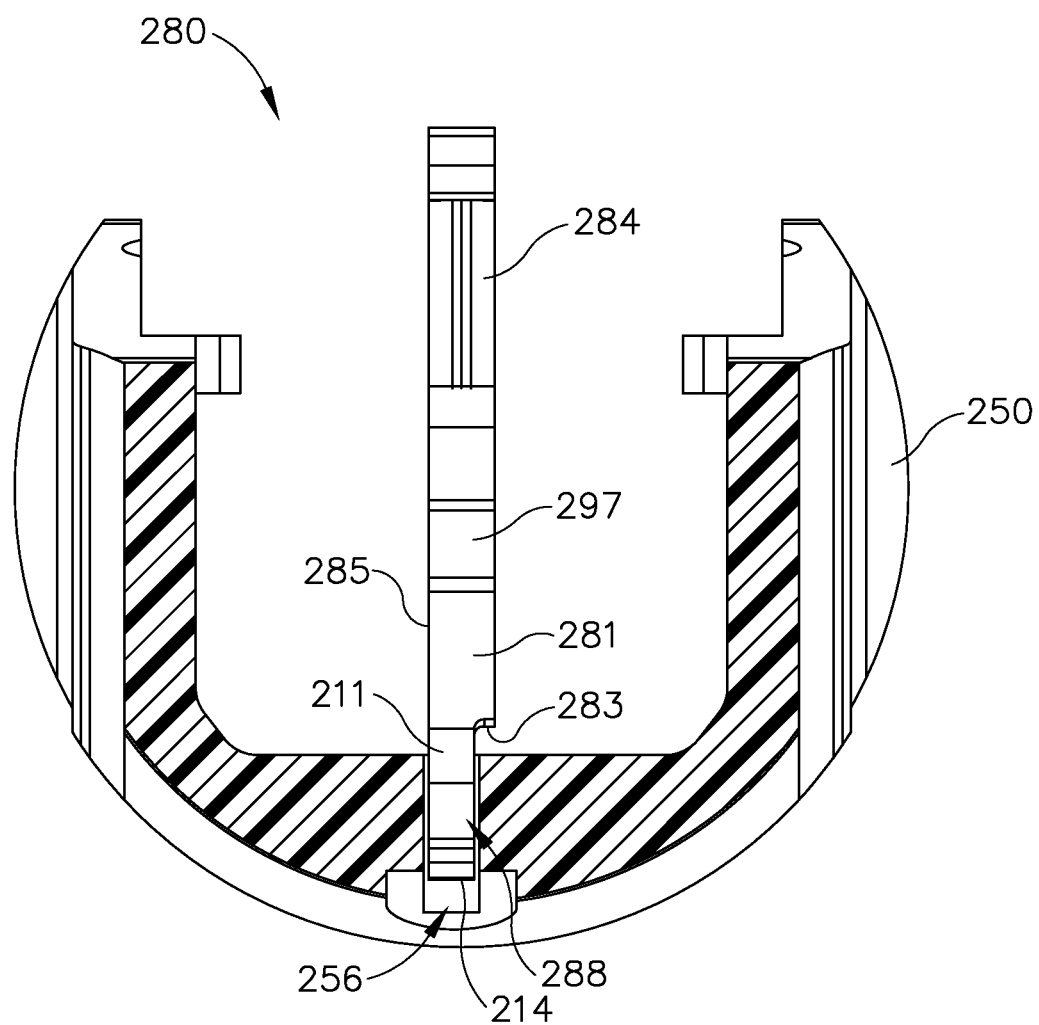
FIG. 17 depicts an end view of the blade of FIG. 14 positioned in a slot of the stationary jaw of FIG. 16.

A protrusion (288) extends downwardly from lower extension (285) and is configured to translate within a slot (256) of lower jaw (250). Protrusion (288) is not as wide as lower extension (285) such that a shelf (283) is formed between protrusion (288) and lower extension (285) on a bottom surface of lower extension (285). Accordingly, shelf (283) retains knife member (280) in a vertical position within slot (256) of lower jaw (250), as best seen in FIG. 17. Shelf (283) creates a retention method without the need for added or extended portions beyond the overall thickness of knife member (280). Protrusion (288) comprises a ramped wall (211) sloping toward wall (212). Wall (212) extends proximally to wall (218), which ramps downwardly to wall (214). Wall (214) extends proximally to wall (215) that ramps upwardly to lower extension (285). Walls (218, 214, 215) form tab (289) that extends downwardly from protrusion (288).

Figure 16:
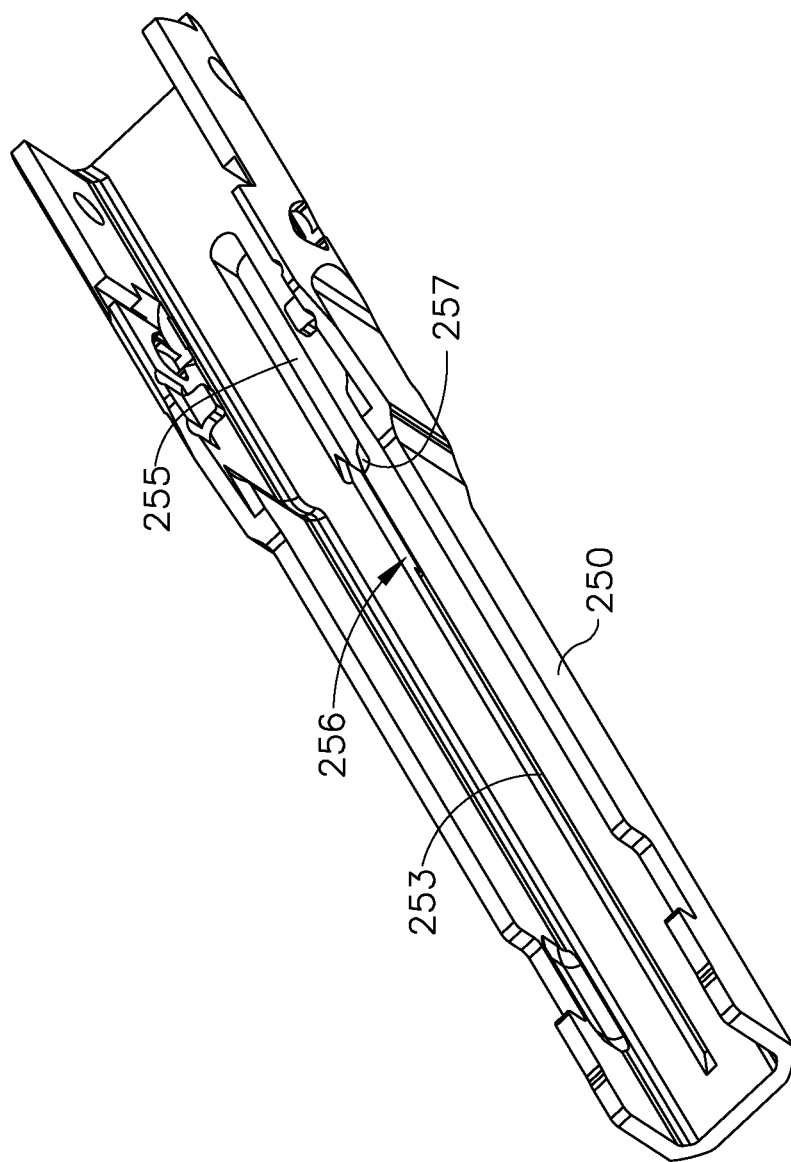
FIG. 16 depicts a perspective view of an exemplary stationary jaw of the end effector of FIG. 13.

Knife member (280) is configured to translate proximally and/or distally within lower jaw (250), based on the actuation of firing trigger (26) to drive motor (102) and firing beam (282). As shown in FIG. 16, lower jaw (250) comprises a slot (256) with a proximal portion (255) and a distal portion (253). Proximal portion (255) is wider than distal portion (253). Proximal portion (255) transitions to distal portion (253) via camming surface (257). FIG. 17 shows knife member (280) positioned within slot (256) of lower jaw (250) when knife member (280) is at a proximal, unfired position. Slot (256) receives protrusion (288) of knife member (280) such that protrusion (288) translates within slot (256) of lower jaw (250). Lower extension (285) is positioned above slot (256). Distal portion (253) of slot (256) has a lateral width sized to correspond to the lateral width of protrusion (288) such that shelf (283) extends laterally past distal portion (253) of slot (256) to maintain the vertical alignment or position of knife member (280) when knife member (280) is positioned within distal portion (253) of slot (256). Proximal portion (255) of slot (256) has a lateral width sized to correspond to the lateral width of lower extension (285) of knife member (280) such that protrusion (288) and lower extension (285) may fall within proximal portion (255) of slot (256) if knife member (280) is advanced without a loaded staple cartridge (270).

Figure 22:
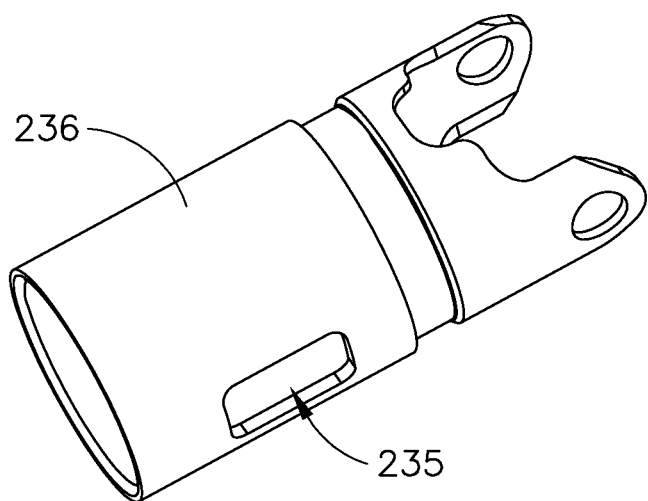
FIG. 22 depicts a perspective view of an exemplary closure ring of the end effector of FIG. 13.

Slot (256) extends continuously within lower jaw (250) to allow for the visualization of the position of knife member (280) within lower jaw (250) as knife member (280) translates proximally and/or distally. Closure ring (236) is coupled to lower jaw (250) to further allow for visualization of knife member (280). In the present example, closure ring (236) comprises an opening (235), as shown in FIG. 22. Closure ring (236) is slidably coupled with lower jaw (250) such that opening (235) is adjacent to proximal portion (255) of slot (256) when closure ring (236) is advanced to a distal position to close anvil (260) against lower jaw (250). Opening (235) is sized to correspond to tab (289) of knife member (280) such that closure ring (236) allows for visualization of tab (289) if protrusion (288) and lower extension (285) fall within proximal portion (255) of slot (256).

Figure 18:
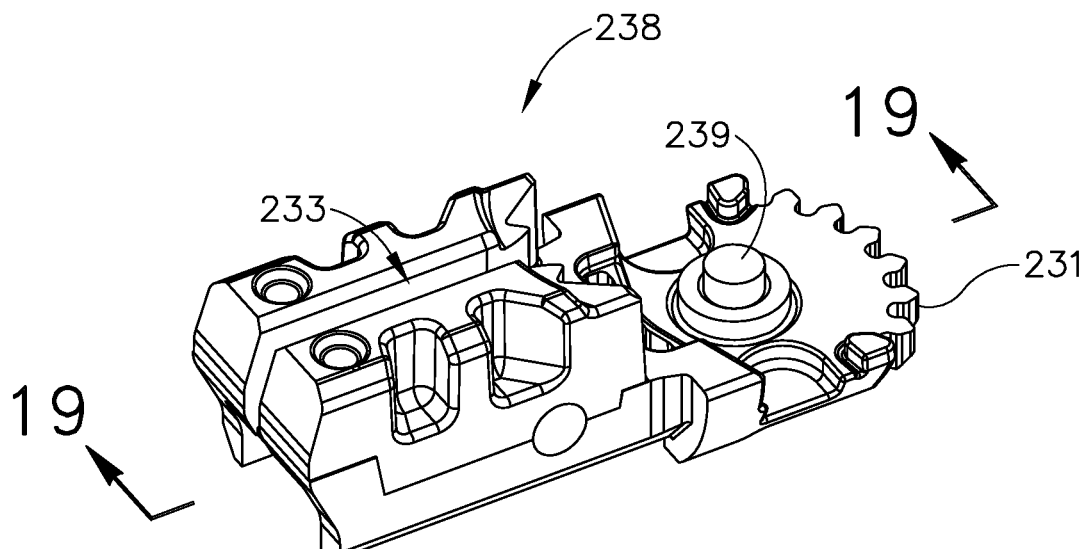
FIG. 18 depicts a perspective view of an exemplary lockout feature of the end effector of FIG. 13.
Figure 19:
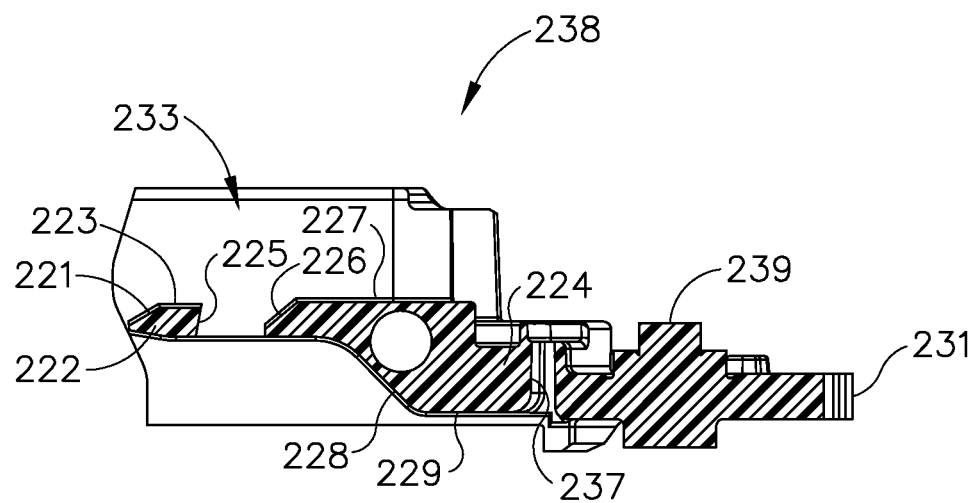
FIG. 19 depicts a cross sectional view of the lockout of feature of FIG. 18 taken along line 19-19 of FIG. 18.
Figure 23A:
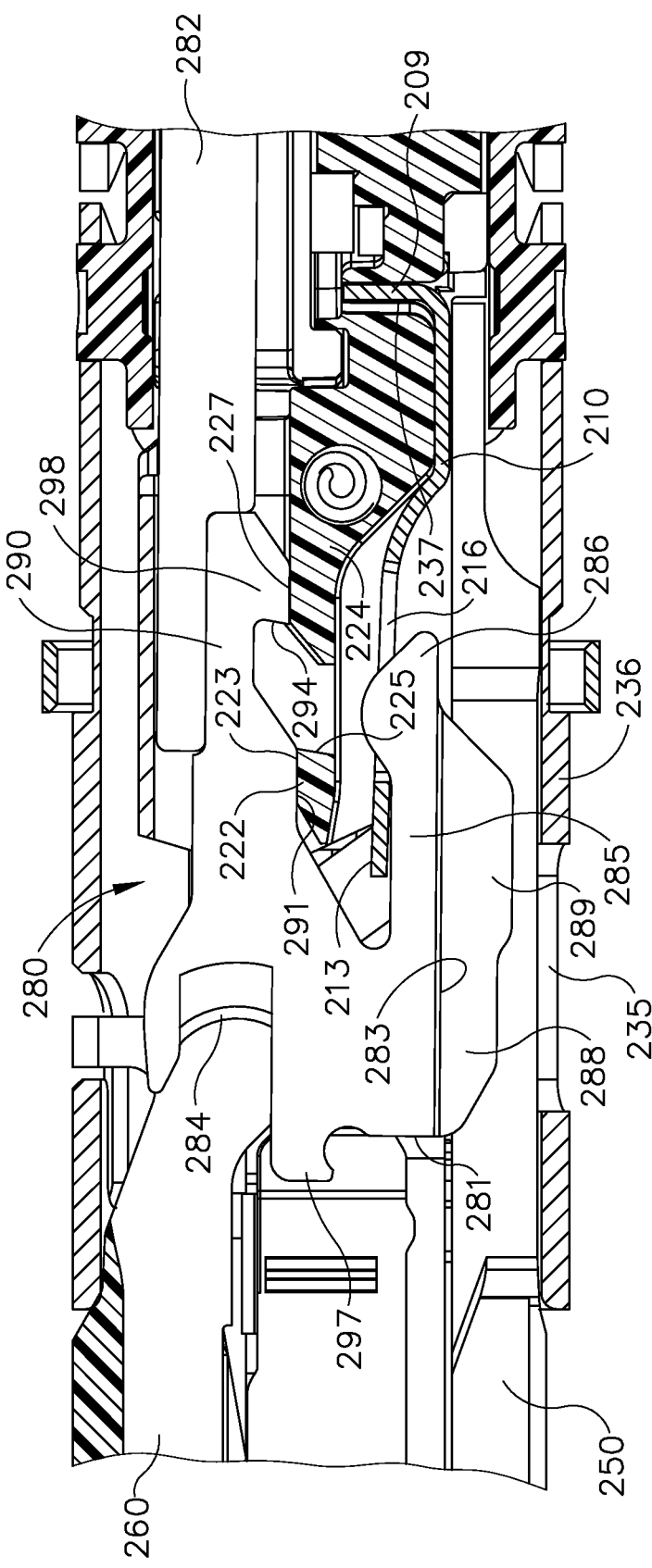
FIG. 23A depicts a side cross sectional view of the end effector of FIG. 13 in an initial position.

The proximal end of lower jaw (250) is coupled with frame member (238), shown in FIGS. 18-19. Frame member (238) comprises a channel (233), a pivot (239), and gear (231). A first engagement feature (222) and a second engagement feature (224) are positioned within channel (233), as shown in FIG. 19. Engagement features (222, 224) are configured to engage upper extension (290) of knife member (280). First engagement feature (222) comprises a wall (225) extending upwardly within channel (233). Wall (225) transitions to wall (223), which extends distally to wall (221). Wall (221) slopes downwardly in the distal direction. Second engagement feature (224) is proximal to first engagement feature (222). The top surface of second engagement feature (224) comprises a wall (227) extending distally to wall (226), which slopes downwardly in the distal direction. The bottom surface of second engagement feature (224) comprises a wall (228) sloping downwardly in the proximal direction to wall (229). Wall (229) extends proximally to wall (237), which extends upwardly from wall (229). The bottom surface of second engagement feature (224) is configured to engage resilient member (210), as shown in FIG. 23A. Gear (231) has teeth and is proximal to engagement feature (224). Pivot (239) extends upwardly from gear (231). Pivot (239) and gear (231) are configured to rotatably couple with articulation section (234) of shaft assembly (220) to allow end effector (240) to pivot to a desired angle (a) relative to shaft assembly (220). By way of example only, gear (231) and/or other features of articulation section (234) may be constructed in accordance with at least some of the teachings of U.S. patent application Ser. No. 13/780,067, entitled "Surgical Instrument End Effector Articulation Drive with Pinion and Opposing Racks," filed Feb. 28, 2013, now U.S. Pat. No. 9,186,142, issued Nov. 17, 2015, the disclosure of which is incorporated by reference herein; and/or U.S. application Ser. No. 13/780,162, entitled "Surgical Instrument with Articulation Lock Having a Detenting Binary Spring," filed Feb. 28, 2013, now U.S. Pat. No. 9,867,615, issued Jan. 16, 2018, the disclosure of which is incorporated by reference herein.

Figure 20:
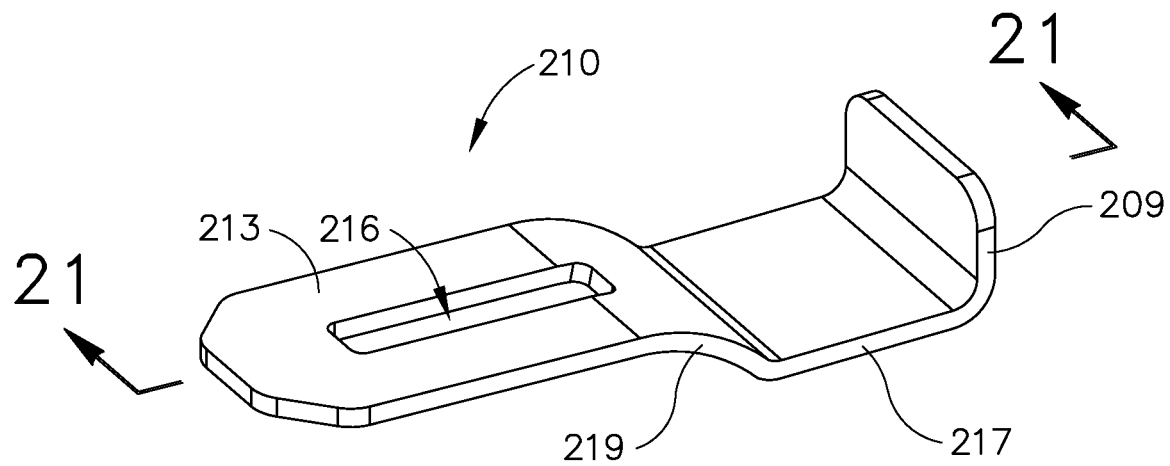
FIG. 20 depicts a perspective view of an exemplary spring of the end effector of FIG. 13.
Figure 21:
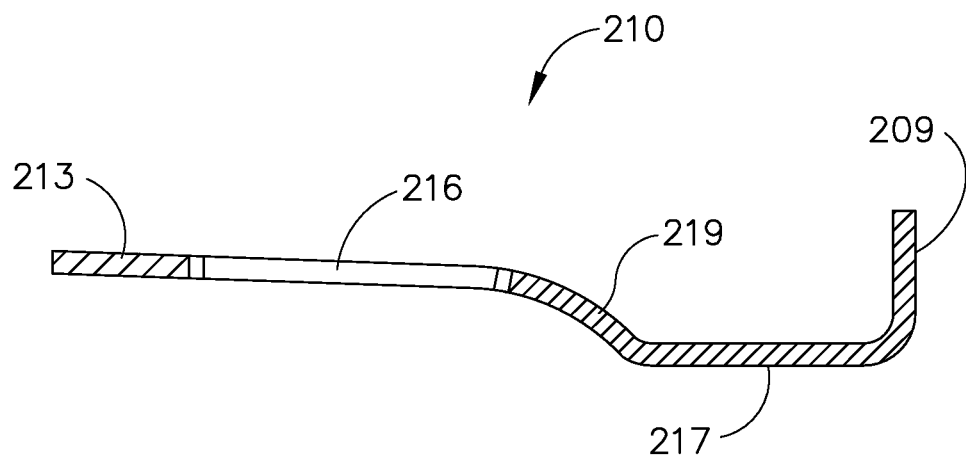
FIG. 21 depicts a cross sectional view of the spring of FIG. 20 taken along line 21-21 of FIG. 20.

FIGS. 20-21 show resilient member (210) in greater detail. Resilient member (210) comprises a distal portion (213) and a proximal portion (285). Distal portion (213) comprises an opening (216) that is configured to receive tab (286) of lower extension (285) of knife member (280). Distal portion (213) transitions to proximal portion (217) via ramped portion (219) that slopes downwardly in the proximal direction. Ramped portion (219) is compliant and is configured to resiliently bias distal portion (282) downwardly. A wall (209) extends upwardly from the proximal end of proximal portion (217). Wall (209) engages wall (237) of frame member (238) such that frame member (238) is configured to axially retain resilient member (210).

A. Exemplary Lockout Sequence

Figure 23B:
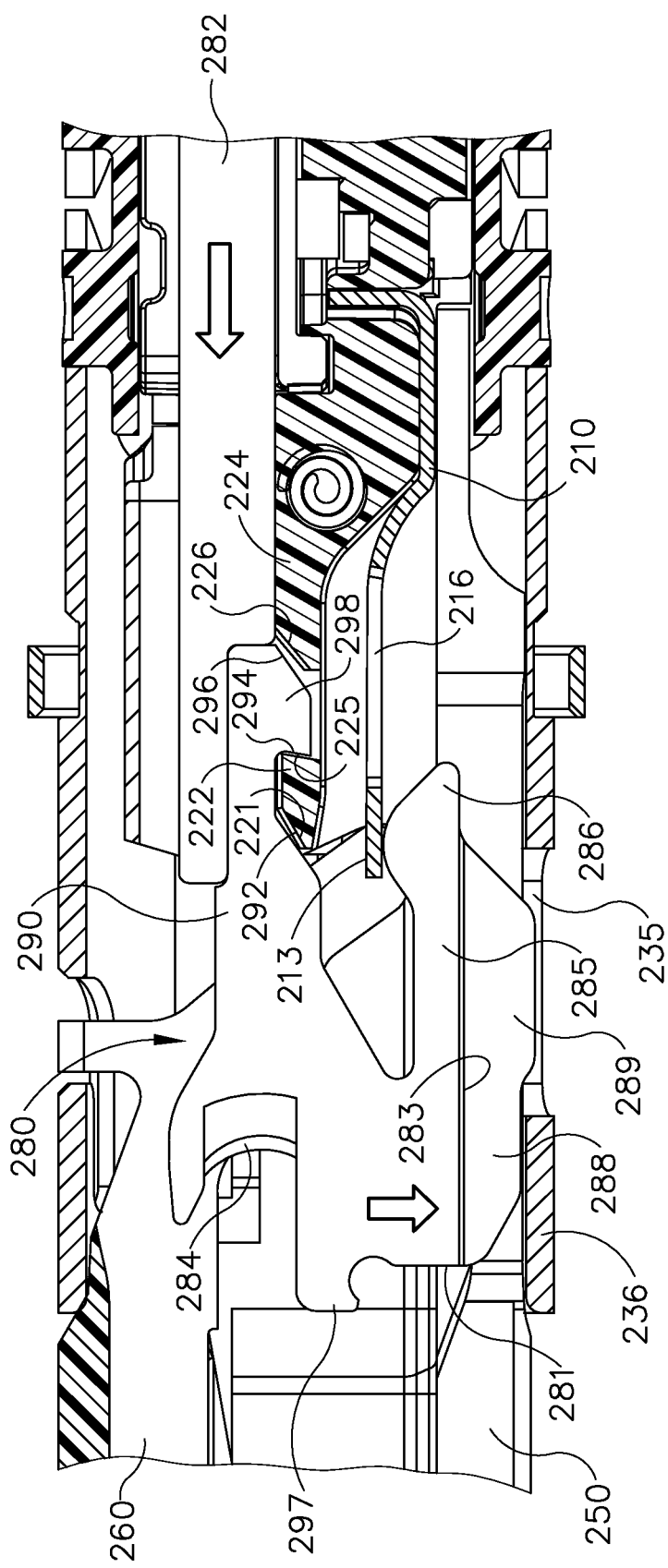
FIG. 23B depicts a side cross sectional view of the end effector of FIG. 13 in a lockout position.

FIGS. 23A-23B show an attempt at firing knife member (280) without a properly loaded staple cartridge (270). For instance, instrument (10) may be inserted to a surgical site in a nonarticulated state, with anvil (260) and lower jaw (250) closed. Once articulation section (234) and end effector (240) are inserted to the desired site within the patient, anvil (260) may be pivoted away from lower jaw (250) to the open end effector (240) such that anvil (260) and lower jaw (250) may be positioned about tissue. Articulation section (234) may be remotely articulated by articulation control knob (35), such that end effector (240) may be deflected to a desired angle (a). Closure trigger (24) may then be actuated toward pistol grip (22) to cause the closing of anvil (260) toward lower jaw (250). Such closing of anvil (260) is provided through a closure tube (32) and closure ring (236), which both longitudinally translate relative to handle portion (20) and lower jaw (250) in response to pivoting of closure trigger (24) relative to pistol grip (22). Articulation section (234) is operable to communicate longitudinal movement from closure tube (32) to closure ring (236).

FIG. 23A shows end effector (240) in an initial position just after anvil (260) and lower jaw (250) are closed, but without staple cartridge (270) in lower jaw (250). In the initial position, upper extension (290) of knife member (280) is positioned above engagement features (222, 224) of frame member (238). Wall (291) of upper extension (290) is resting on wall (223) of first engagement feature (222), while tab (298) of upper extension (290) is resting on wall (227) of second engagement feature (224). Resilient member (210) is positioned between lower jaw (250) and frame member (238). Wall (287) of resilient member (210) is engaged with wall (237) of frame member (238) such that wall (237) is configured to axially retain resilient member (210). Opening (216) of resilient member (210) is positioned above lower extension (285) of knife member (280) such that tab (286) of lower extension (285) is positioned within opening (216) of resilient member (210). Protrusion (288) of lower extension (285) is positioned within proximal portion (255) of slot (256) of lower jaw (250). Protrusion (288) is vertically aligned within slot (256) such that shelf (283) is positioned above slot (256). Accordingly, knife member (280) is ready to be fired in from the initial position.

However, in the present example, a staple cartridge (270) was not properly loaded in end effector (240). Accordingly, distal tip (297) and distal wall (281) are not engaged with a sled (278). When firing trigger (26) is actuated to drive firing beam (282) and knife member (280) distally without a properly loaded staple cartridge (270), knife member (280) falls downwardly within end effector (240) to engage engagement features (222, 224) of frame member (238) to prevent knife member (280) from travelling further distally within lower jaw (250), as shown in FIG. 23B. As knife member (280) is pushed distally without a properly loaded staple cartridge (270), tab (286) of lower extension (285) of knife member (280) translates distally from opening (216) of resilient member (210). Tab (286) then engages distal portion (213) of resilient member (210). Because distal portion (213) of resilient member (210) is biased downwardly, resilient member (210) pushes tab (286) of knife member (280) downward. This causes tab (298) of upper extension (290) of knife member (280) to fall downwardly between engagement features (222, 224). Accordingly, wall (294) of tab (298) engages wall (225) of first engagement feature (222) to prevent knife member (280) from travelling any further distally to lock knife member (280) within end effector (240). It should be understood that the foregoing lockout may also occur when an operator intends to advance firing beam (282) from a proximal position to a distal position when a spent staple cartridge (270) is loaded in end effector. The lockout features thus prevent advancement of firing beam (282) when no staple cartridge (270) is loaded in end effector (240); and when a cartridge (270) that is in end effector (240) has already been fired and firing beam (282) has been retracted back to a proximal position.

Figure 24A:
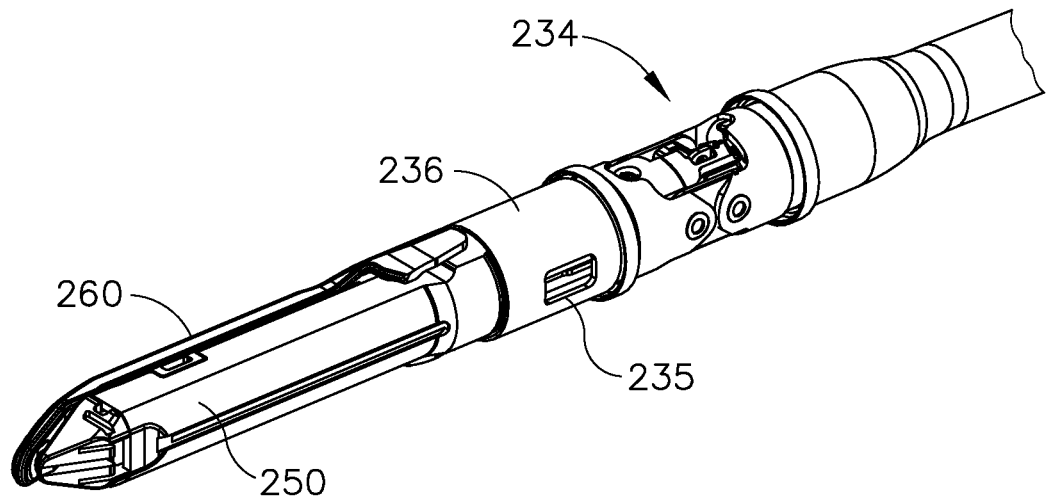
FIG. 24A depicts a bottom perspective view of the end effector of FIG. 13 in the initial position.
Figure 24B:
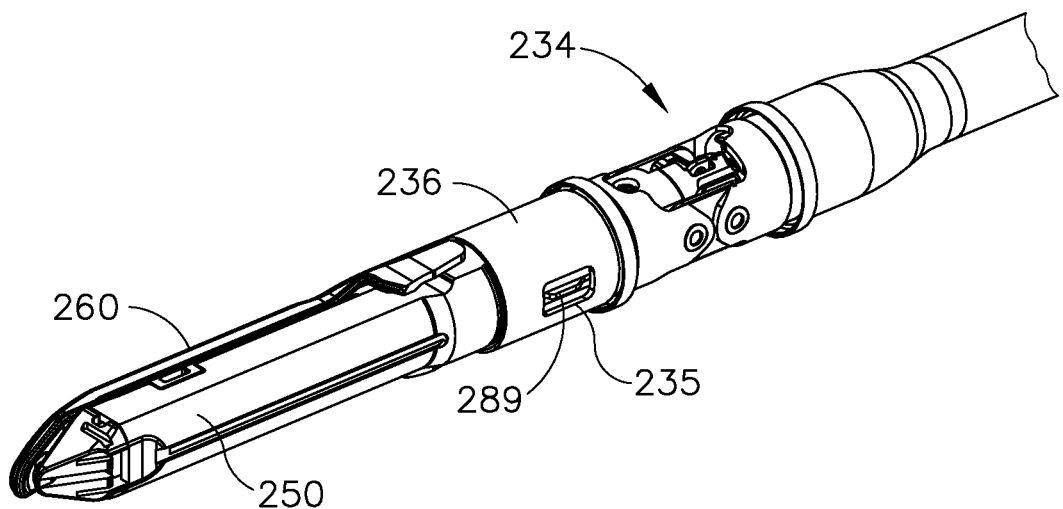
FIG. 24B depicts a bottom perspective view of the end effector of FIG. 13 in the lockout position.

As knife member (280) falls downwardly to the locked position shown in FIG. 23B, lower extension (285) and protrusion (288) of knife member (280) fall within proximal portion (255) of slot (256) of lower jaw (250). Accordingly, tab (289) of protrusion (288) extends through proximal portion (255) of slot (256) and through opening (235) of closure ring (236). This provides a visual indication that knife member (280) is in the lockout position, as shown in FIGS. 24A-24B. In FIG. 24A, knife member (280) is in the initial position such that tab (289) is positioned within slot (256) above opening (235) of closure ring (236). When knife member (280) falls downwardly to the lockout position, as shown in FIG. 24B, tab (289) extends through opening (235) of closure ring (236) to provide a visual indication of lockout. By providing lockout features and visual indications within the space of closure ring (236), the overall length of articulation section (234) may be minimized.

Knife member (280) may be returned to the initial position of FIG. 23A after knife member (280) is in the lockout position of FIG. 23B. For instance, motor (102) may be activated to pull firing beam (282) and knife member (280) proximally to return knife member (280) to the initial position of FIG. 23A. As knife member (280) translates proximally, ramped walls (292, 296) of upper extension (290) of knife member (280) slide proximally against ramped walls (221, 226) of engagement features (222, 224). As upper extension (290) translates proximally against engagement features (222, 224), walls (221, 226) of engagement features (222, 224) push upper extension (290) and knife member (280) upwardly through a camming action. Tab (286) of knife member (280) also travels upwardly to again be positioned within opening (216) of resilient member (210). This returns knife member (280) to the initial position, as shown in FIG. 23A.

B. Exemplary Firing Sequence

FIGS. 25A-25F show knife member (280) being fired with a properly loaded staple cartridge (270). For instance, instrument (10) may be inserted to a surgical site in a nonarticulated state, with anvil (260) and lower jaw (250) closed. Once articulation section (234) and end effector (240) are inserted to the desired site within the patient, anvil (260) may be pivoted away from lower jaw (250) to the open end effector (240) such that anvil (260) and lower jaw (250) may be positioned about tissue. Articulation section (234) may be remotely articulated by articulation control knob (35), such that end effector (240) may be deflected to a desired angle (a). Closure trigger (24) may then be actuated toward pistol grip (22) to cause the closing of anvil (260) toward lower jaw (250). Such closing of anvil is provided through closure tube (32) and closure ring (236), which both longitudinally translate relative to handle portion (20) and lower jaw (250) in response to pivoting of closure trigger (24) relative to pistol grip (22). Articulation section (234) is operable to communicate longitudinal movement from closure tube (32) to closure ring (236).

Figure 25A:
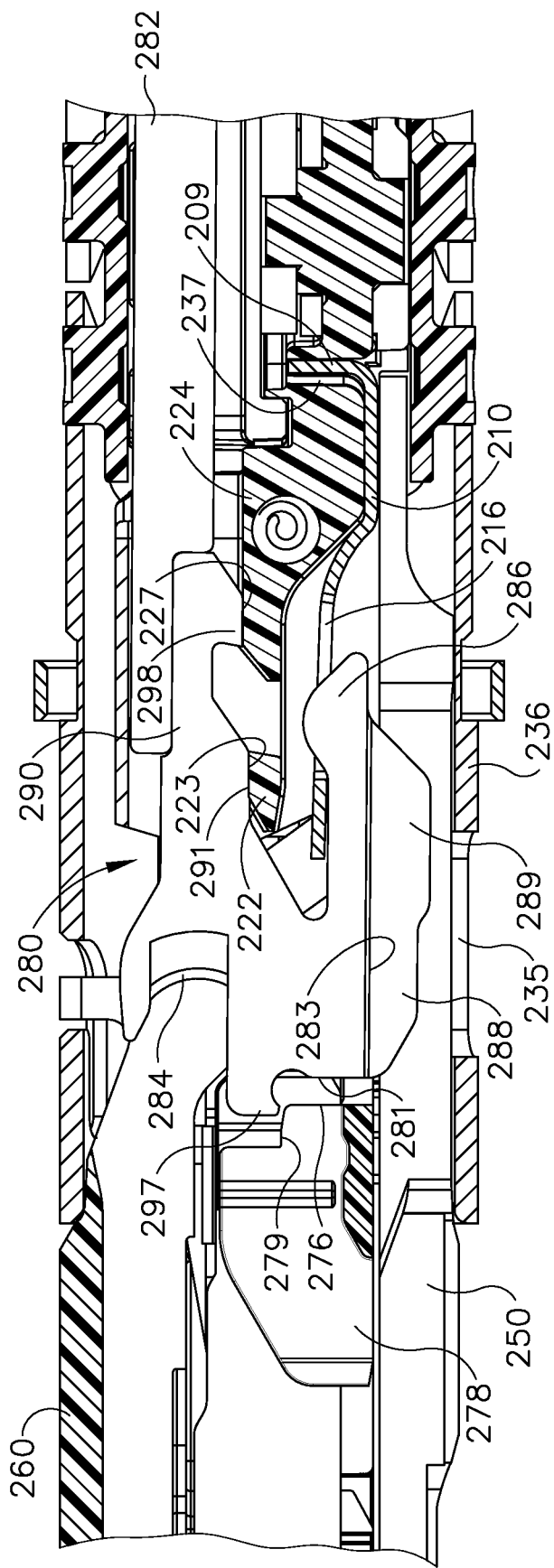
FIG. 25A depicts a side cross sectional view of the end effector of FIG. 13 in the initial position with a loaded cartridge.

FIG. 25A shows end effector (240) in an initial position just after anvil (260) and lower jaw (250) are closed with a properly loaded staple cartridge (270). In the initial position, upper extension (290) of knife member (280) is positioned above engagement features (222, 224) of frame member (238). Wall (291) of upper extension (290) is resting on wall (223) of first engagement feature (222), while tab (298) of upper extension (290) is resting on wall (227) of second engagement feature (224). Resilient member (210) is positioned between lower jaw (250) and frame member (238). Wall (209) of resilient member (210) is engaged with wall (237) of frame member (238) such that wall (237) is configured to axially retain resilient member (210). Opening (216) of resilient member is positioned above lower extension (285) of knife member (280) such that tab (286) of lower extension (285) is positioned within opening (216) of resilient member (210). Protrusion (288) of lower extension (285) is positioned within proximal portion (255) of slot (256) of lower jaw (250). Protrusion (288) is vertically aligned within slot (256) such that shelf (283) is positioned above slot (256). Distal tip (297) of knife member (280) is positioned above sled (278). Accordingly, knife member (280) is ready to be fired in from the initial position shown in FIG. 25A.

Figure 25B:
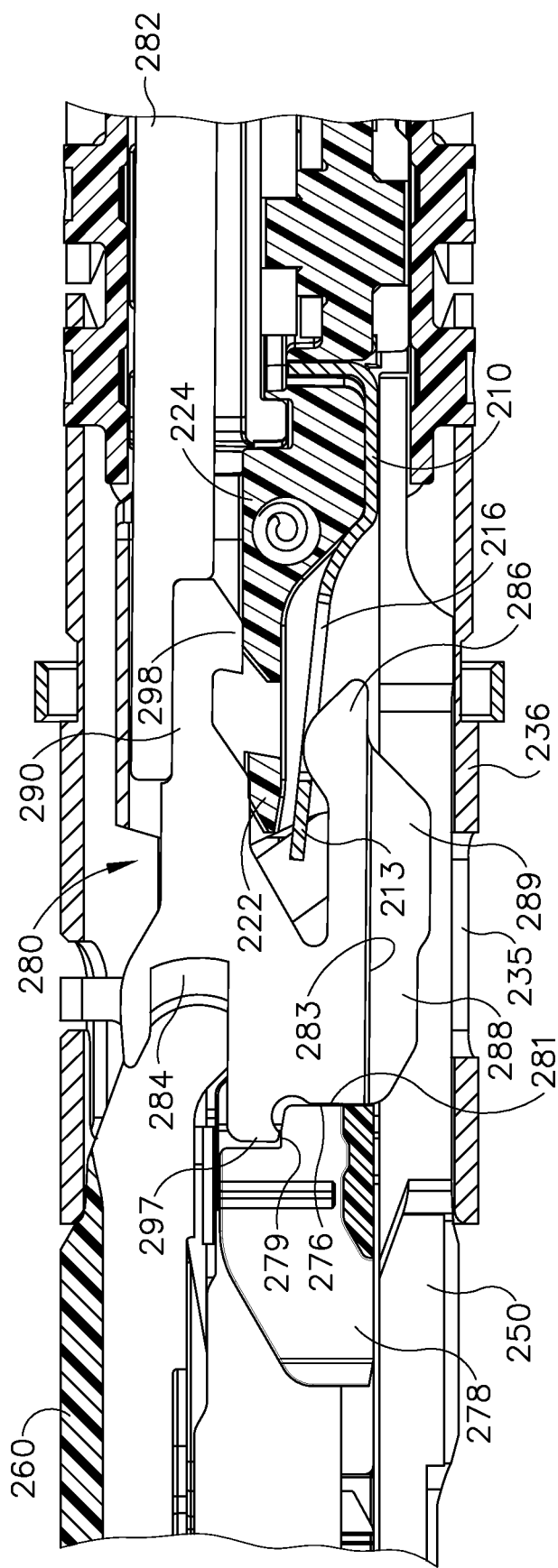
FIG. 25B depicts a side cross sectional view of the end effector of FIG. 13 in a first partially fired position with a loaded cartridge.
Figure 25C:
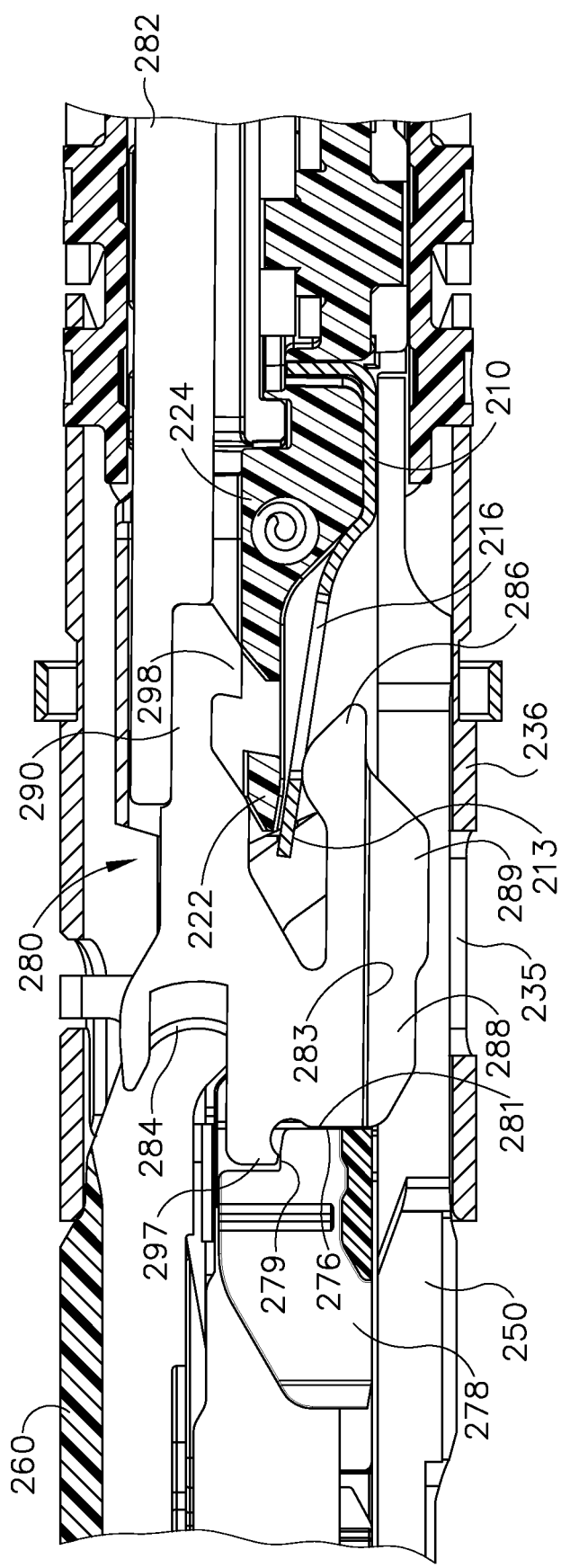
FIG. 25C depicts a side cross sectional view of the end effector of FIG. 13 in a second partially fired position with a loaded cartridge.
Figure 25D:
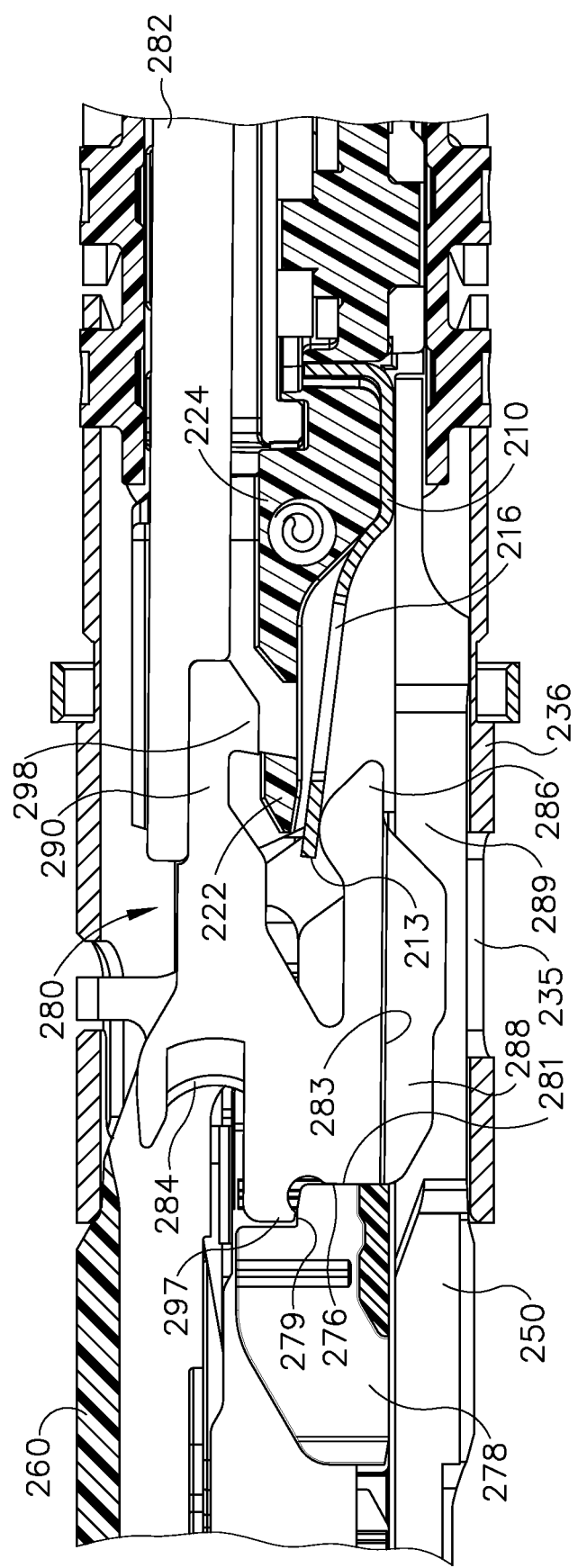
FIG. 25D depicts a side cross sectional view of the end effector of FIG. 13 in a third partially fired position with a loaded cartridge.
Figure 25E:
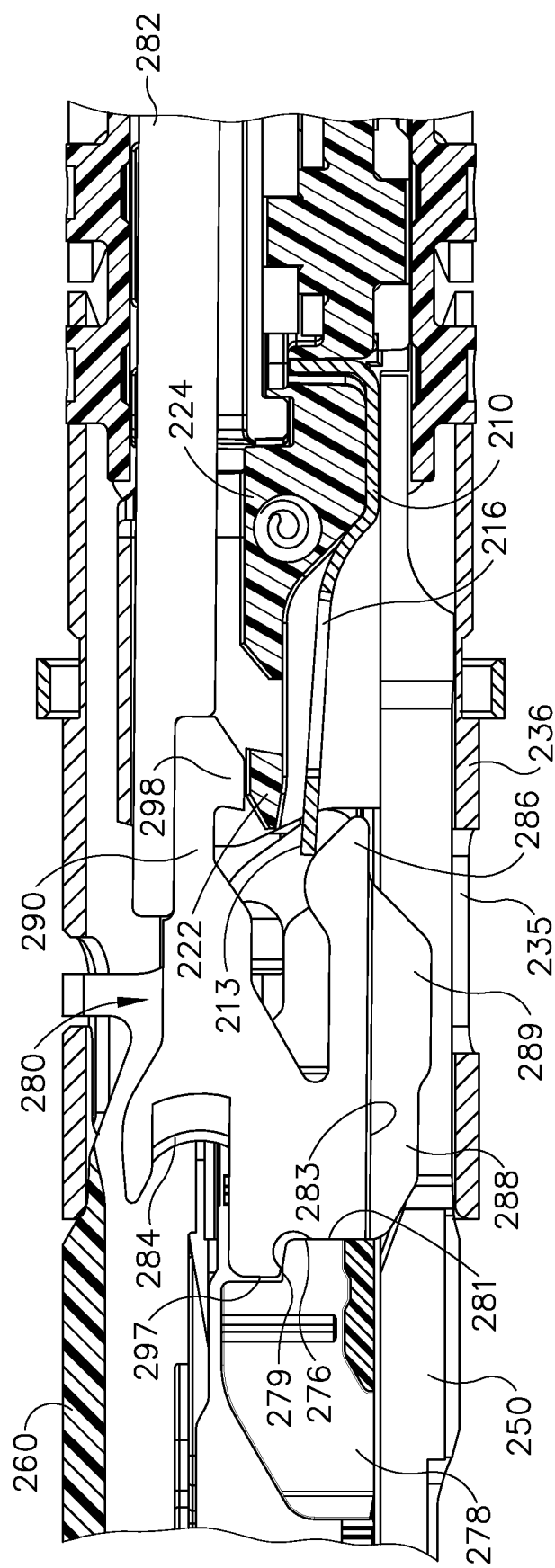
FIG. 25E depicts a side cross sectional view of the end effector of FIG. 13 in a fourth partially fired position with a loaded cartridge.
Figure 25F:
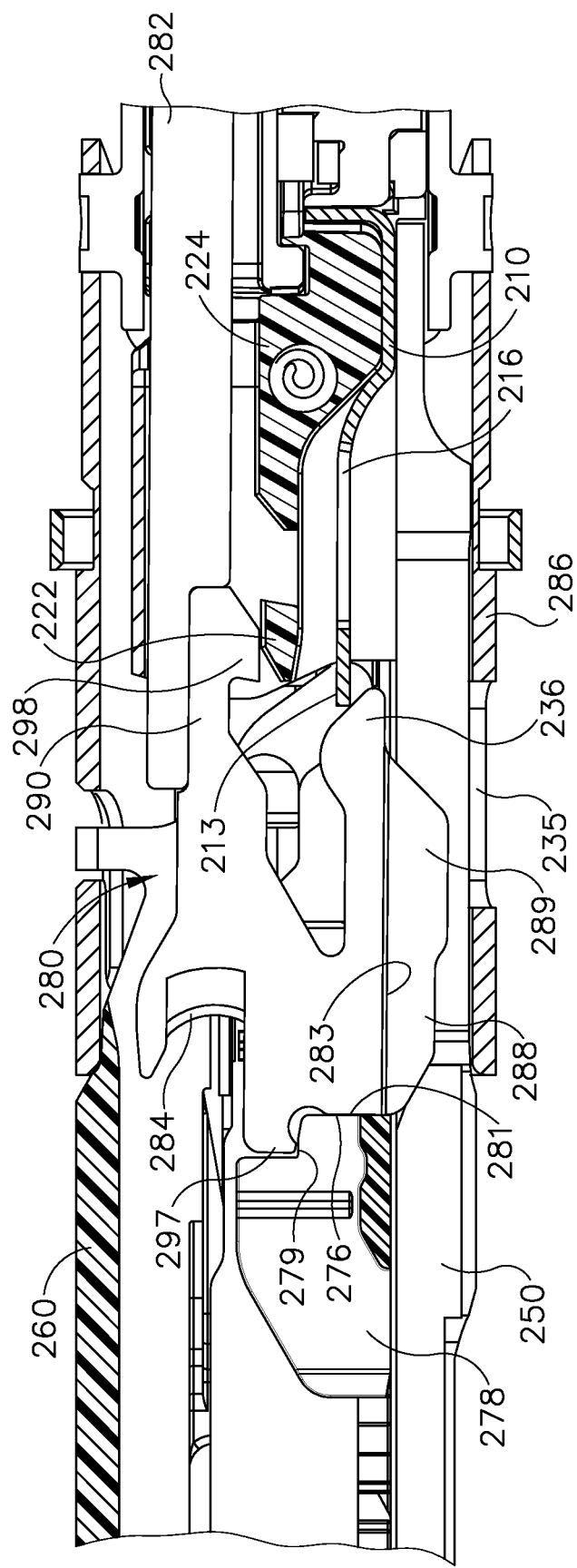
FIG. 25F depicts a side cross sectional view of the end effector of FIG. 13 in a fifth partially fired position with a loaded cartridge.
Figure 26:
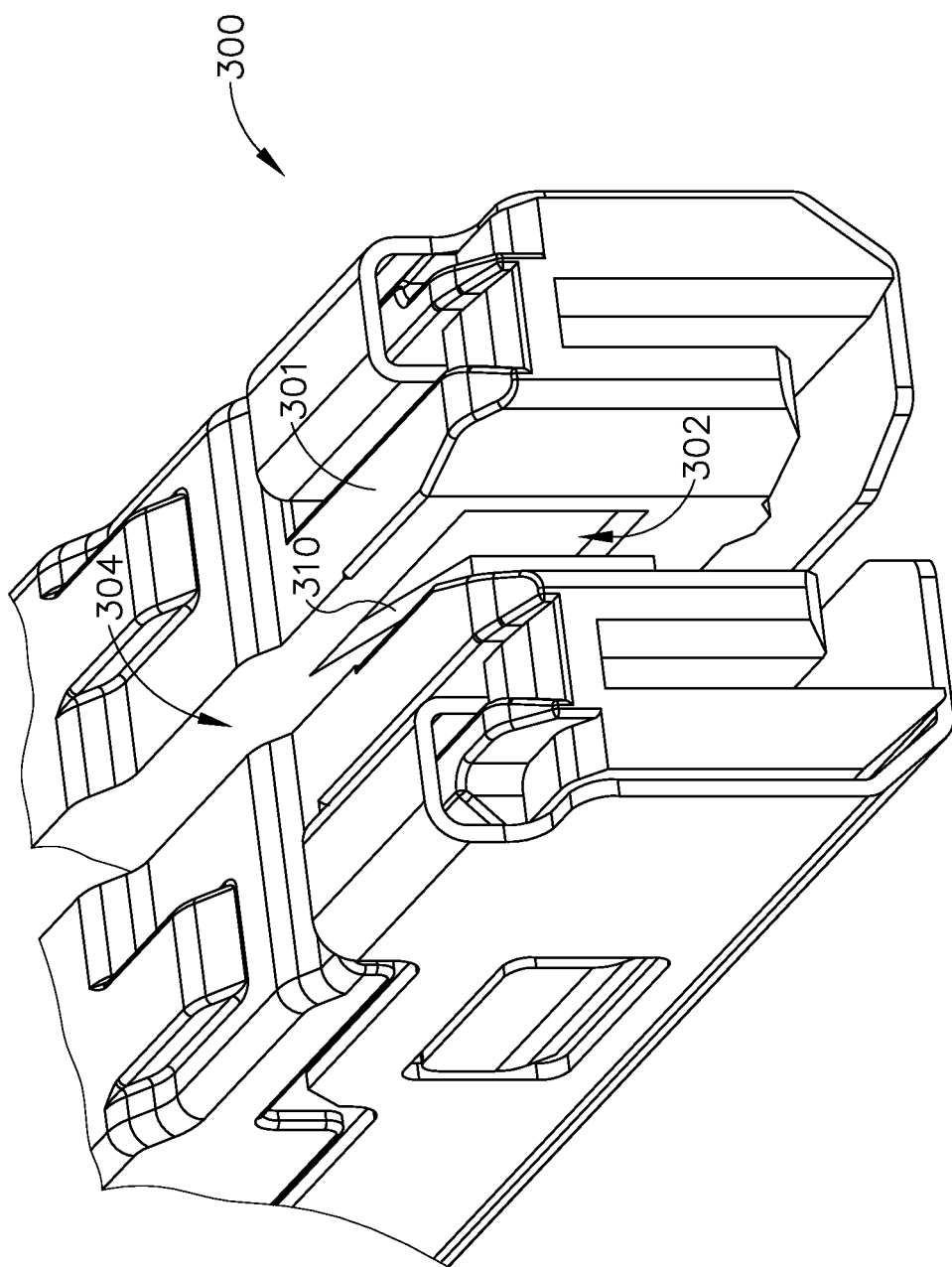
FIG. 26 depicts a perspective view of the proximal end of an exemplary alternative cartridge that may be incorporated into the end effector of FIG. 13.

Firing trigger (26) may be actuated to drive firing beam (282) and knife member (280). As knife member (280) is driven distally, distal tip (297) of knife member (280) engages a top surface (279) of sled (278) and distal wall (281) of knife member (280) engages a proximal end (276) of sled (278), as shown in FIG. 25B. This maintains the vertical position of knife member (280) when knife member is positioned within proximal portion (255) of slot (256) of lower jaw (250). As knife member (280) travels further distally, tab (286) of knife member (280) travels distally from opening (216) of resilient member (210) such that tab (286) engages distal portion (213) of resilient member (210). Tab (286) thereby pushes distal portion (213) of resilient member (210) upwardly, as shown in FIG. 25C. Because sled (278) maintains the vertical position of knife member (280), tab (298) of knife member (280) translates distally above engagement features (222, 224) of frame member (238) such that tab (298) does not fall between engagement features (222, 224) to prevent the distal movement of knife member (280), as shown in FIG. 25D. Knife member (280) thus overrides the lockout position at this stage. Distal portion (213) of resilient member (210) then biases downwardly to a nominal position, proximal of tab (286) of knife member (280), as tab (286) translates distally from resilient member (210), as shown in FIG. 25E. Protrusion (288) of knife member (280) then enters distal portion (253) of slot (256) of lower jaw (250), as shown in FIG. 25F. Shelf (283) of knife member (280) is then positioned above slot (256) and tab (298) of upper extension (290) is above first engagement feature (222). Knife member (280) is then further translated distally to cut and staple tissue positioned between anvil (260) and lower jaw (250).

After knife member (280) is fired distally, knife member (280) may be retracted proximally within lower jaw (250). For example, knife member (280) may be retracted by firing beam (282) by automatic reversal of motor (102) upon detected completion of a firing stroke, in response to a second actuation of firing trigger (26), and/or otherwise. When knife member (280) is retracted, knife member (280) disengages from sled (278). Without sled (280), knife member (280) may fall downwardly to the lockout position of FIG. 23B as knife member (280) is retracted after being fired. Knife member (280) may be returned to the initial position of FIG. 23A after knife member (280) is in the lockout position of FIG. 23B. As knife member (280) is driven proximally by motor (102), ramped walls (292, 296) of upper extension (290) of knife member (280) slide proximally against ramped walls (221, 226) of engagement features (222, 224). As upper extension (290) translates proximally against engagement features (222, 224), walls (221, 226) of engagement features (222, 224) push upper extension (290) and knife member (280) upwardly through a camming action. Tab (286) of knife member (280) also travels upwardly to again be positioned within opening (216) of resilient member (210). This returns knife member (280) to the initial position, as shown in FIG. 23A.

Once tissue positioned between anvil (260) and lower jaw (250) is cut and stapled, end effector (240) may be pivoted back to the nonarticulated position by articulation control knob (35) and removed from the surgical site, with anvil (260) and lower jaw (250) closed. Alternatively, anvil (260) and lower jaw (250) may be opened prior to pivoting end effector (240) to release any tissue between anvil (260) and lower jaw (250). Anvil (260) and lower jaw (250) may then be re-closed prior to removing end effector (240) from the surgical site. End effector (240) may then be opened to replace staple cartridge (270) with a new staple cartridge. To open end effector (240), closure trigger (24) may be released away from pistol grip (22). Staple cartridge (270) may be replaced with a new staple cartridge, and end effector (240) may be again inserted to the surgical site for further cutting and stapling.

In some variations, frame member (238) and knife member (280) are reconfigured such that wall (225) and wall (294) are located at or near the underside of the distal end of knife member (280). For instance, frame member (238) may include a feature that is substantially identical to first engagement feature (222) that is located near protrusion (288) of lower extension (285); and protrusion (288) of lower extension (285) may include a feature that is substantially identical to tab (298). Other suitable locations in which functional equivalents of walls (225, 294) may engage to provide a lockout against distal translation of knife member (280) will be apparent to those of ordinary skill in the art in view of the teachings herein.

III. EXEMPLARY ALTERNATIVE SPENT CARTRIDGE LOCKOUT FEATURES

In some instances, it may be desirable to provide features that prevent knife member (280) from being fired through the same staple cartridge (270) more than once, such that knife member (280) may not be fired through a "spent" staple cartridge (270). For example, such a feature may prevent knife member (280) from engaging the lockout features (222, 224) of frame member (238) discussed above upon being fired through a staple cartridge (270) a first time. However, upon subsequent attempts to fire knife member (280) such a feature would provide engagement between knife member (280) and lockout features (222, 224) of frame member (238) to thereby prevent firing of knife member (280) through the same staple cartridge (270) a second time. The examples below include several merely illustrative versions of spent staple cartridge (270) lockout features that may be readily introduced to an end effector such as end effector (240).

A. Exemplary Cartridge with Resilient Tab

Figure 27:
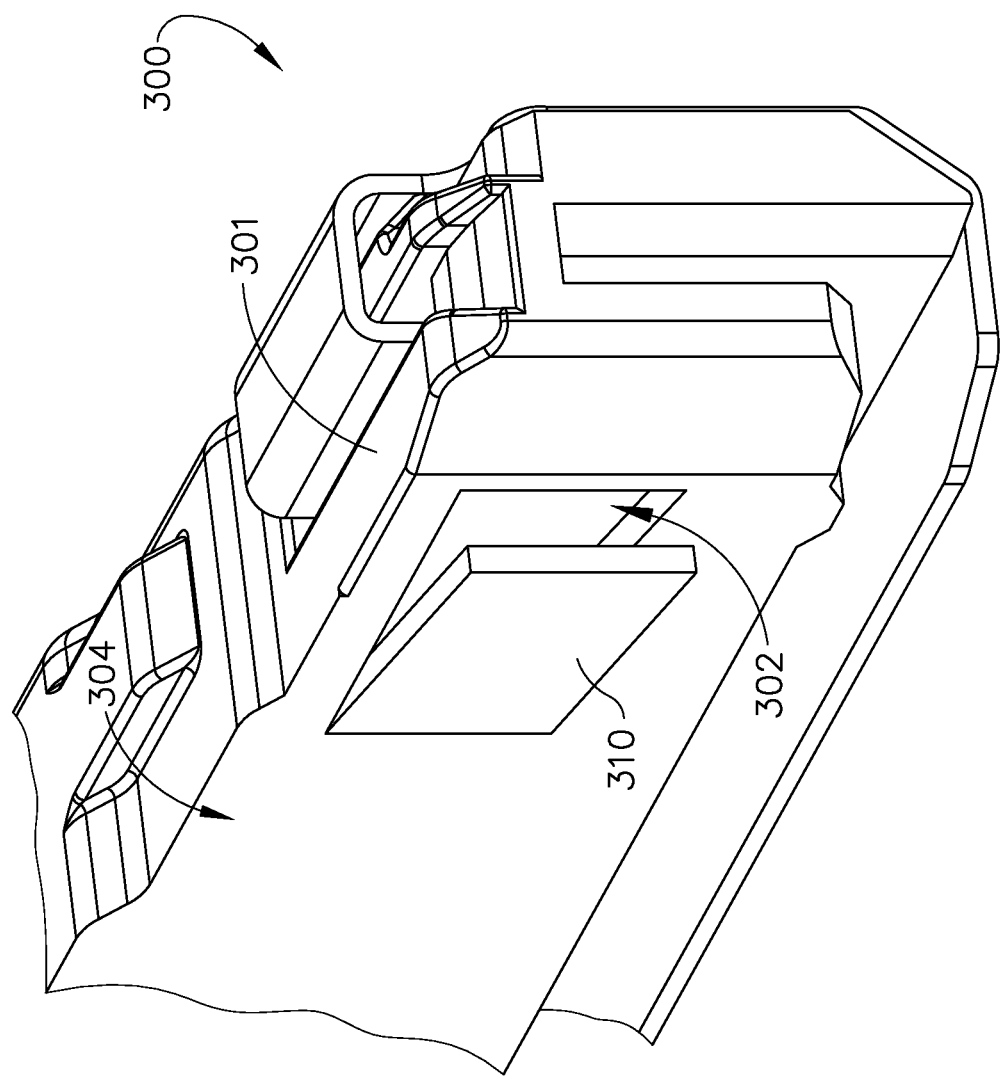
FIG. 27 depicts a cross-sectional perspective view of the proximal end of the cartridge of FIG. 26.

FIGS. 26-29D show an exemplary cartridge (300) having a spent cartridge lockout feature. It should be understood that cartridge (300) may be readily used in end effector (240) or in other end effectors. Cartridge (300) of the present example is configured to operate substantially similar to cartridges (70, 270) discussed above except for the differences discussed below. Cartridge (300) includes a cartridge body (301) having a longitudinal channel (304) through which wedge sled (278) and knife member (280) may be longitudinally translated. The spent cartridge lockout feature of the present example comprises a resilient tab (310). As best seen in FIG. 27, an interior surface of channel (304) of cartridge body (301) comprises a rectangular recess (302) within which resilient tab (310) is pivotably disposed. Resilient tab (310) is pivotably secured within rectangular recess (302) via a living hinge. Resilient tab (310) is pivotable between an unexposed position, in which resilient tab (310) is substantially completely disposed within rectangular recess (302); and an exposed position, in which resilient tab (310) extends from rectangular recess (302) into channel (304) and thus in the pathway of the distally translating knife member (280). Resilient tab (310) of the present example is biased toward the exposed position shown in FIGS. 26-27 and 29D. Resilient tab (310) is configured to allow for firing of knife member (280) when in the unexposed position and to prevent firing of knife member (280) when in the exposed position.

Figure 28:
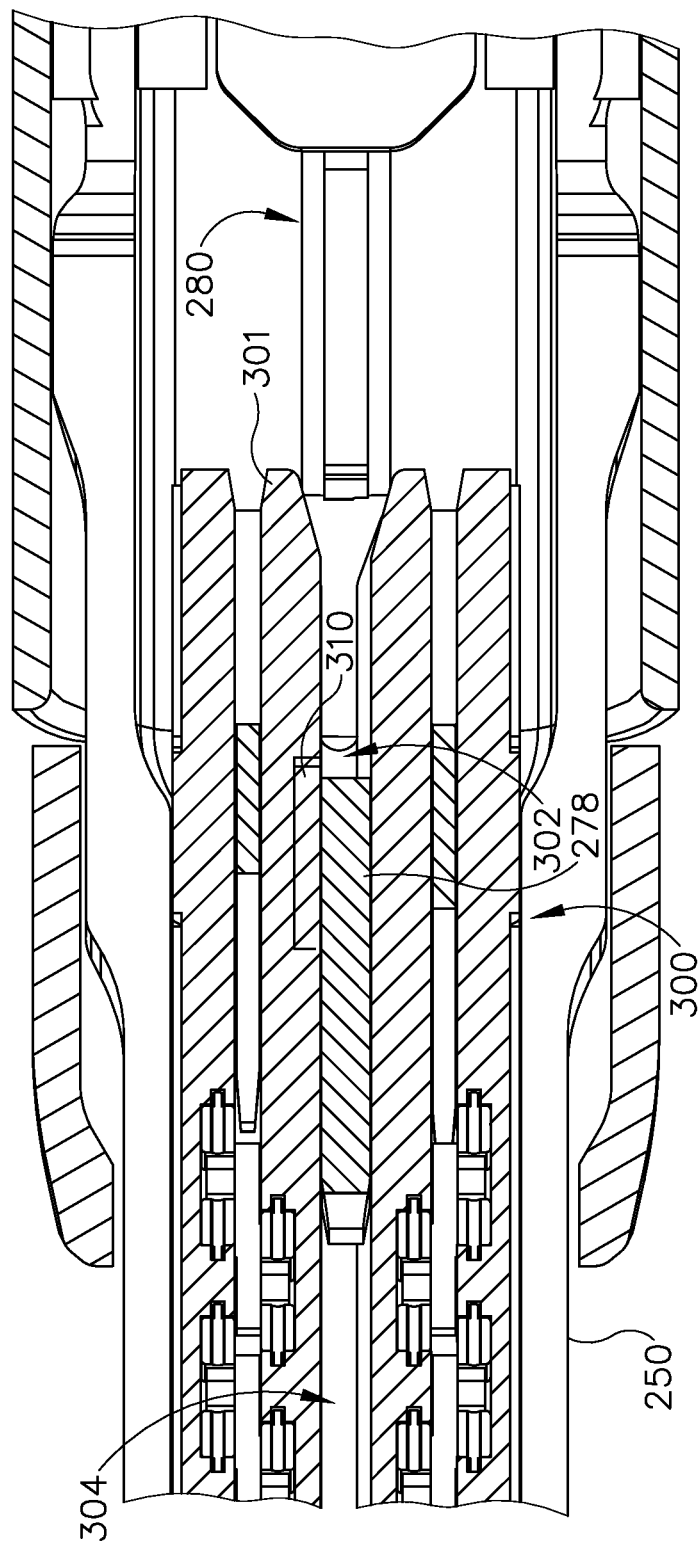
FIG. 28 depicts a cross-sectional top view of the proximal end of the cartridge of FIG. 26.
Figure 29A:
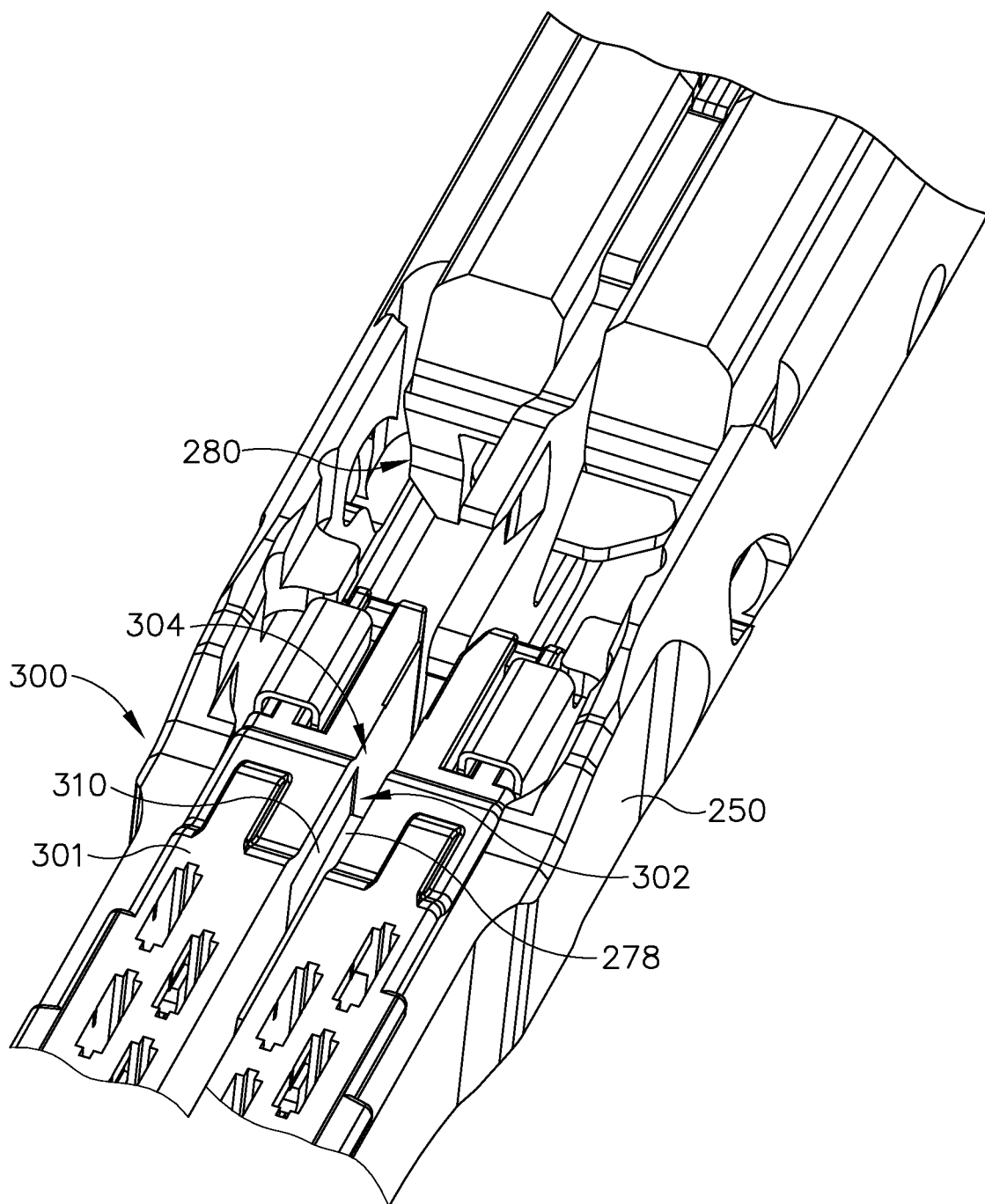
FIG. 29A depicts a perspective view of the proximal end of the cartridge of FIG. 26 engaged with the end effector of FIG. 13, with a resilient tab of the cartridge in a first rotational position, with a sled of the cartridge in a first longitudinal position, and with the knife of the end effector in a first longitudinal position.
Figure 29B:
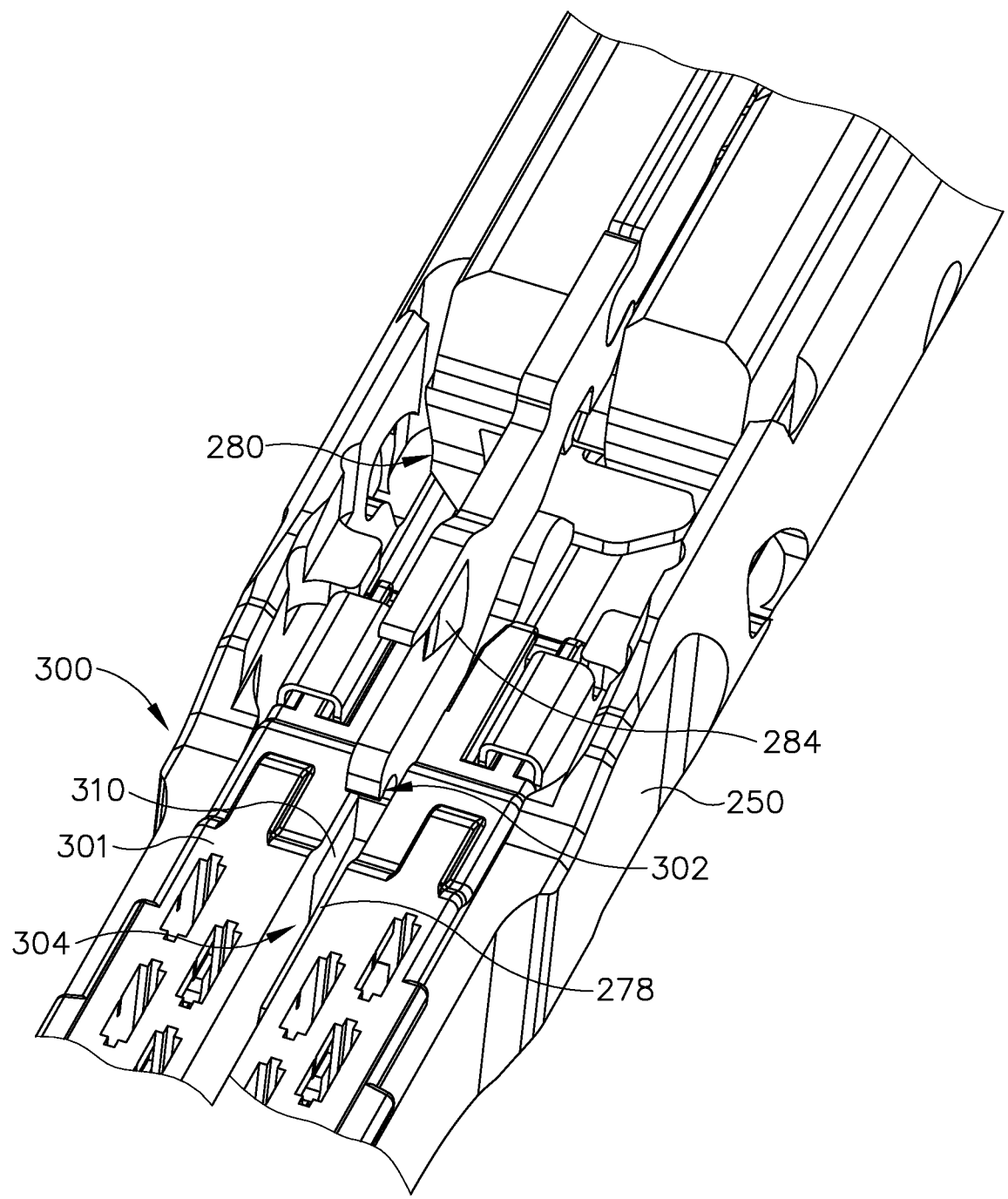
FIG. 29B depicts a perspective view of the proximal end of the cartridge of FIG. 26 engaged with the end effector of FIG. 13, with the resilient tab of the cartridge in the first rotational position, with the sled of the cartridge in the first longitudinal position, and with the knife of the end effector moved into a second longitudinal position.
Figure 29C:
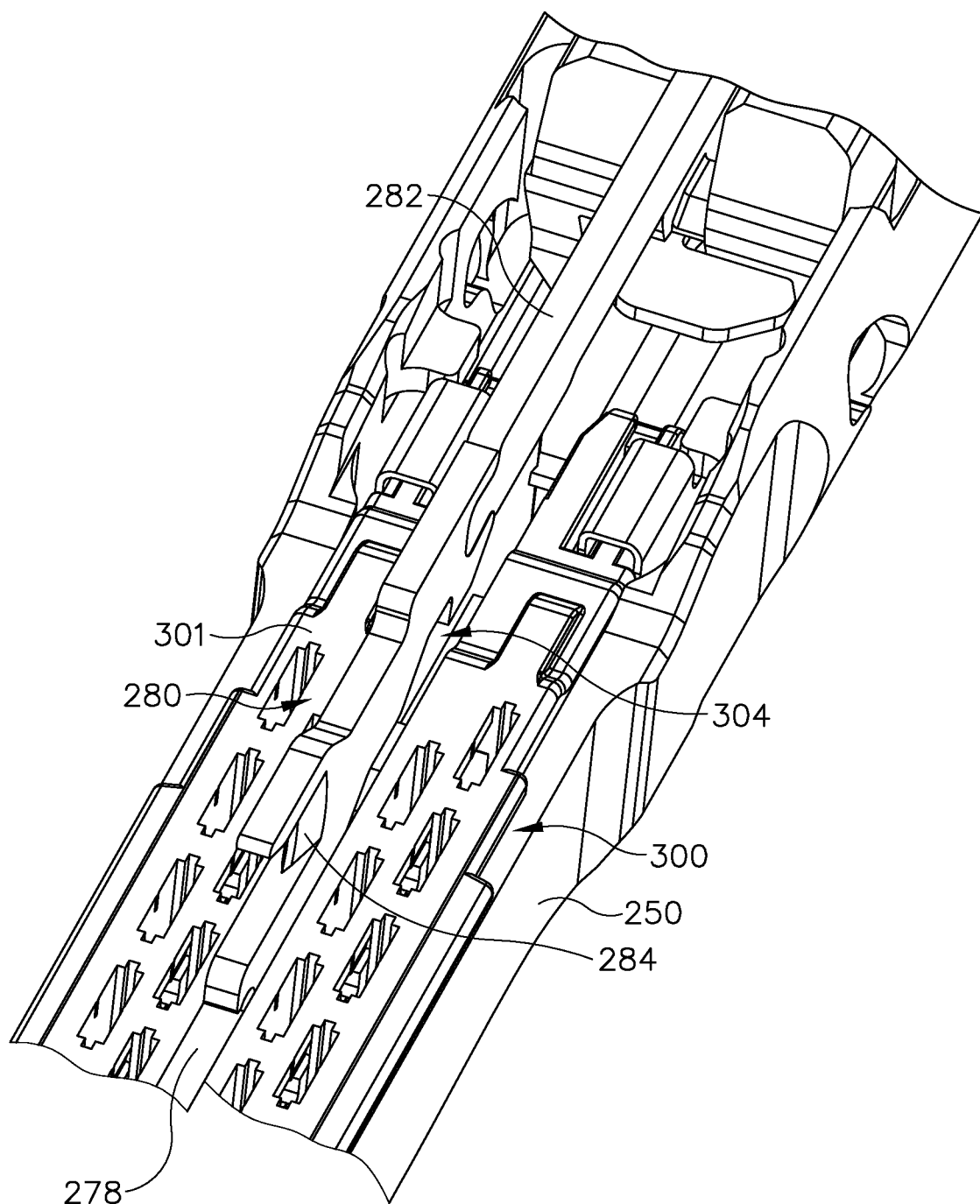
FIG. 29C depicts a perspective view of the proximal end of the cartridge of FIG. 26 engaged with the end effector of FIG. 13, with the resilient tab of the cartridge in the first rotational position, with the sled of the cartridge moved into a second longitudinal position by movement of the knife of the end effector into a third longitudinal position.
Figure 29D:
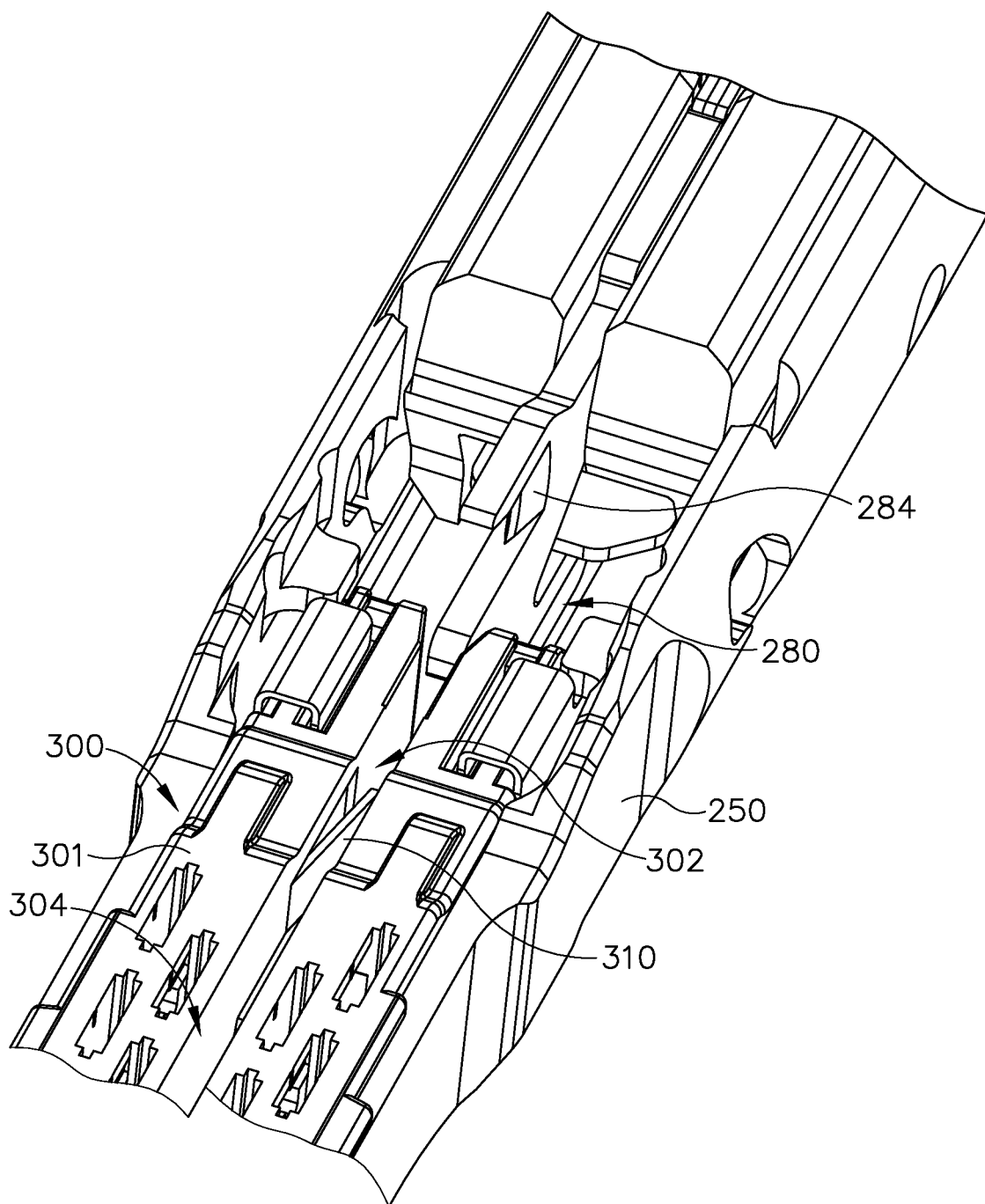
FIG. 29D depicts a perspective view of the proximal end of the cartridge of FIG. 26 engaged with the end effector of FIG. 13, with the resilient tab of the cartridge moved into a second rotational position by movement of the sled of the cartridge into the second longitudinal position and by movement of the knife of the end effector moved back into the first longitudinal position.

As best seen in FIG. 28, wedge sled (278), is positioned within channel (304) of cartridge (300) and is operable to translate longitudinally through channel (304) of cartridge (300). In an initial position (FIGS. 28 and 29A), wedge sled (278) proximally is positioned so as to maintain resilient tab (310) in the unexposed position. As knife member (280) is fired a first time, knife member (280) engages wedge sled (278) (FIG. 29B) and drives wedge sled (278) distally as described above (FIG. 29C). As knife member (280) is being fired, knife member (280) and/or firing beam (282) are configured to maintain resilient tab (310) in the unexposed position. Once knife member (280) is retracted into the initial position, wedge sled (278), knife member (280), and/or firing beam (282) are no longer in a position to maintain resilient tab (310) in the unexposed position such that resilient tab (310) resiliently deflects into the exposed position (FIG. 29D). In the exposed position, resilient tab (310) will engage knife member (280) if the operator attempts to advance knife member (280) distally a second time, thereby preventing firing of knife member (280) a second time through cartridge (300).

B. Exemplary Cartridge with Bypass Beam

FIGS. 30-32E show another exemplary cartridge (320) having a spent cartridge lockout feature. It should be understood that cartridge (320) may be readily used in end effector (240) or in other end effectors. Cartridge (320) of the present example is configured to operate substantially similar to cartridges (70, 270) discussed above except for the differences discussed below. Cartridge (320) includes a cartridge body (322) having a longitudinal channel (324) through which wedge sled (278) and knife member (280) may be longitudinally translated. The spent cartridge lockout feature of the present example comprises a breakaway or cutaway beam (330) extending between opposing interior surfaces of channel (324). Beam (330) is positioned within channel (324) such that beam (330) is in the path of knife member (280). Beam (330) of the present example comprises a square cross-sectional profile, but may comprise any other appropriate shape. As will be discussed in more detail below, as knife member (280) is fired distally through channel (324), knife member (280) is configured to break and/or cut beam (330). Also as will be discussed in more detail below, beam (330) is configured to allow for firing of knife member (280) when beam (330) is present; and to prevent firing of knife member (280) when beam (330) is not present.

Figure 32A:
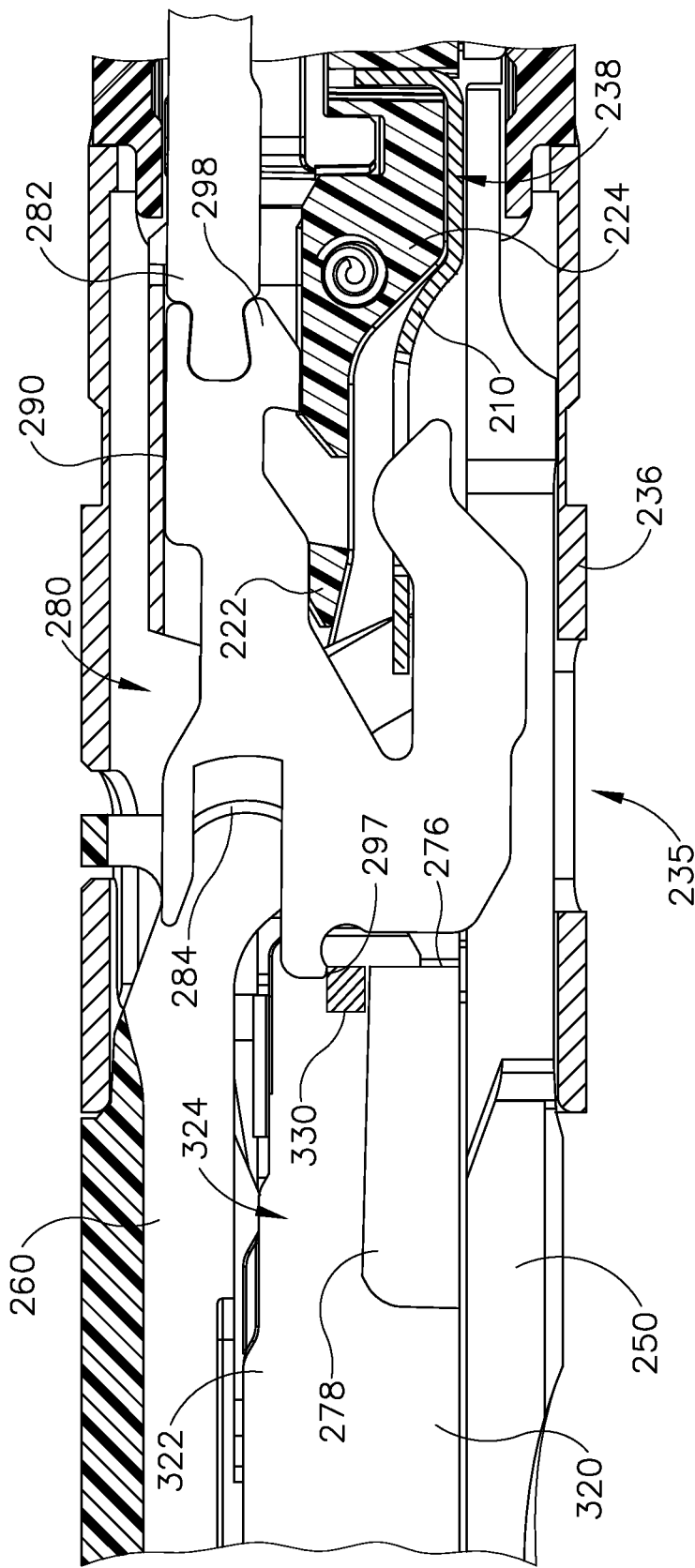
FIG. 32A depicts a cross-sectional view of the proximal end of the cartridge of FIG. 30 disposed within the end effector of FIG. 13, with a sled of the cartridge in a first longitudinal position and with a knife of the end effector in a first longitudinal position.
Figure 32B:
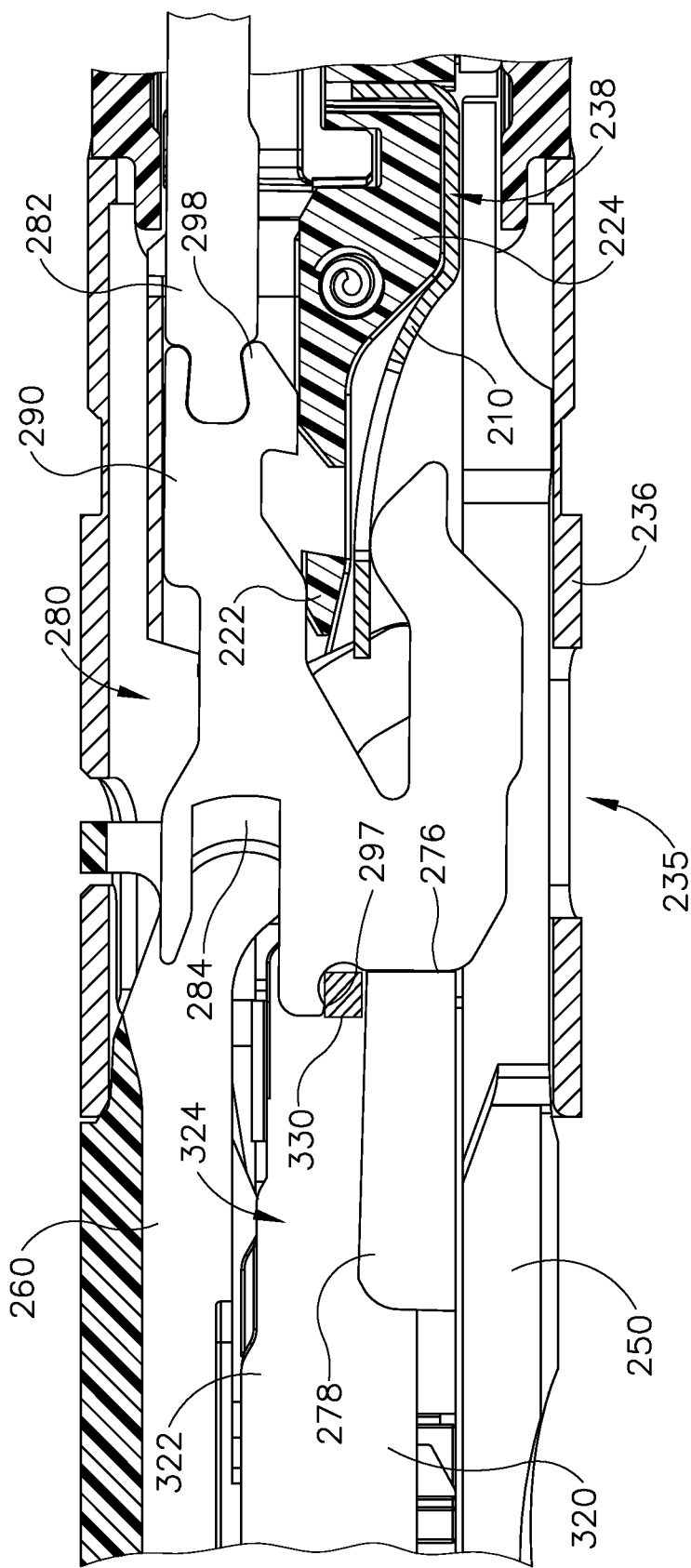
FIG. 32B depicts a cross-sectional view of the proximal end of the cartridge of FIG. 30 disposed within the end effector of FIG. 13, with the sled of the cartridge in the first longitudinal position and with the knife of the end effector moved into a second longitudinal position.
Figure 32C:
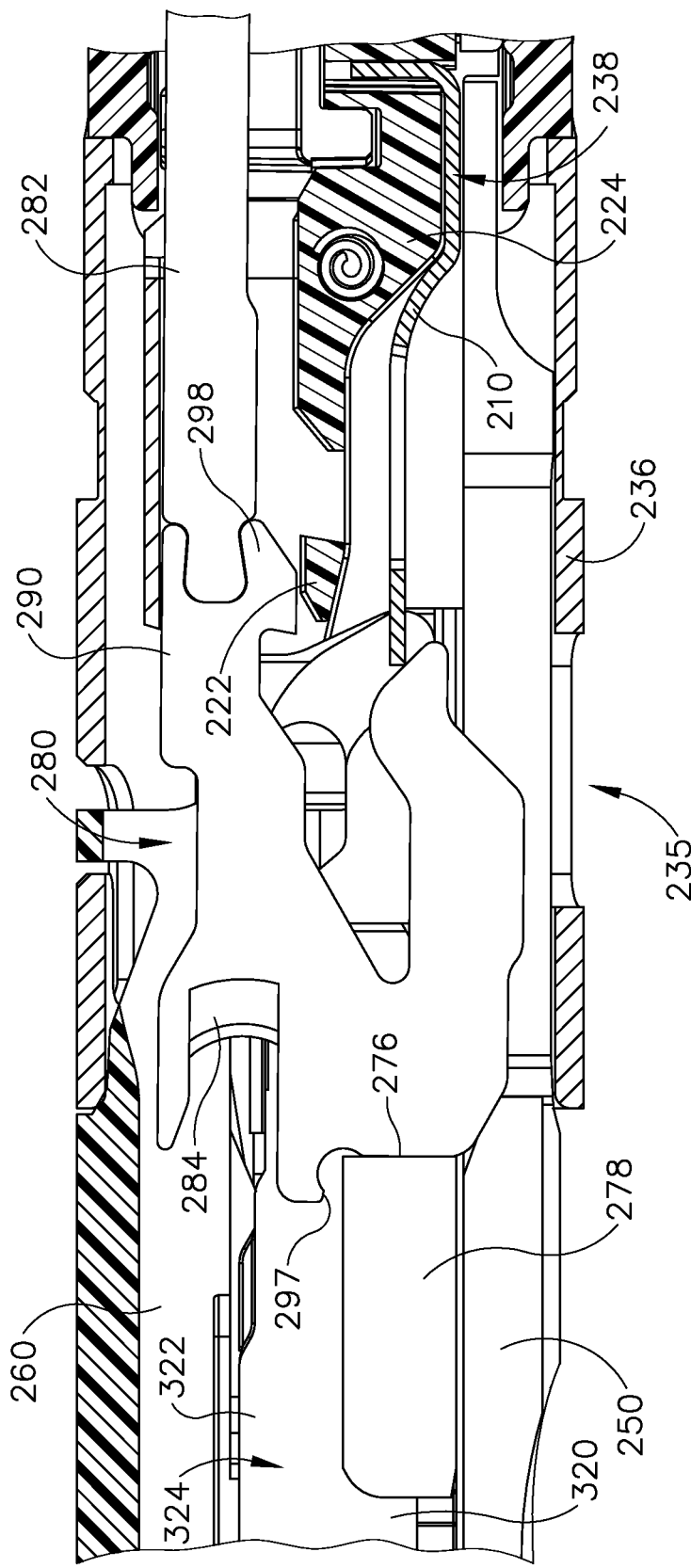
FIG. 32C depicts a cross-sectional view of the proximal end of the cartridge of FIG. 30 disposed within the end effector of FIG. 13, with the sled of the cartridge moved into a second longitudinal position by movement of the knife of the end effector into a third longitudinal position, with the knife breaking through the breakaway feature of the cartridge.
Figure 32D:
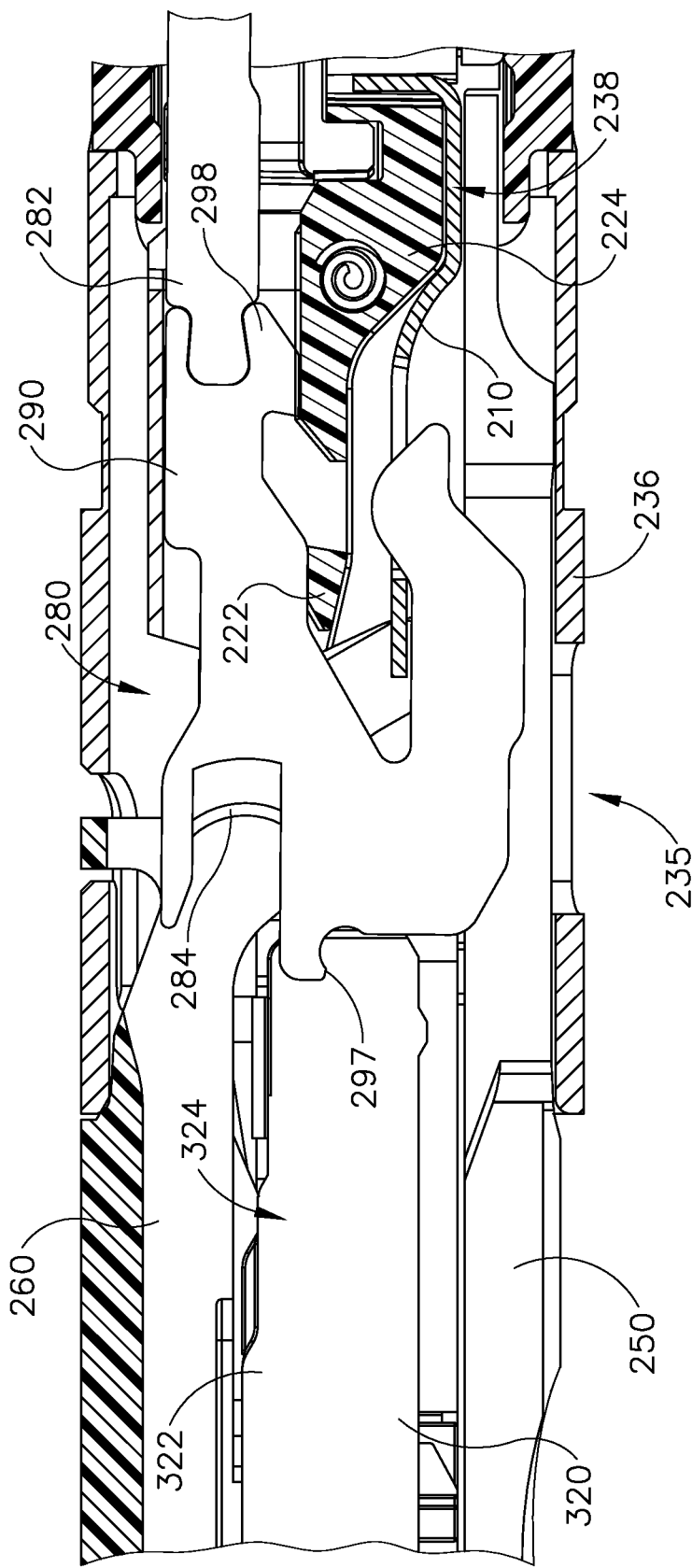
FIG. 32D depicts a cross-sectional view of the proximal end of the cartridge of FIG. 30 disposed within the end effector of FIG. 13, with the knife of the end effector moved back into the first longitudinal position and with the breakaway feature no longer present.
Figure 32E:
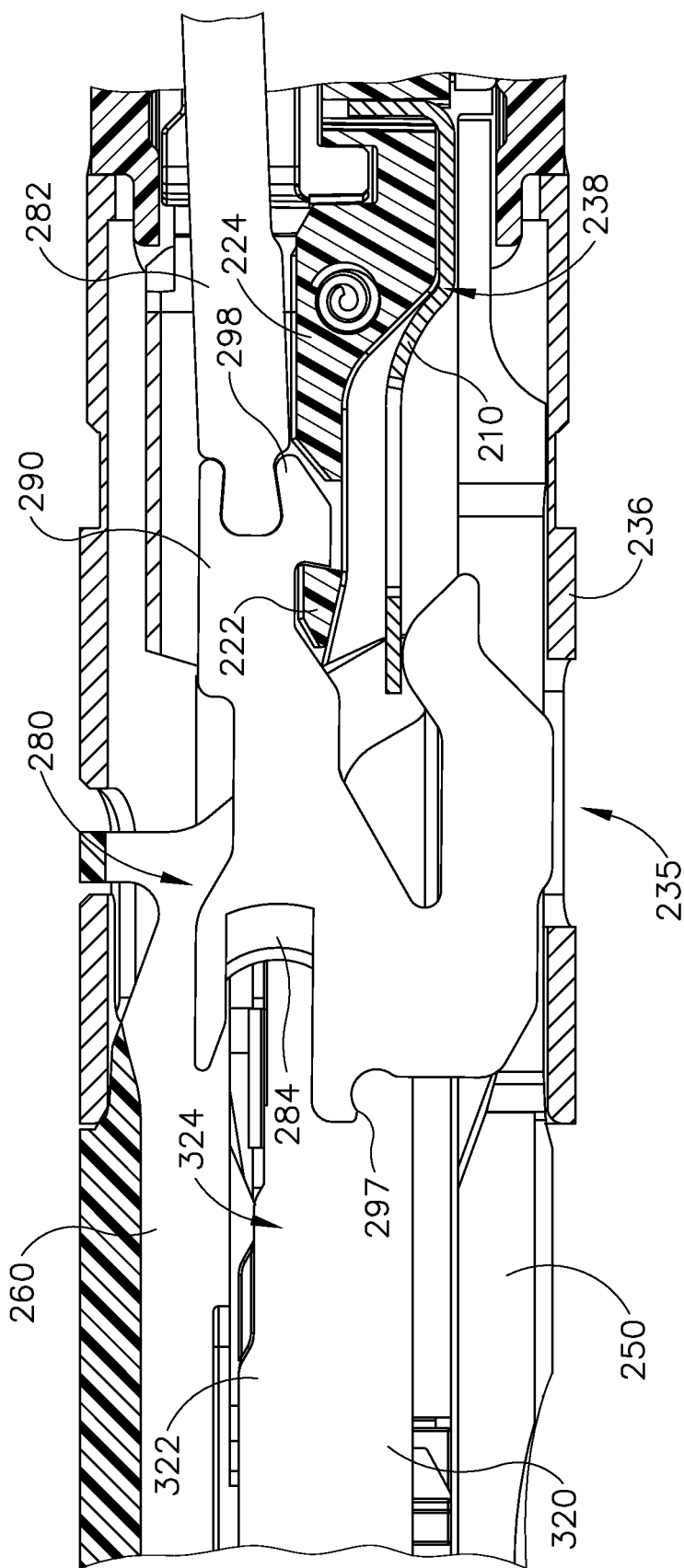
FIG. 32E depicts a cross-sectional view of the proximal end of the cartridge of FIG. 30 disposed within the end effector of FIG. 13, with the knife of the end effector moved into a lockout position upon being moved toward the second longitudinal position.
Figure 33:
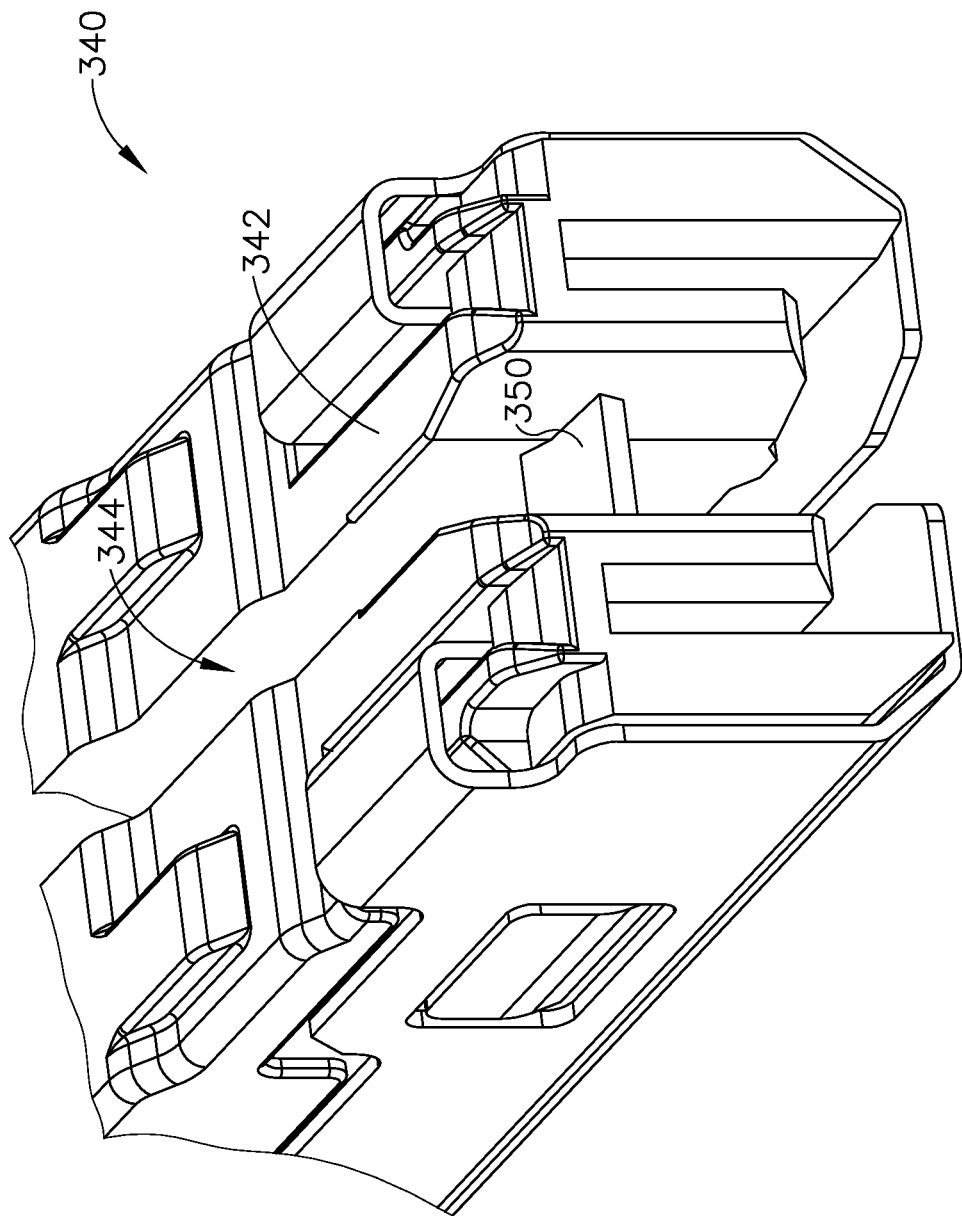
FIG. 33 depicts a perspective view of the proximal end of yet another exemplary alternative cartridge that may be incorporated into the end effector of FIG. 13.

FIG. 32A shows end effector (240) in an initial position. In the initial position, upper extension (290) of knife member (280) is positioned above engagement features (222, 224) of frame member (238). Also in the initial position, distal tip (297) of knife member (280) is in contact with a top surface of beam (330) of cartridge (320). As knife member (280) is fired distally, distal tip (297) of knife member (280) continues to engage the top surface of beam (330) as distal wall (281) of knife member (280) engages a proximal end (276) of sled (278), as shown in FIG. 32B. Engagement between distal tip (297) and the top surface of beam (330) maintains the vertical position of knife member (280). Because beam (330) maintains the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts beam (330) as knife member (280) drives wedge sled (278) distally as described above (FIG. 32C). After knife member (280) is fired distally, knife member (280) may be retracted proximally within lower jaw (250) (FIG. 32D). If an operator attempts to fire knife member (280) a second time, without beam (330) to maintain the vertical position of knife member (280), resilient member (210) will resiliently drive knife member (280) downwardly to the lockout position as discussed above with reference to FIG. 23B and as shown in FIG. 32E.

C. Exemplary Cartridge with Bypass Ramp

Figure 34:
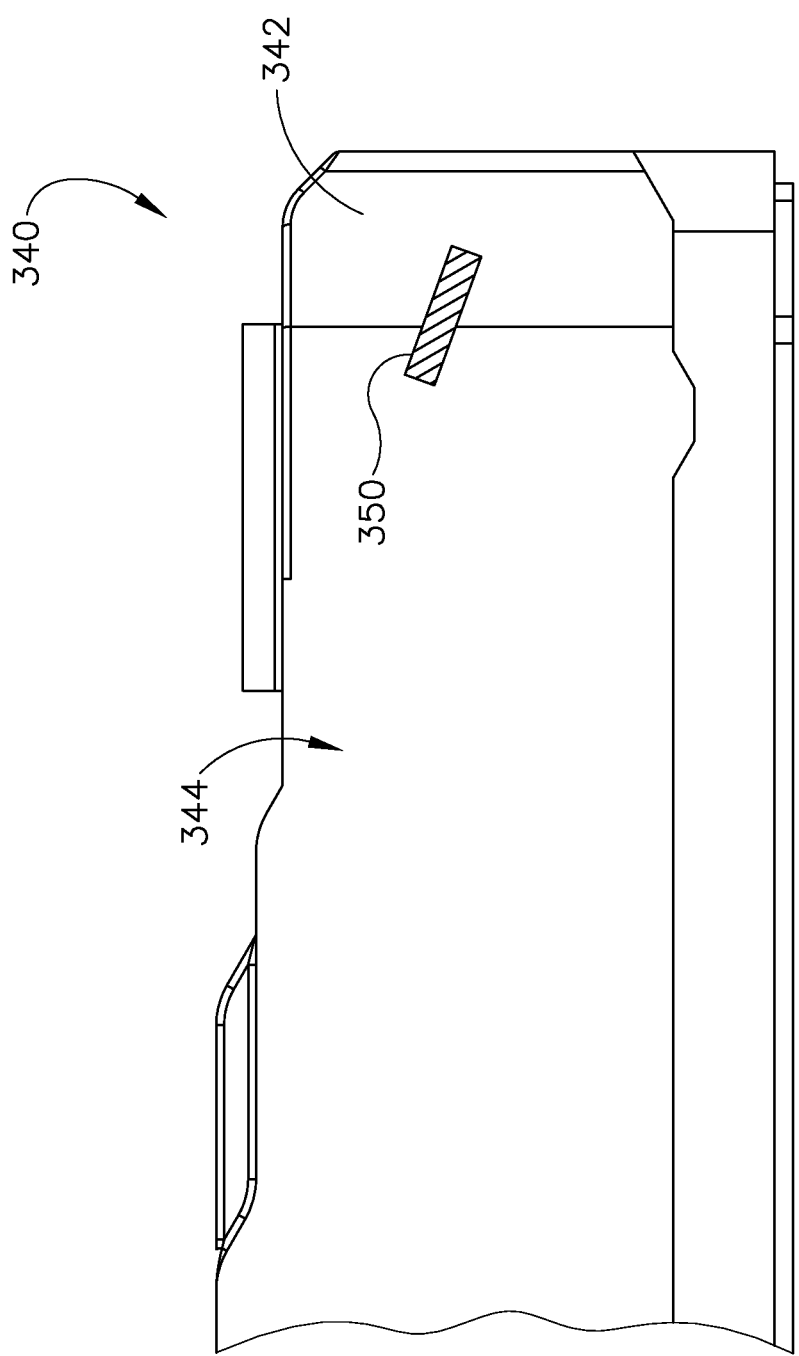
FIG. 34 depicts a cross-sectional side view of the proximal end of the cartridge of FIG. 33.
Figure 35:
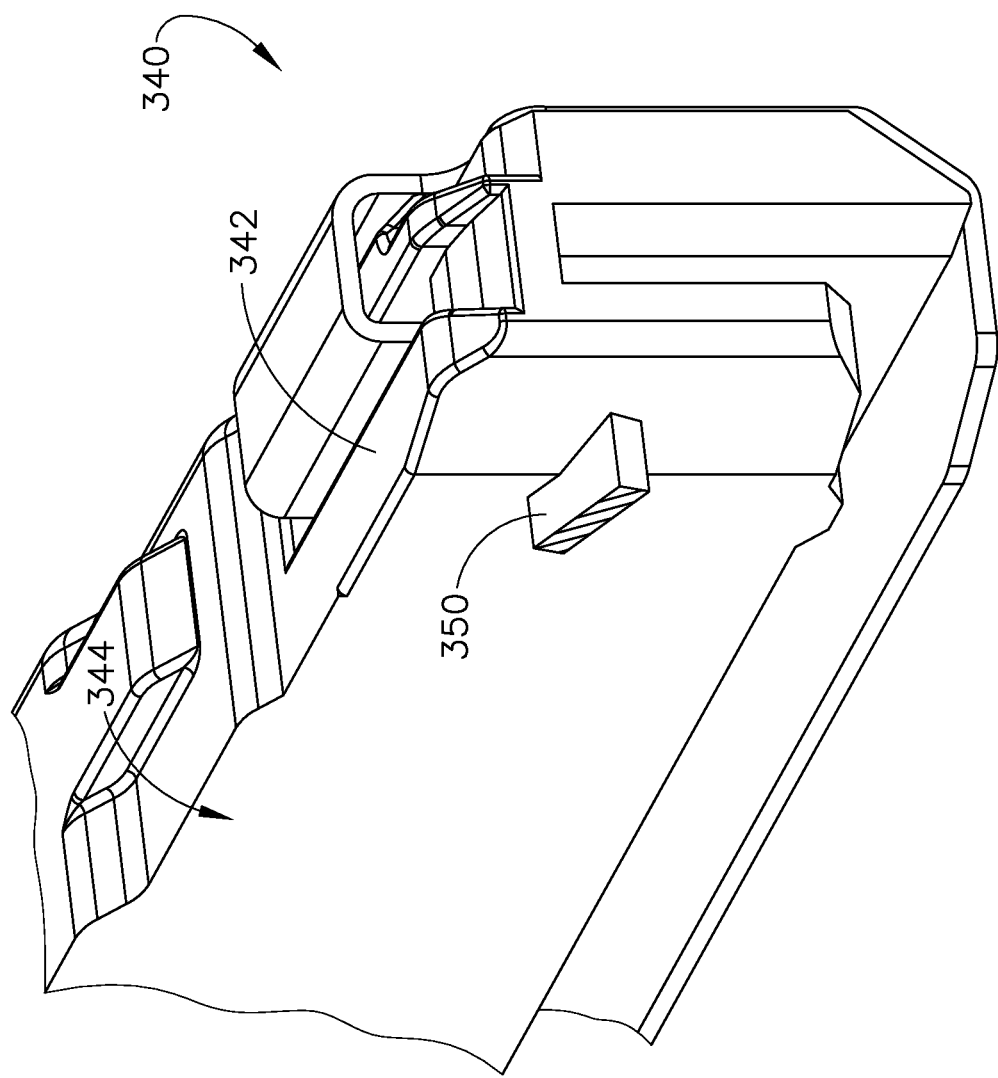
FIG. 35 depicts a cross-sectional perspective view of the proximal end of the cartridge of FIG. 33.

FIGS. 33-36E show another exemplary cartridge (340) having a spent cartridge lockout feature. It should be understood that cartridge (340) may be readily used in end effector (240) or in other end effectors. Cartridge (340) of the present example is configured to operate substantially similar to cartridges (70, 270) discussed above except for the differences discussed below. Cartridge (340) includes a cartridge body (342) having a longitudinal channel (344) through which wedge sled (278) and knife member (280) may be longitudinally translated. The spent cartridge lockout feature of the present example comprises a breakaway or cutaway ramp (350) extending between opposing interior surfaces of channel (344) of cartridge body (342). Ramp (350) is positioned within channel (344) such that ramp (350) is in the path of knife member (280). As best shown in FIG. 34, ramp (350) of the present example is angled upwardly-distally. As will be discussed in more detail below, as knife member (280) is fired distally through channel (344), knife member (280) is configured to break and/or cut ramp (350). Also as will be discussed in more detail below, ramp (350) is configured to allow for firing of knife member (280) when ramp (350) is present; and to prevent firing of knife member (280) when ramp (350) is not present.

Figure 36A:
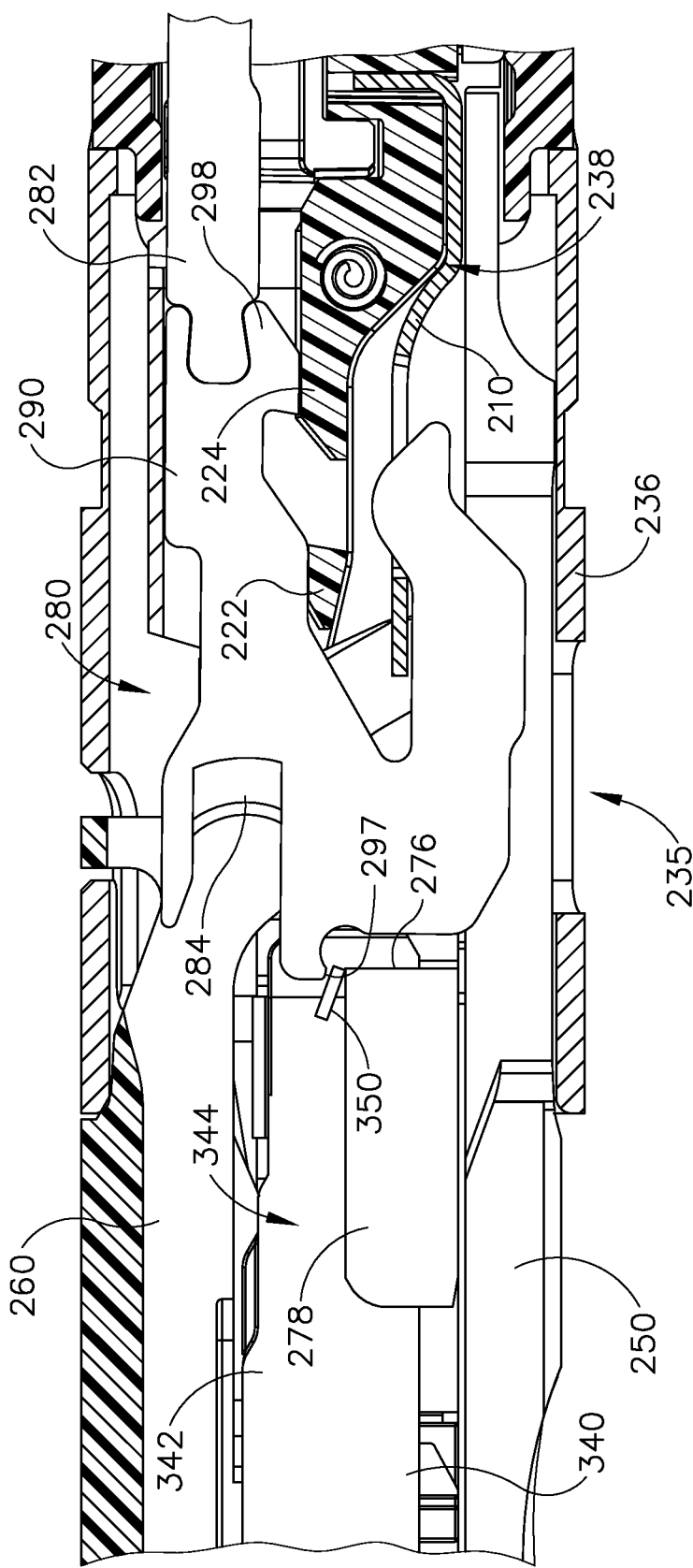
FIG. 36A depicts a cross-sectional view of the proximal end of the cartridge of FIG. 33 disposed within the end effector of FIG. 13, with a sled of the cartridge in a first longitudinal position and with a knife of the end effector in a first longitudinal position.
Figure 36B:
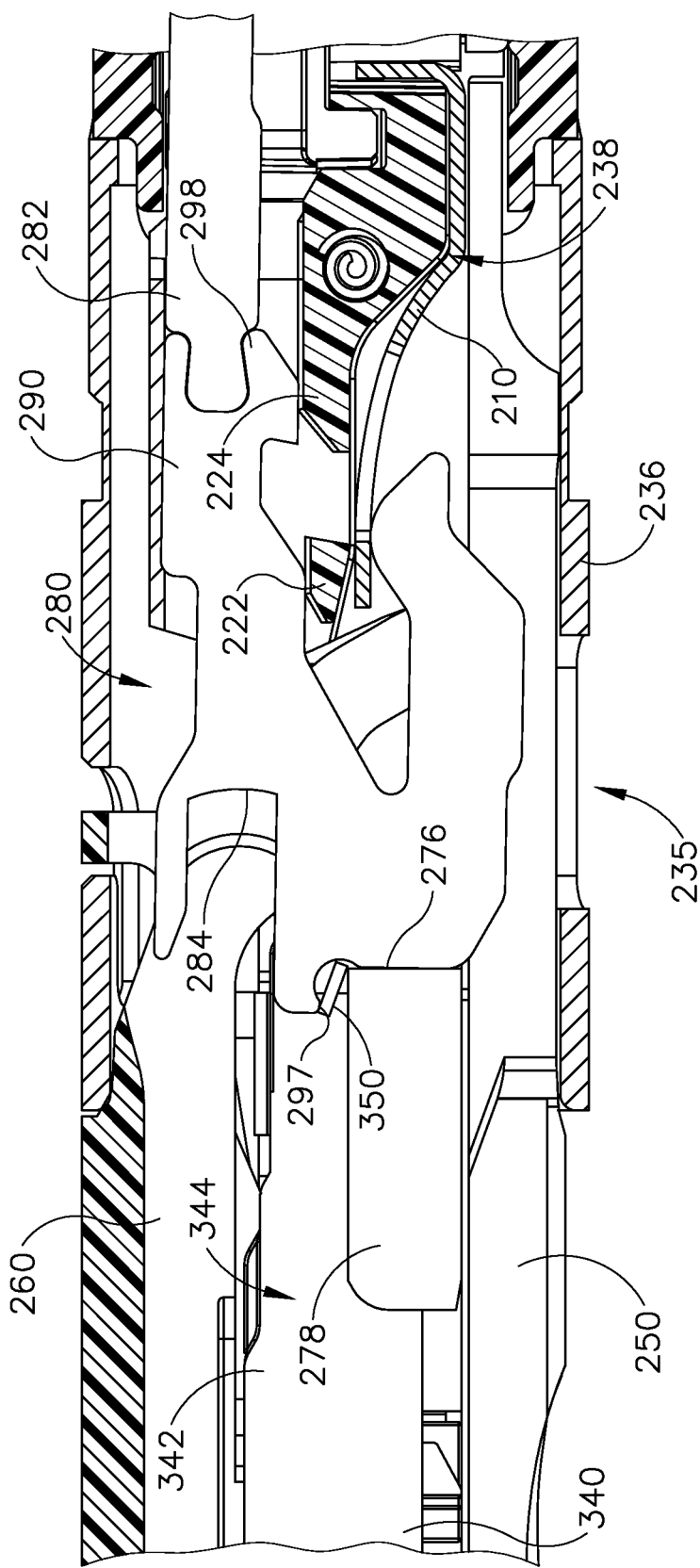
FIG. 36B depicts a cross-sectional view of the proximal end of the cartridge of FIG. 33 disposed within the end effector of FIG. 13, with the sled of the cartridge in the first longitudinal position and with the knife of the end effector moved into a second longitudinal position.
Figure 36C:
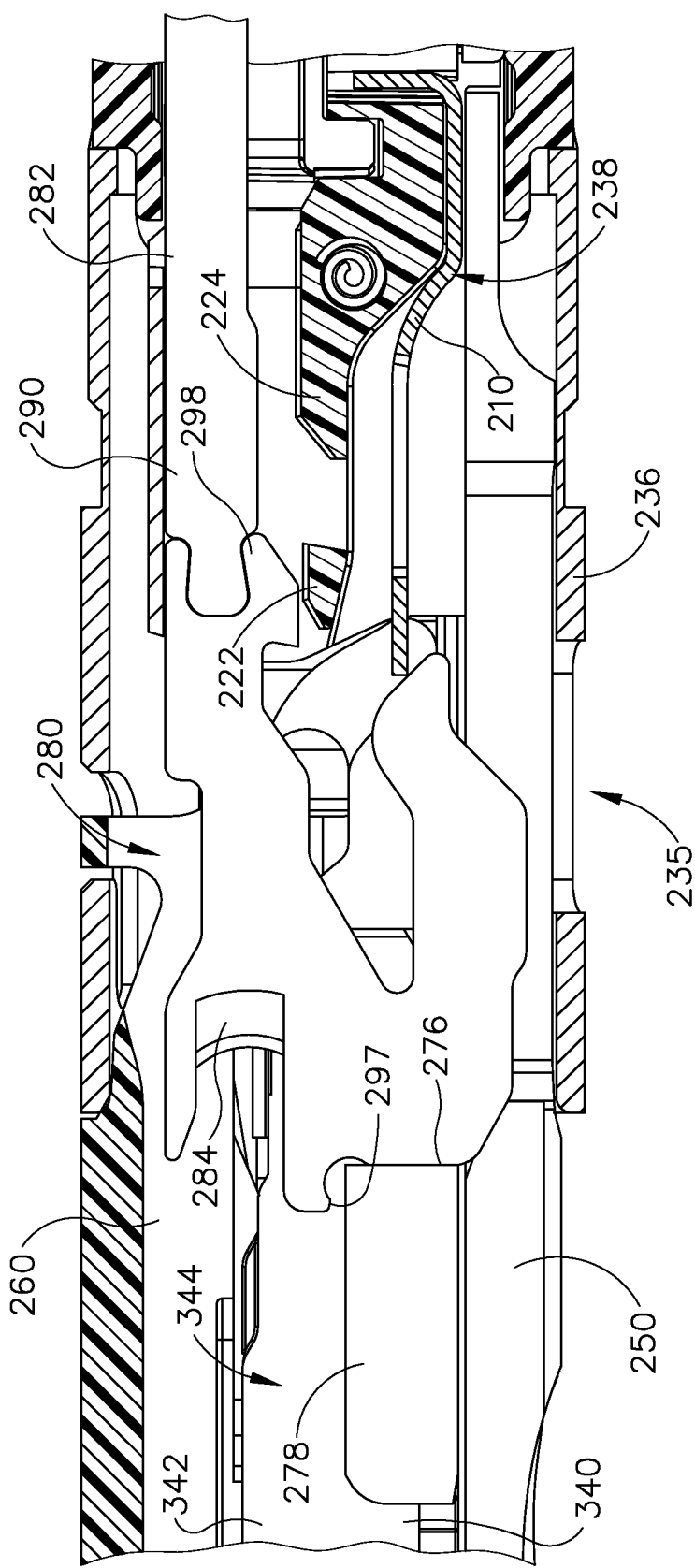
FIG. 36C depicts a cross-sectional view of the proximal end of the cartridge of FIG. 33 disposed within the end effector of FIG. 13, with the sled of the cartridge moved into a second longitudinal position by movement of the knife of the end effector into a third longitudinal position, with the knife breaking through the breakaway feature of the cartridge.
Figure 36D:
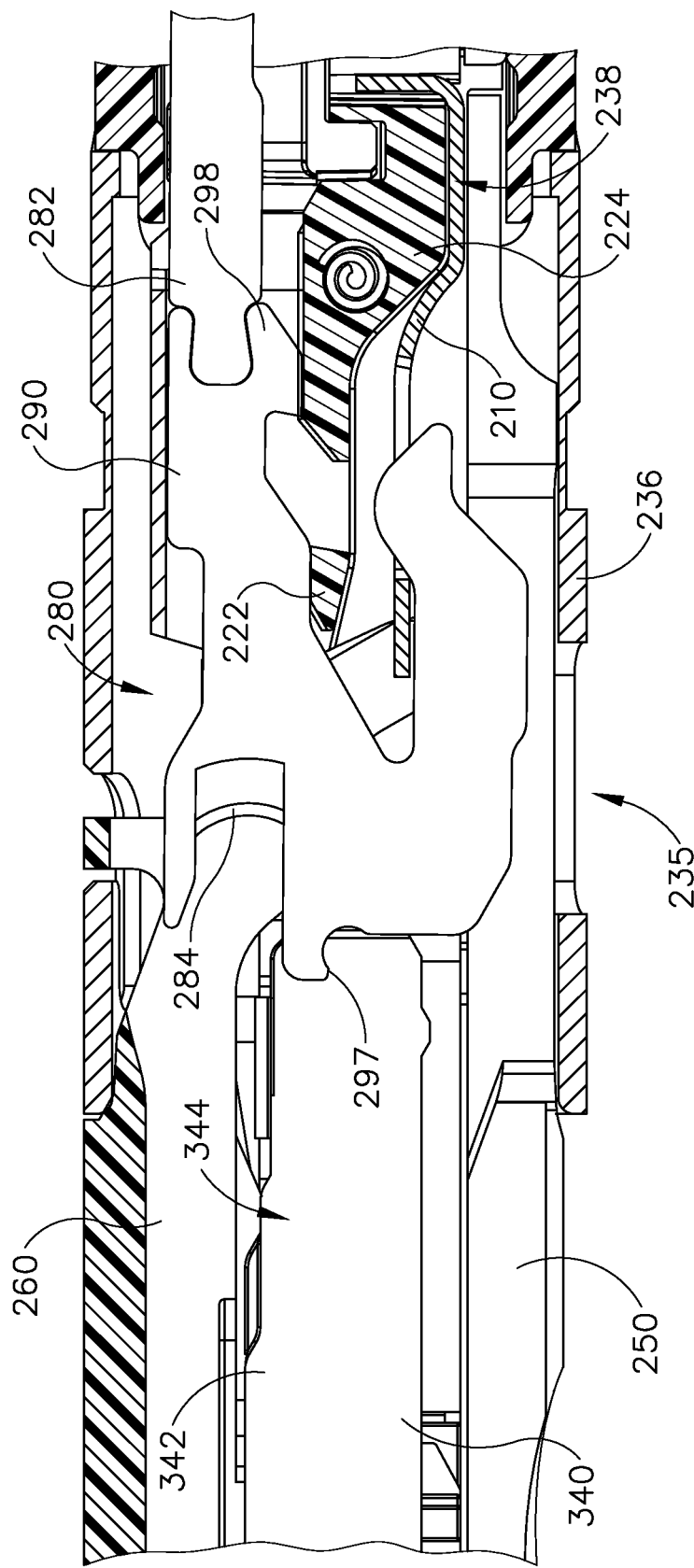
FIG. 36D depicts a cross-sectional view of the proximal end of the cartridge of FIG. 33 disposed within the end effector of FIG. 13, with the knife of the end effector moved back into the first longitudinal position and with the breakaway feature no longer present.
Figure 36E:
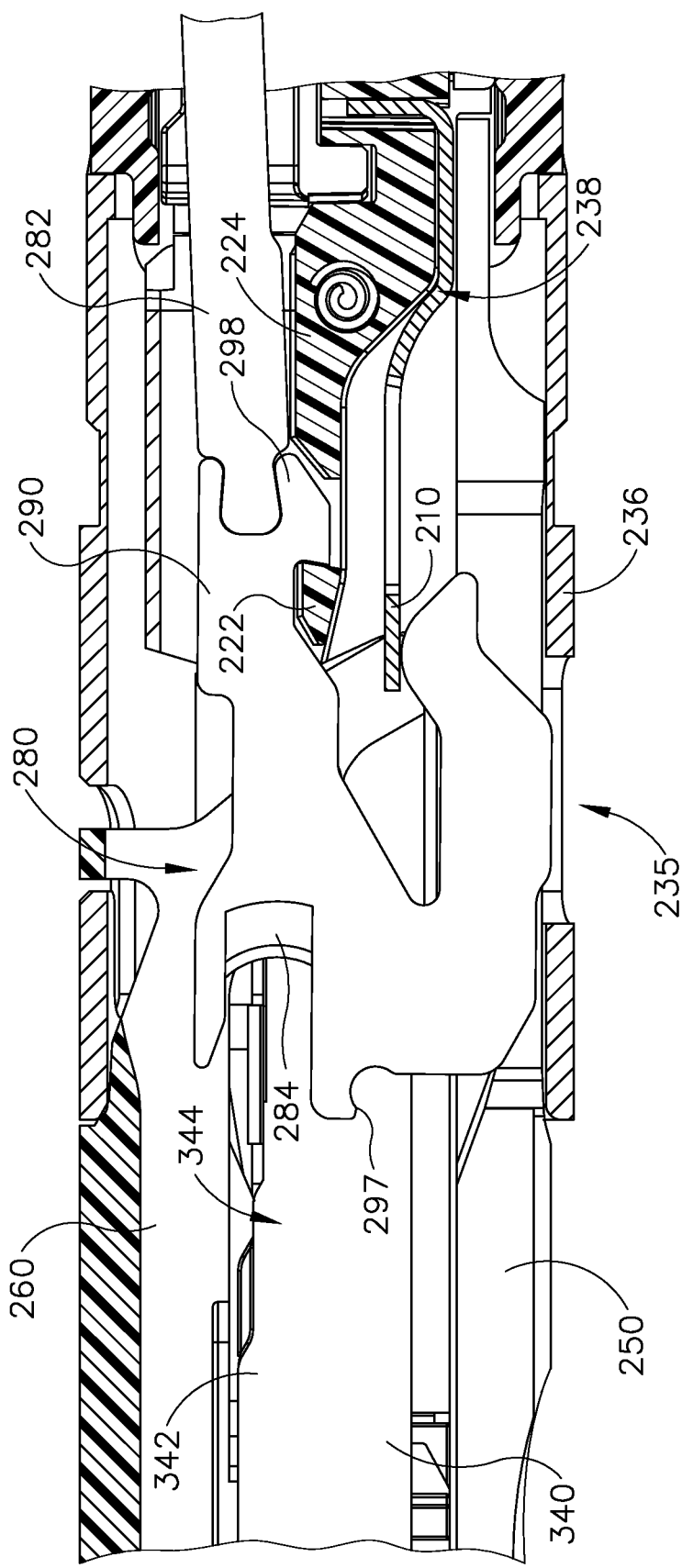
FIG. 36E depicts a cross-sectional view of the proximal end of the cartridge of FIG. 33 disposed within the end effector of FIG. 13, with the knife of the end effector moved into a lockout position upon being moved toward the second longitudinal position.
Figure 37:
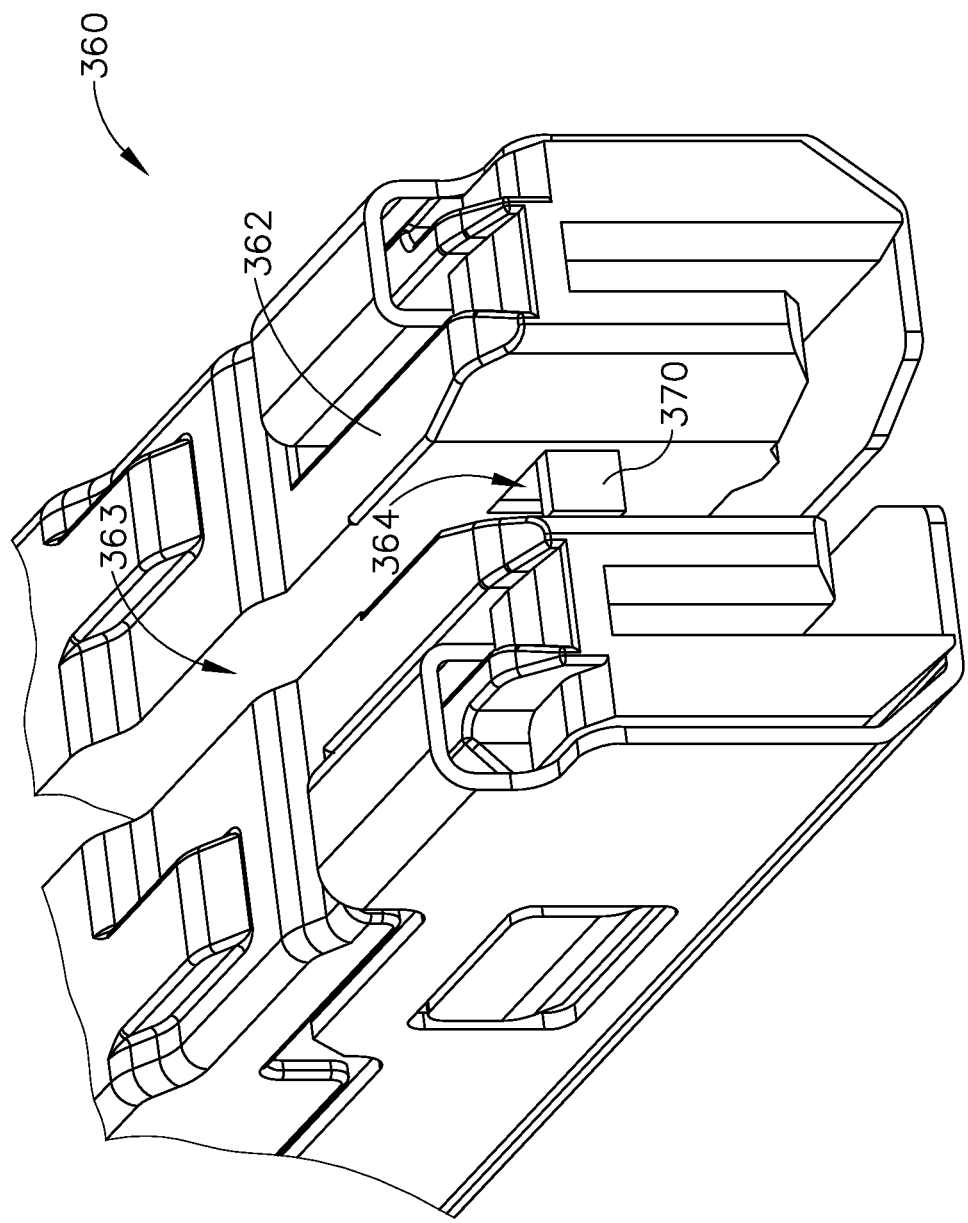
FIG. 37 depicts a perspective view of the proximal end of yet another exemplary alternative cartridge that may be incorporated into the end effector of FIG. 13.
Figure 38:
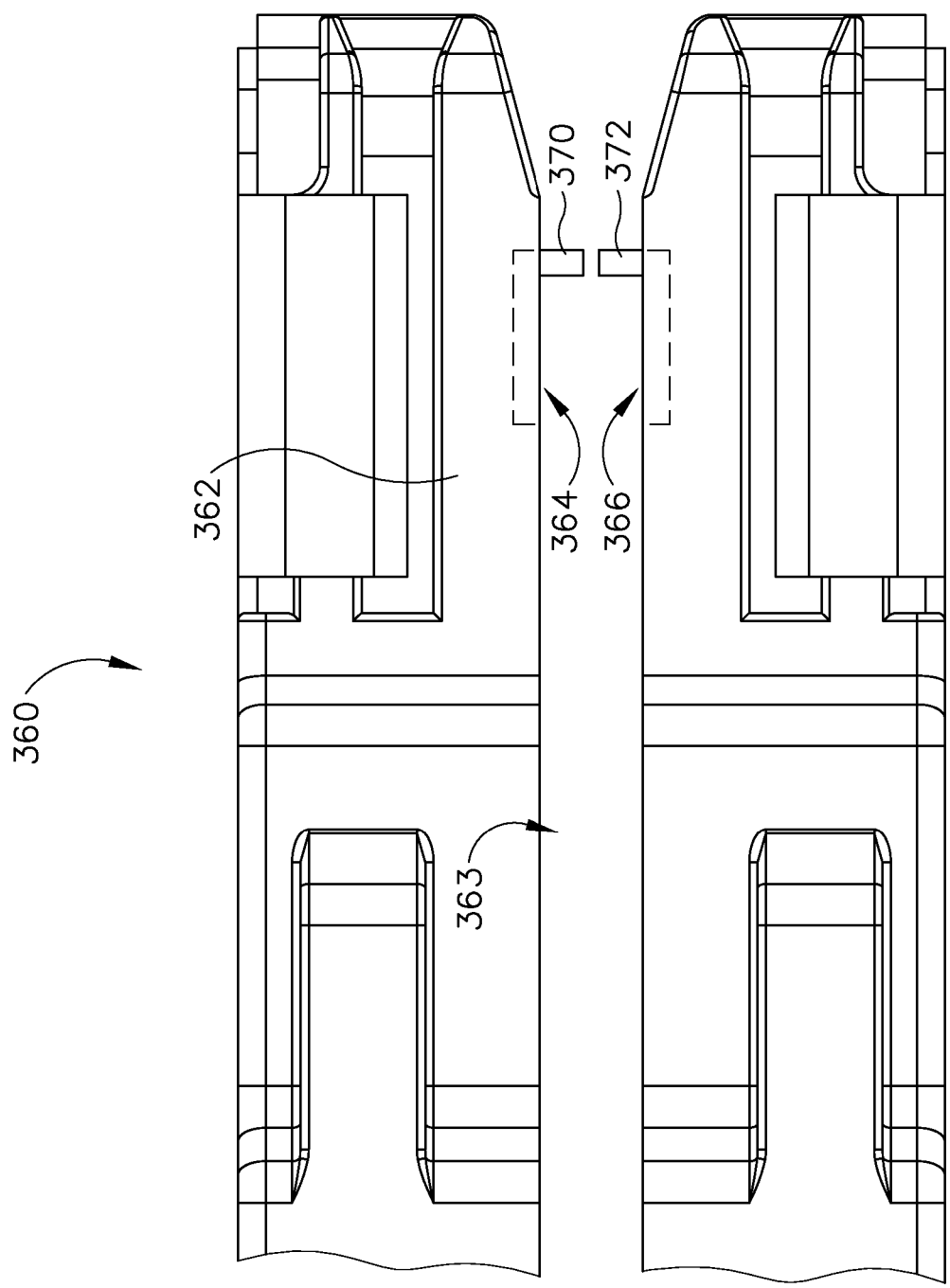
FIG. 38 depicts a top view of the proximal end of the cartridge of FIG. 37.
Figure 39:
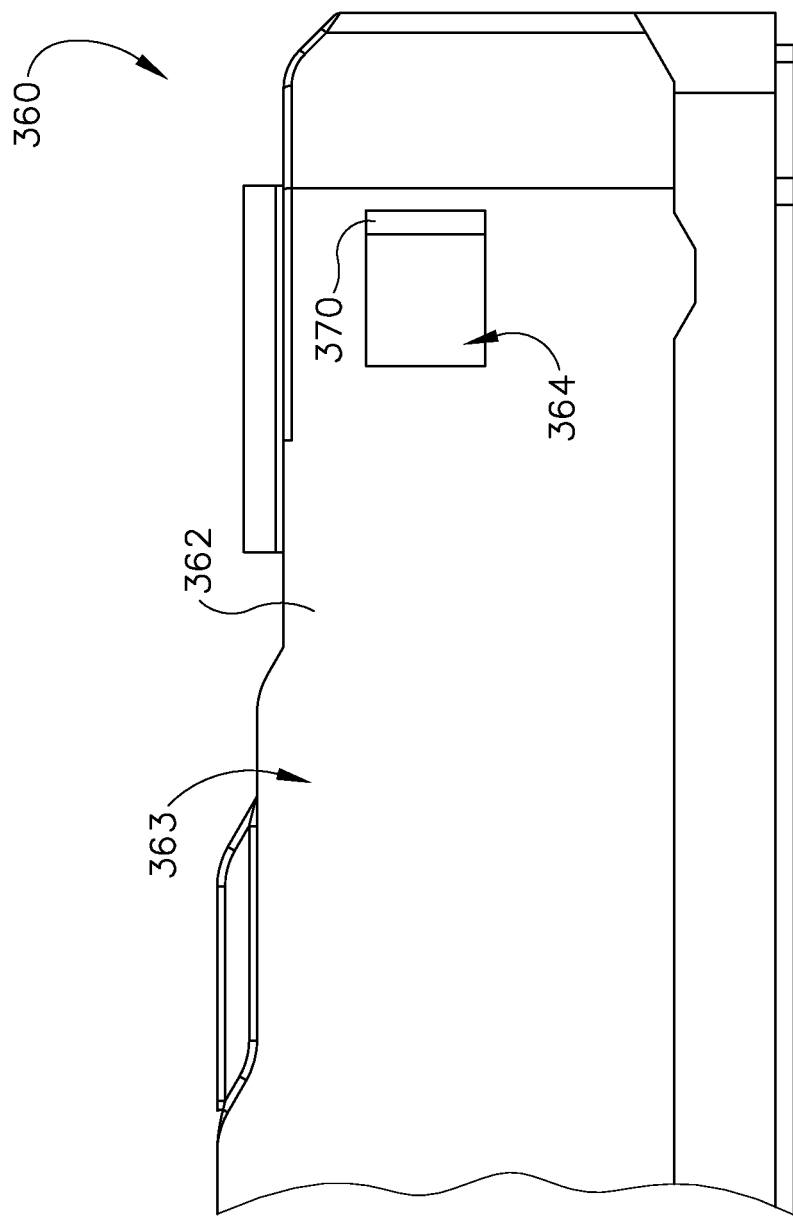
FIG. 39 depicts a cross-sectional side view of the proximal end of the cartridge of FIG. 37.
Figure 40:
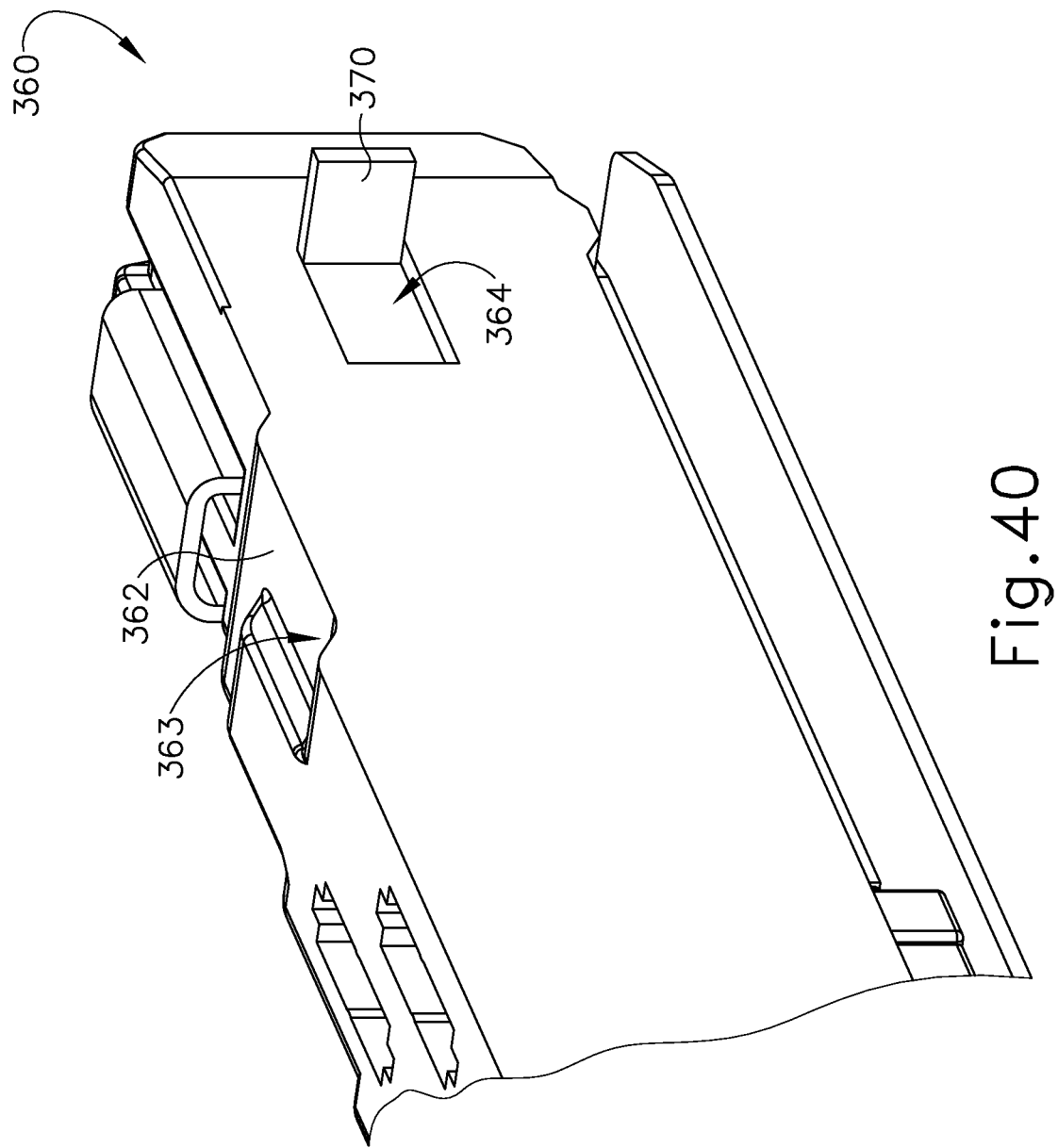
FIG. 40 depicts a cross-sectional perspective view of the proximal end of the cartridge of FIG. 37.

FIG. 36A shows end effector (240) in an initial position. In the initial position, upper extension (290) of knife member (280) is positioned above engagement features (222, 224) of frame member (238). Also in the initial position, distal tip (297) of knife member (280) is in contact with a top surface of ramp (350) of cartridge (340). As knife member (280) is fired distally, distal tip (297) of knife member (280) continues to engage the top surface of beam (330) as distal wall (281) of knife member (280) engages a proximal end (276) of sled (278), as shown in FIG. 36B. Engagement between distal tip (297) and the top surface of ramp (350) maintains the vertical position of knife member (280). Because ramp (350) maintains the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts ramp (350) as knife member (280) drives wedge sled (278) distally as described above (FIG. 36C). After knife member (280) is fired distally, knife member (280) may be retracted proximally within lower jaw (250) (FIG. 36D). If an operator attempts to fire knife member (280) a second time, without ramp (350) to maintain the vertical position of knife member (280), resilient member (210) will resiliently drive knife member (280) downwardly to the lockout position as discussed above with reference to FIG. 23B and as shown in FIG. 36E.

D. Exemplary Cartridge with Bypass Tabs

FIGS. 37-41E show another exemplary cartridge (360) having a spent cartridge lockout feature. It should be understood that cartridge (360) may be readily used in end effector (240) or in other end effectors. Cartridge (360) of the present example is configured to operate substantially similar to cartridges (70, 270) discussed above except for the differences discussed below. Cartridge (360) includes a cartridge body (362) having a longitudinal channel (363) through which wedge sled (278) and knife member (280) may be longitudinally translated. The spent cartridge lockout feature of the present example comprises a pair of tabs (370, 372) extending from opposing interior surfaces of channel (363) of cartridge body (362). The interior surfaces of channel (364) of cartridge body (362) comprise a pair rectangular recesses (364, 366) within which tabs (370, 372) are pivotably disposed. Tabs (370) are pivotably secured within rectangular recesses (364, 366) via living hinges. Each tab (370, 372) is pivotable between an unexposed position, in which tabs (370, 372) are substantially completely disposed within rectangular recesses (364, 366); and an exposed position, in which tabs (370, 372) are substantially completely disposed outside of rectangular recesses (364, 366) and are positioned within channel (363), oriented substantially orthogonal to the respective interior surfaces of channel (363) of cartridge body (362). As will be discussed in more detail below, as knife member (280) is fired distally through channel (363), knife member (280) is configured to drive tabs (370, 372) from the exposed position toward the unexposed position. Tabs (370, 372) are configured to remain in the unexposed position once driven into the unexposed position. Also as will be discussed in more detail below, tabs (370, 372) are configured to allow for firing of knife member (280) when tabs (370, 372) are in the exposed position; and to prevent firing of knife member (280) when tabs (370, 372) are in the unexposed position.

Figure 41A:
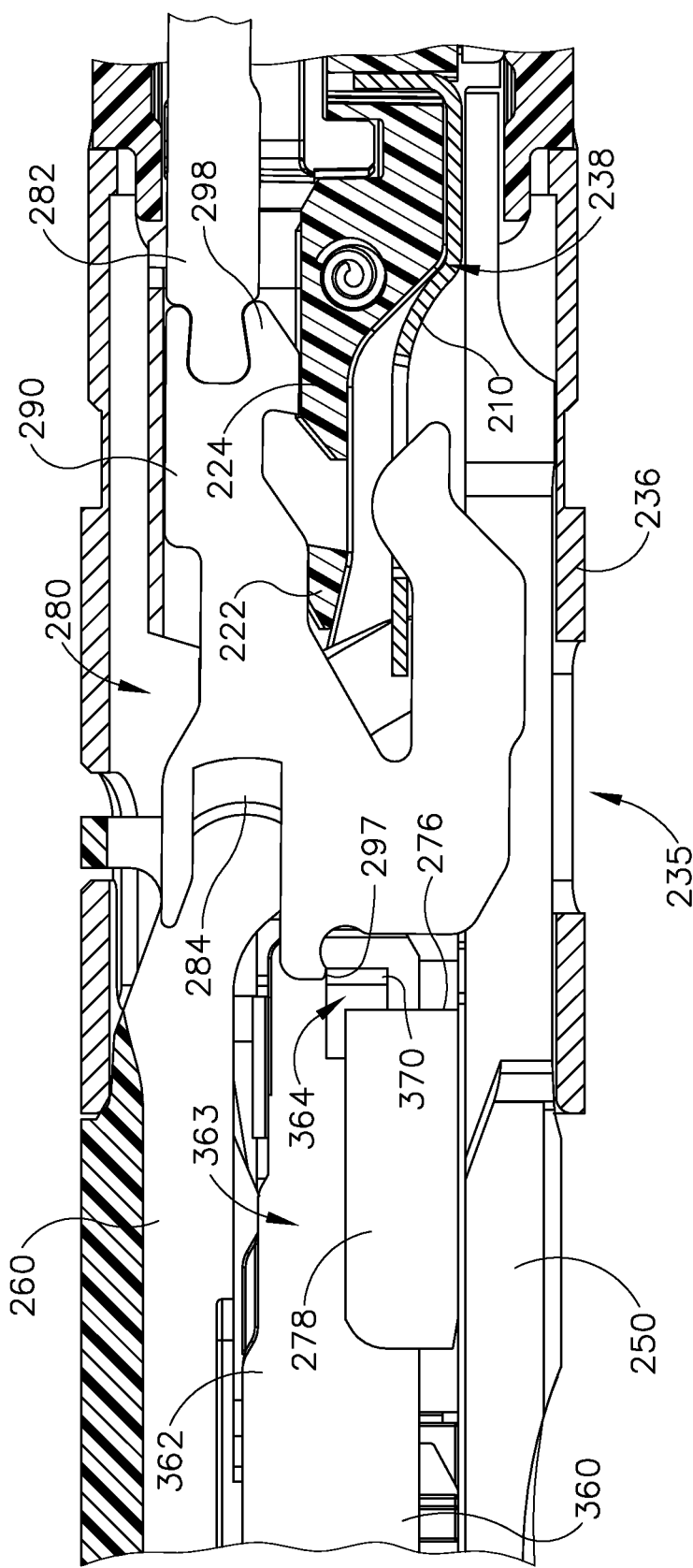
FIG. 41A depicts a cross-sectional view of the proximal end of the cartridge of FIG. 37 disposed within the end effector of FIG. 13, with the breakaway feature in a first rotational position, with a sled of the cartridge in a first longitudinal position, and with a knife of the end effector in a first longitudinal position.
Figure 41B:
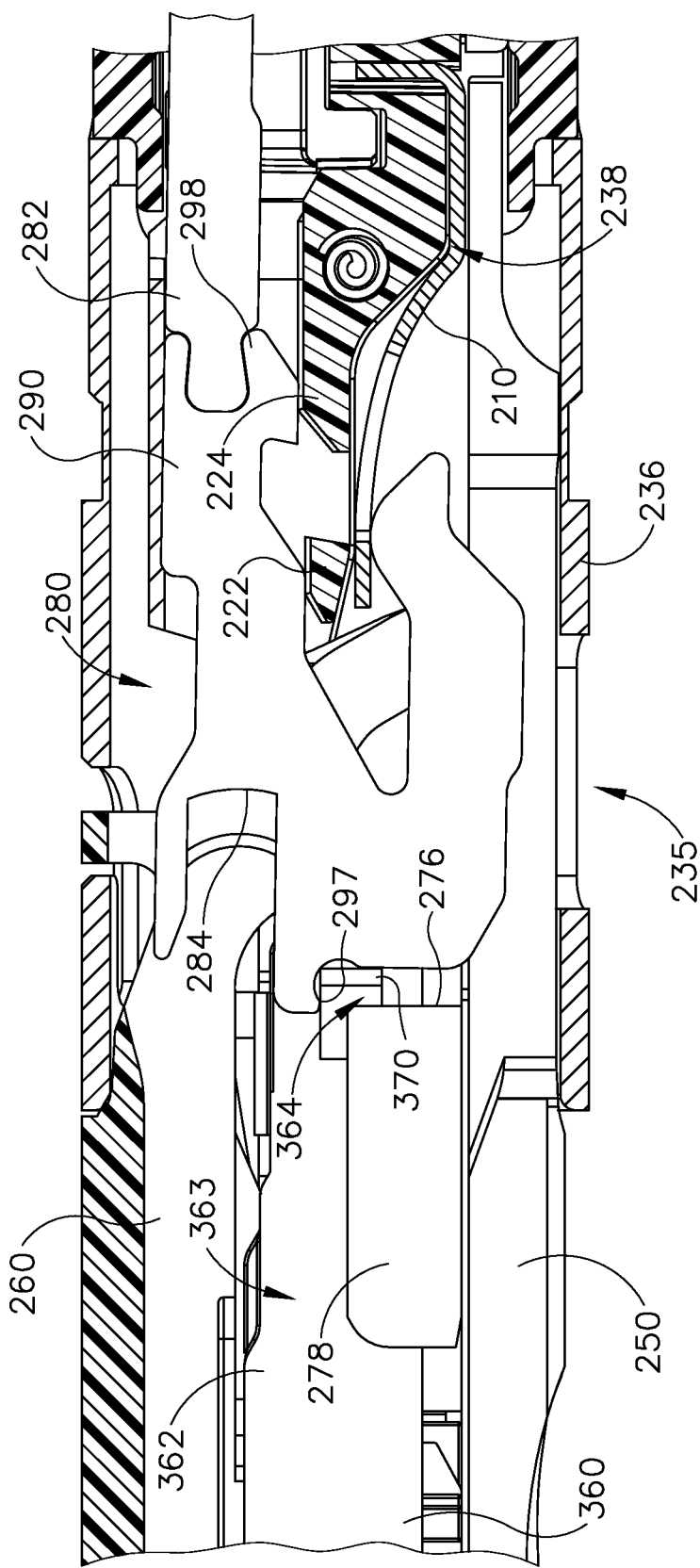
FIG. 41B depicts a cross-sectional view of the proximal end of the cartridge of FIG. 37 disposed within the end effector of FIG. 13, with the breakaway feature in the first rotational position, with the sled of the cartridge in the first longitudinal position, and with the knife of the end effector moved into a second longitudinal position.
Figure 41C:
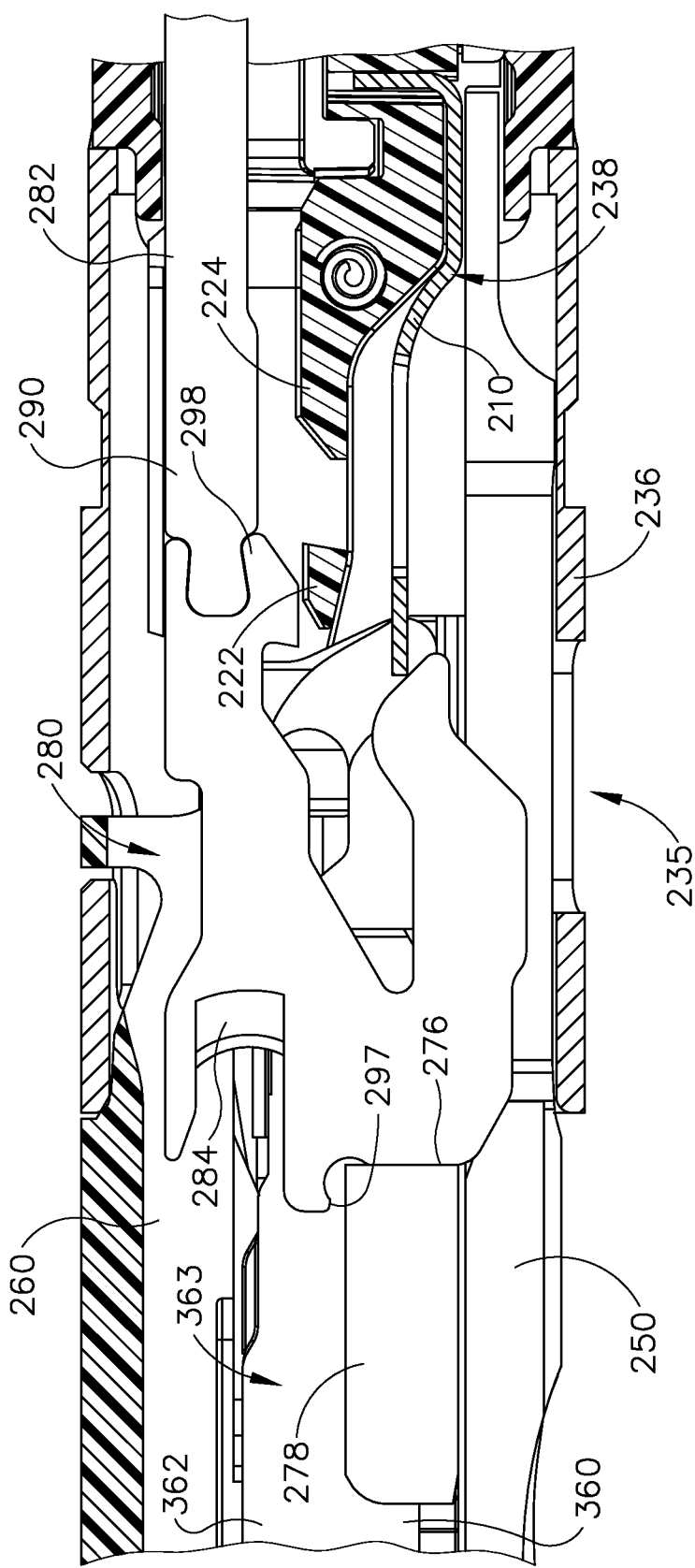
FIG. 41C depicts a cross-sectional view of the proximal end of the cartridge of FIG. 37 disposed within the end effector of FIG. 13, with the breakaway feature moved into a second rotational position and with the sled of the cartridge moved into a second longitudinal position both by movement of the knife of the end effector into a third longitudinal position.
Figure 41D:
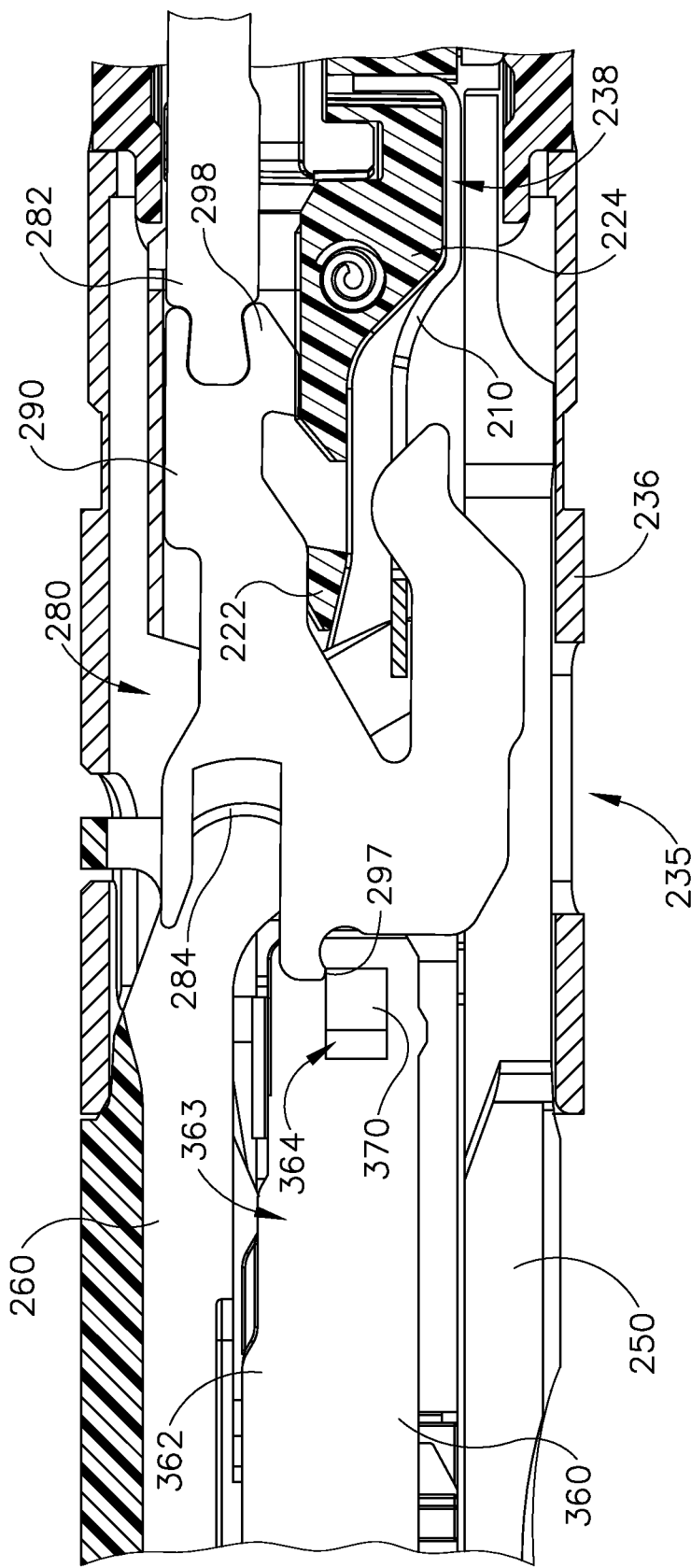
FIG. 41D depicts a cross-sectional view of the proximal end of the cartridge of FIG. 37 disposed within the end effector of FIG. 13, with the breakaway feature in the second rotational position and with the knife of the end effector moved back into the first longitudinal position.
Figure 41E:
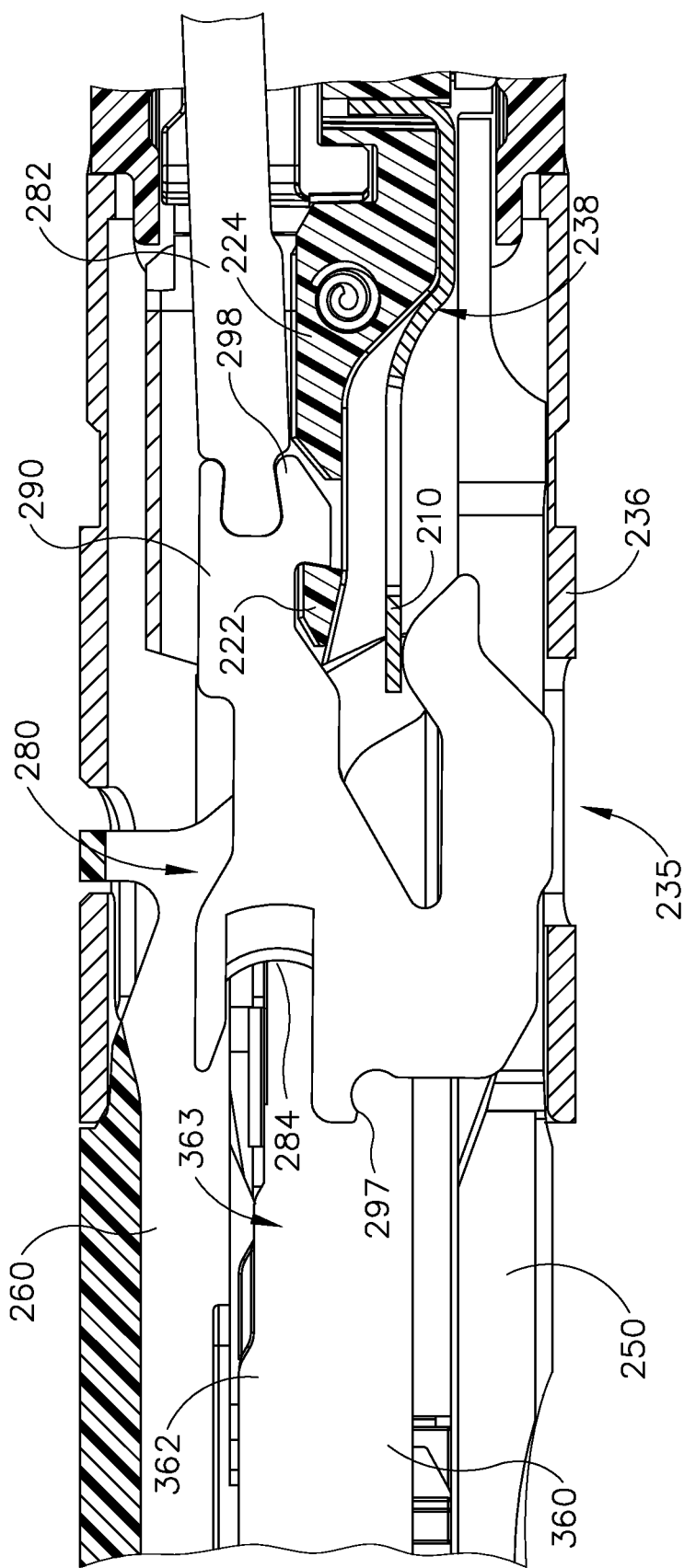
FIG. 41E depicts a cross-sectional view of the proximal end of the cartridge of FIG. 37 disposed within the end effector of FIG. 13, with the knife of the end effector moved into a lockout position upon being moved toward the second longitudinal position.

FIG. 41A shows end effector (240) in an initial position. In the initial position, upper extension (290) of knife member (280) is positioned above engagement features (222, 224) of frame member (238). Also in the initial position, tabs (370, 372) are in the exposed position and distal tip (297) of knife member (280) is in contact with a top surface of one or both tabs (370, 372) of cartridge (360). As knife member (280) is fired distally, distal tip (297) of knife member (280) continues to engage the top surface of one or both tabs (370, 372) as distal wall (281) of knife member (280) engages a proximal end (276) of sled (278), as shown in FIG. 41B. Engagement between distal tip (297) and of one or both tabs (370, 372) maintains the vertical position of knife member (280). Because one or both tabs (370, 372) maintain the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) drives tabs (370, 372) into the unexposed position as knife member (280) drives wedge sled (278) distally as described above (FIG. 41C). After knife member (280) is fired distally, knife member (280) may be retracted proximally within lower jaw (250) (FIG. 41D). If an operator attempts to fire knife member (280) a second time, with tabs (370, 372) in the unexposed position, tabs (370, 372) no longer maintain the vertical position of knife member (280), resilient member (210) will resiliently drive knife member (280) downwardly to the lockout position as discussed above with reference to FIG. 23B and as shown in FIG. 41E.

E. Exemplary Cartridges with Bypass Fins

Figure 42:
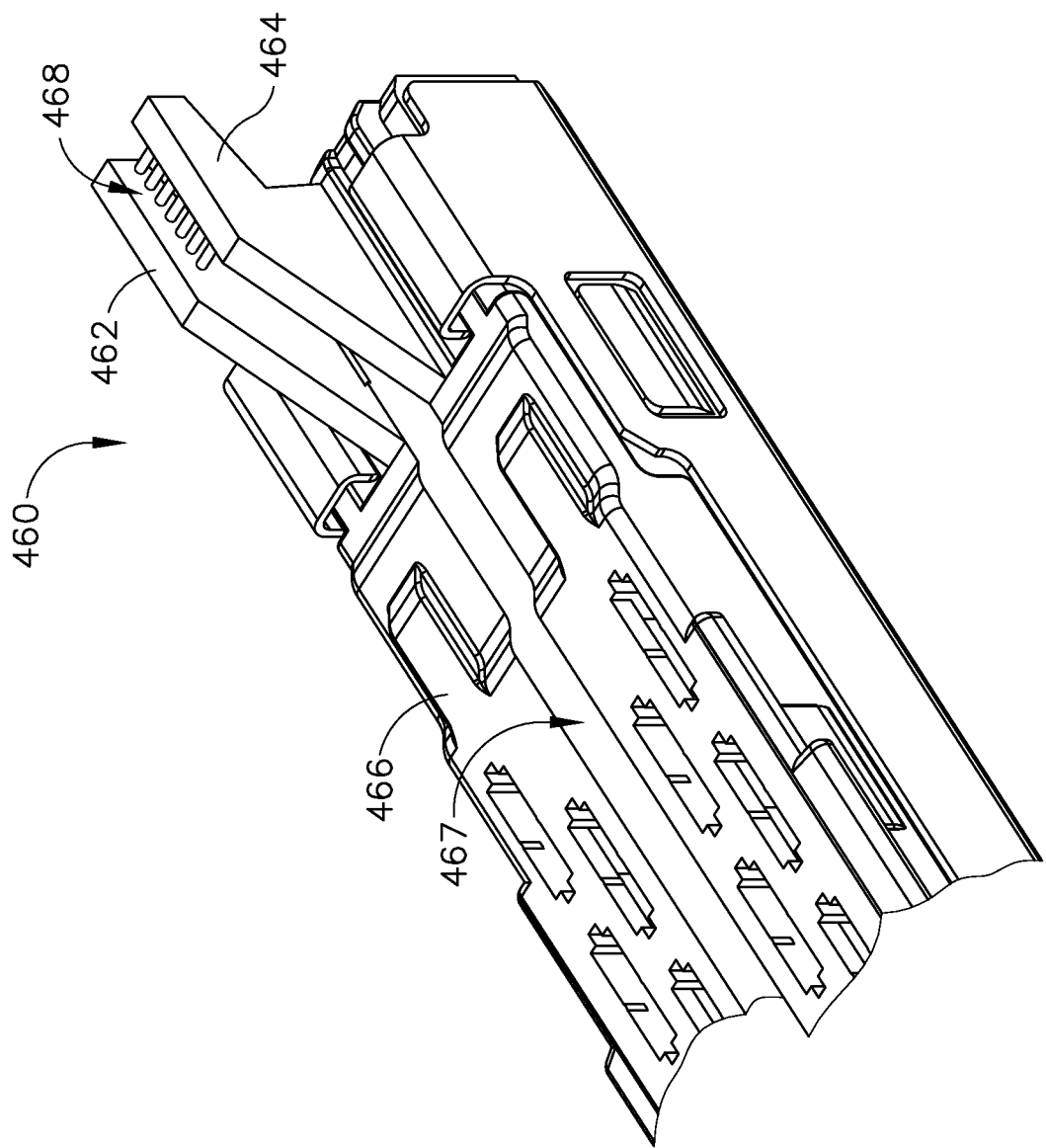
FIG. 42 depicts a perspective view of the proximal end of yet another exemplary alternative cartridge that may be incorporated into the end effector of FIG. 13.
Figure 43:
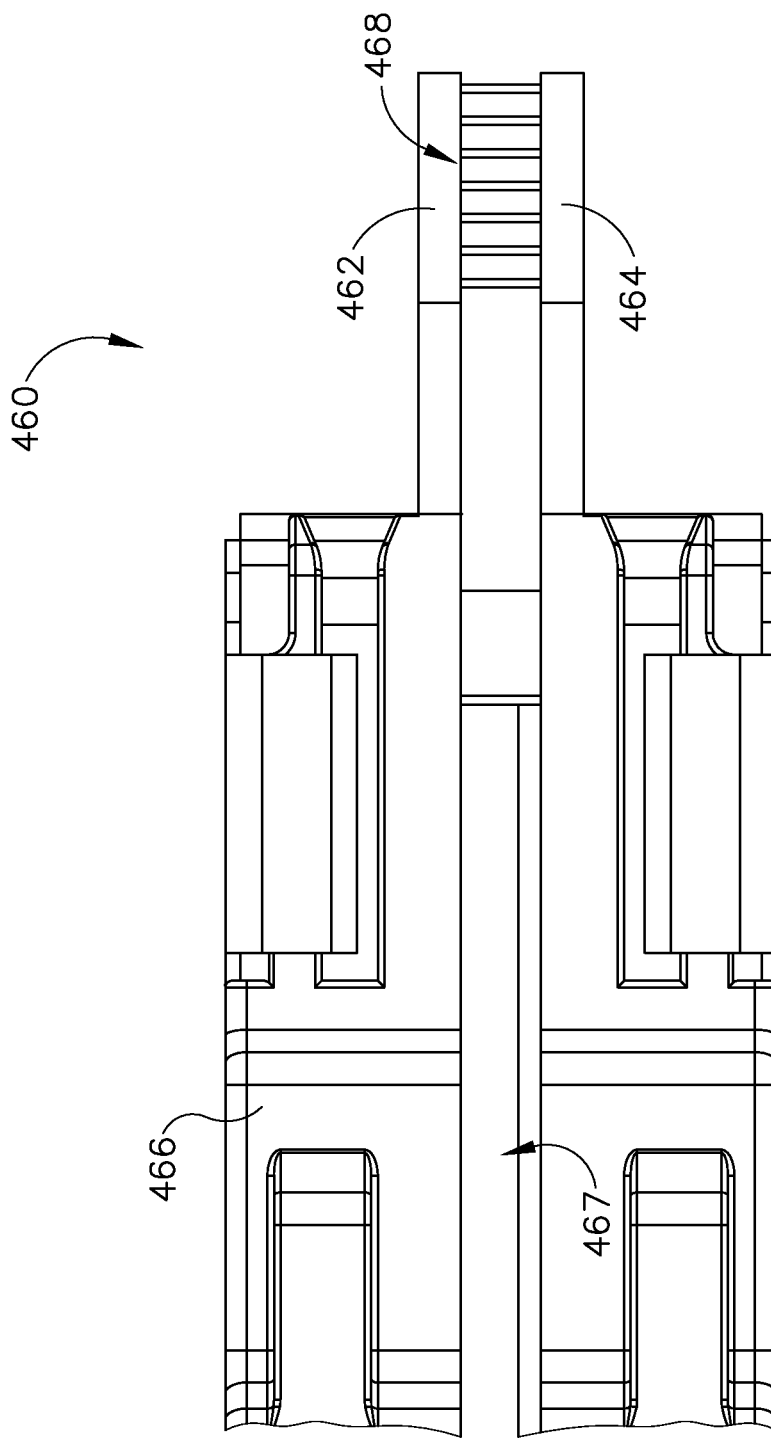
FIG. 43 depicts a top view of the proximal end of the cartridge of FIG. 42.

FIGS. 42 and 43 show another exemplary cartridge (460) having a spent cartridge lockout feature. It should be understood that cartridge (460) may be readily used in end effector (240) or in other end effectors. Cartridge (460) of the present example is configured to operate substantially similar to cartridges (70, 270) discussed above except for the differences discussed below. Cartridge (460) includes a cartridge body (466) having a longitudinal channel (467) through which wedge sled (278) and knife member (280) may be longitudinally translated. The spent cartridge lockout feature of the present example comprises a pair of fins (462, 464) extending upwardly and proximally from a cartridge body (466). A plurality of breakaway or cutaway pins (468) within a gap (463) defined between fins (462, 464). Gap (463) between fins (462, 464) is aligned with channel (467) of cartridge body (466) such that pins (468) are in the path of distally translating knife member (280). As will be discussed in more detail below, as knife member (280) is fired distally through channel (467) and gap (463), knife member (280) is configured to break and/or cut pins (468). Also as will be discussed in more detail below, pins (468) are configured to allow for firing of knife member (280) when pins (468) are present and to prevent firing of knife member (280) when pins (468) are not present.

Figure 44A:
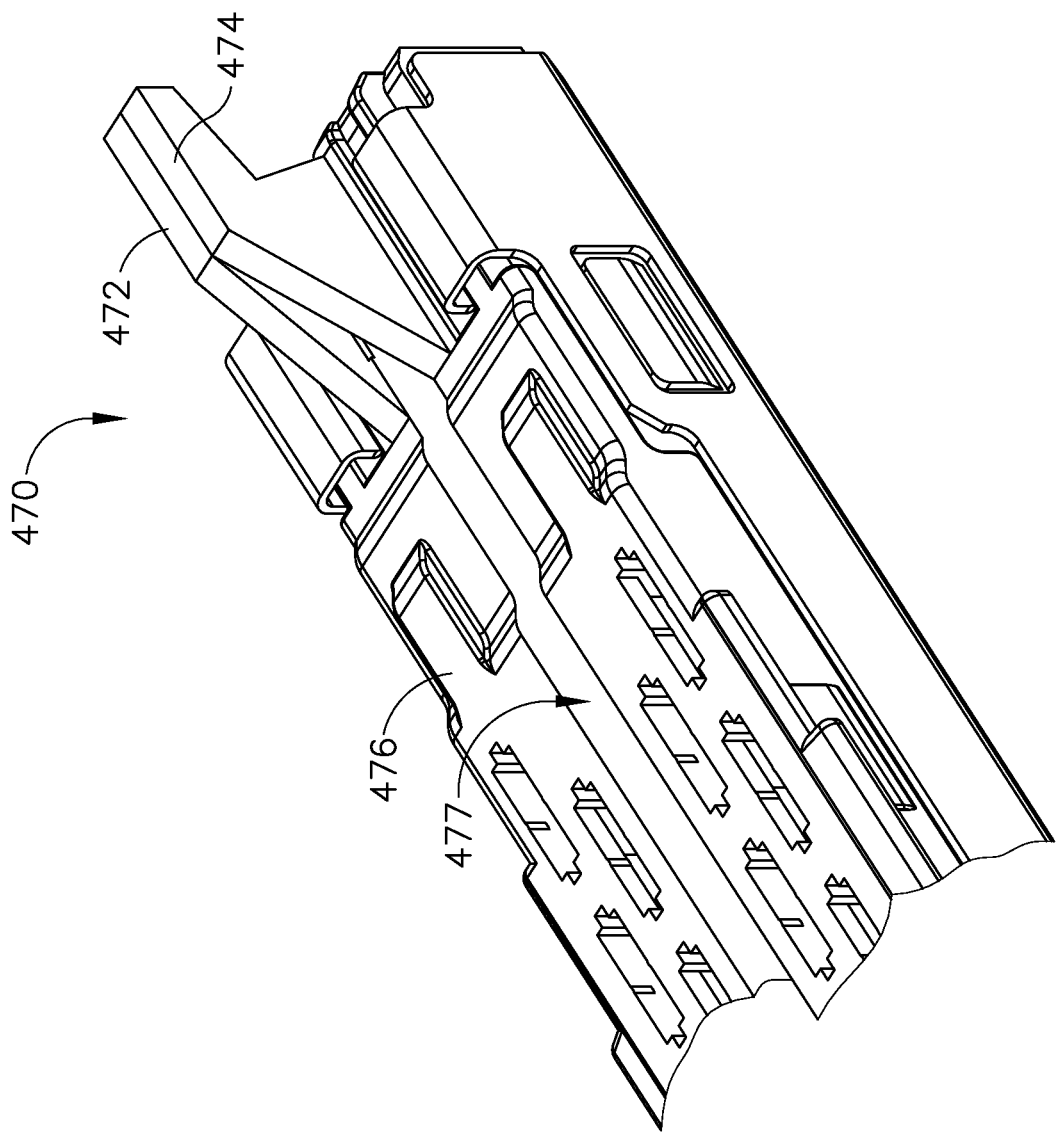
FIG. 44A depicts a perspective view of the proximal end of yet another exemplary alternative cartridge that may be incorporated into the end effector of FIG. 13.
Figure 44B:
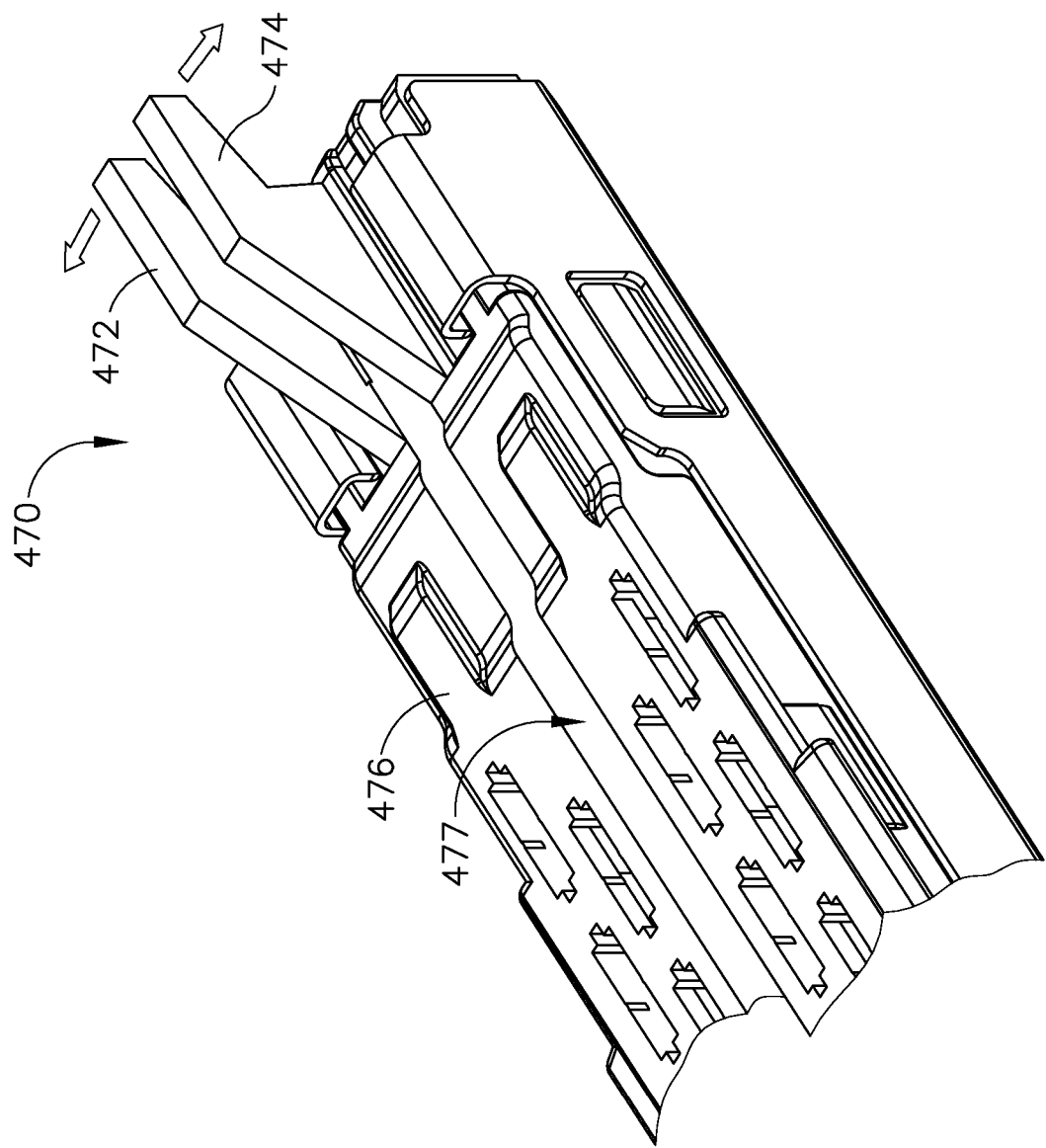
FIG. 44B depicts a perspective view of the proximal end of yet another exemplary alternative cartridge with the alternative pair of guide fins moved into an open position.
Figure 45B:
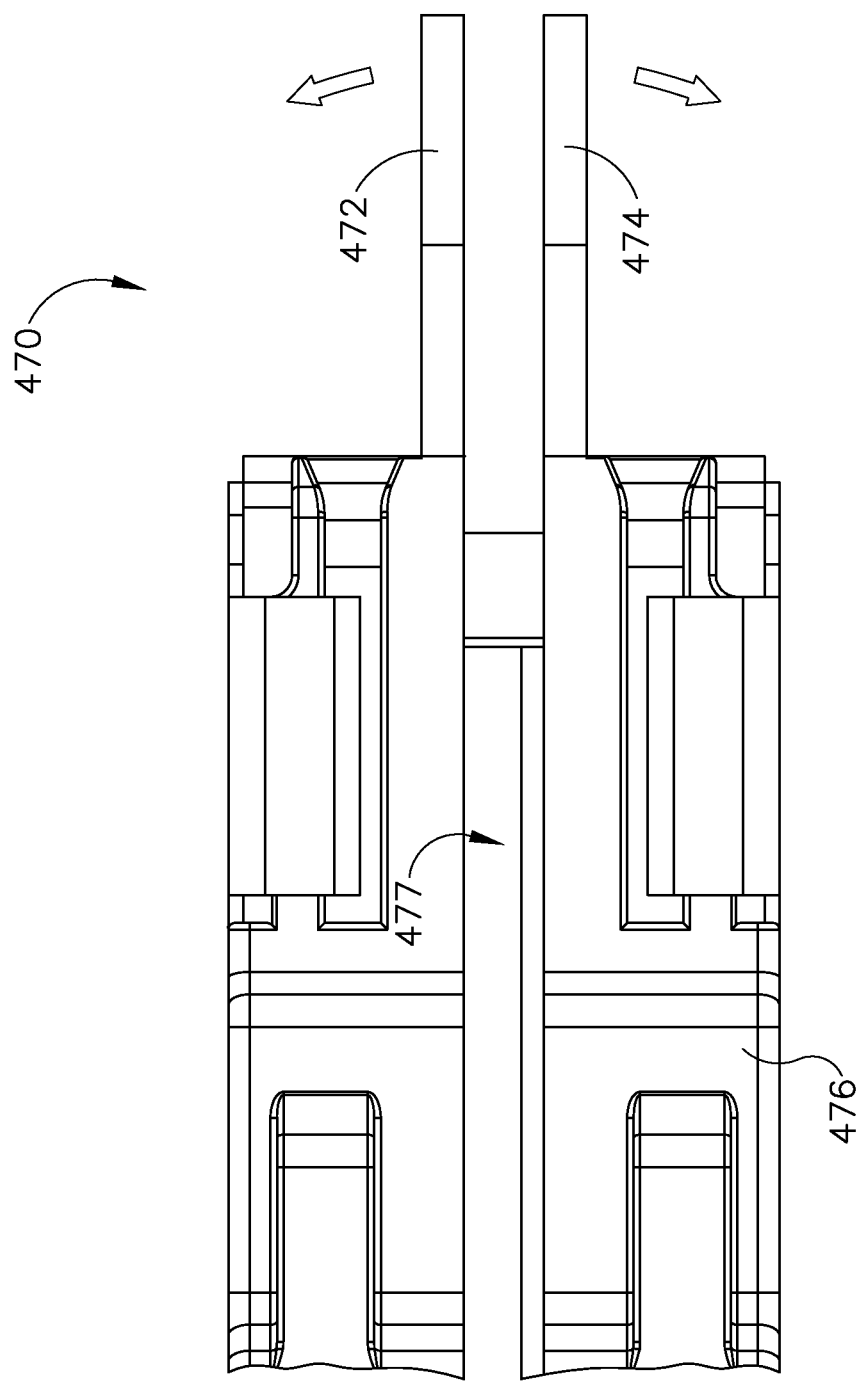
FIG. 45B depicts a top view of the proximal end of the cartridge of FIG. 44A with the guide fins moved into the open position.

FIGS. 44A-45B show another exemplary cartridge (470) having a spent cartridge lockout feature. It should be understood that cartridge (470) may be readily used in end effector (240) or in other end effectors. Cartridge (470) of the present example is configured to operate substantially similar to cartridges (70, 270) discussed above except for the differences discussed below. Cartridge (470) includes a cartridge body (476) having a longitudinal channel (477) through which wedge sled (278) and knife member (280) may be longitudinally translated. The spent cartridge lockout feature of the present example comprises a pair of malleable fins (472, 474) extending upwardly and proximally from a cartridge body (476). Initially, fins (472, 474) are in a closed position as shown in FIGS. 44A and 45A. In the closed position, fins (472, 474) contact each other along a plane aligned with channel (477) of cartridge body (476), such that fins (472, 474) are in the path of distally translating knife (280). As will be discussed in more detail below, as knife member (280) is fired distally through channel (467), knife member (280) is configured to drive fins (472, 474) outwardly into an open position as shown in FIGS. 44B and 45B. Fins (472, 474) are configured to remain in the open position upon being driven into the open position by firing of knife member (280). As will be discussed in more detail below, fins (468) are configured to allow for firing of knife member (280) when fins (472, 474) are in the closed position; and to prevent firing of knife member (280) when fins (472, 474) in the open position.

Figure 46:
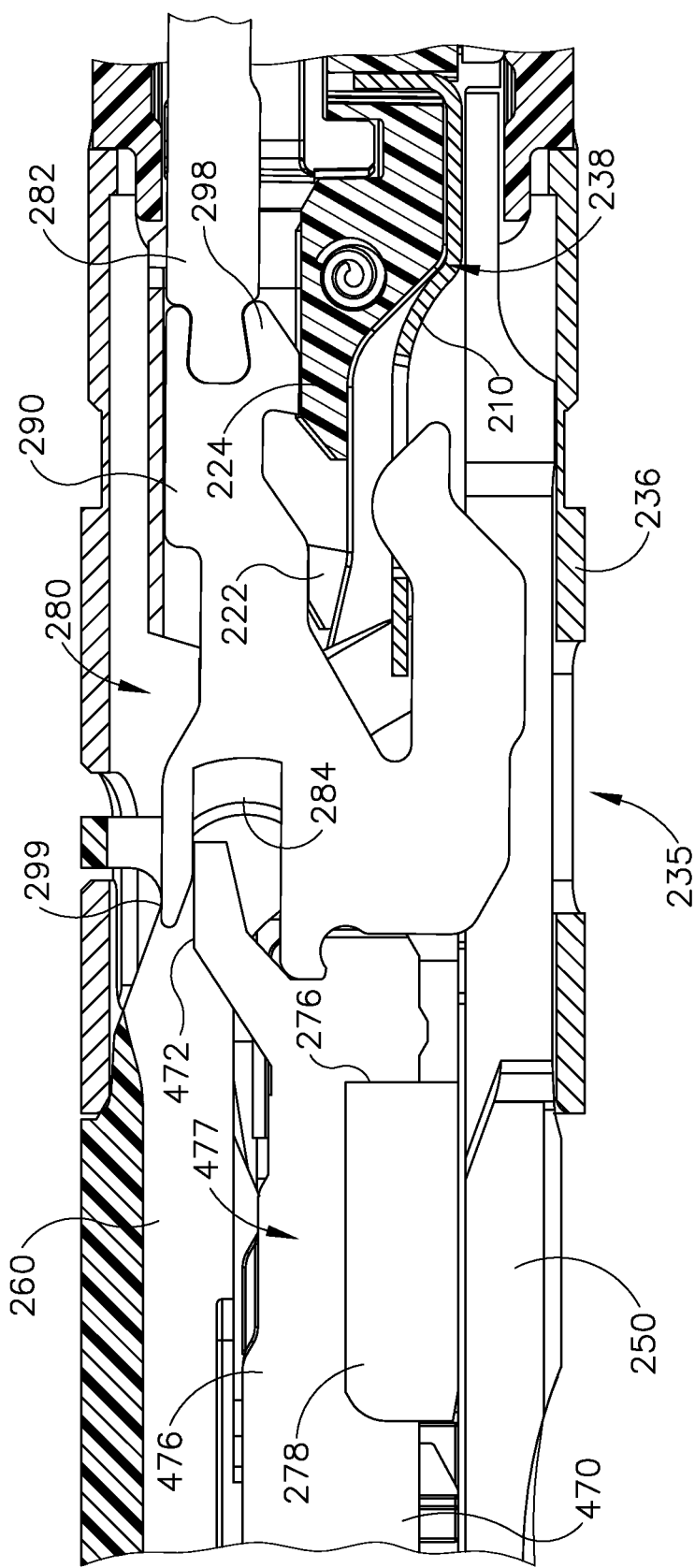
FIG. 46 depicts a cross-sectional side view of the proximal end of the cartridge of FIG. 44A disposed within the end effector of FIG. 13.
Figure 47:
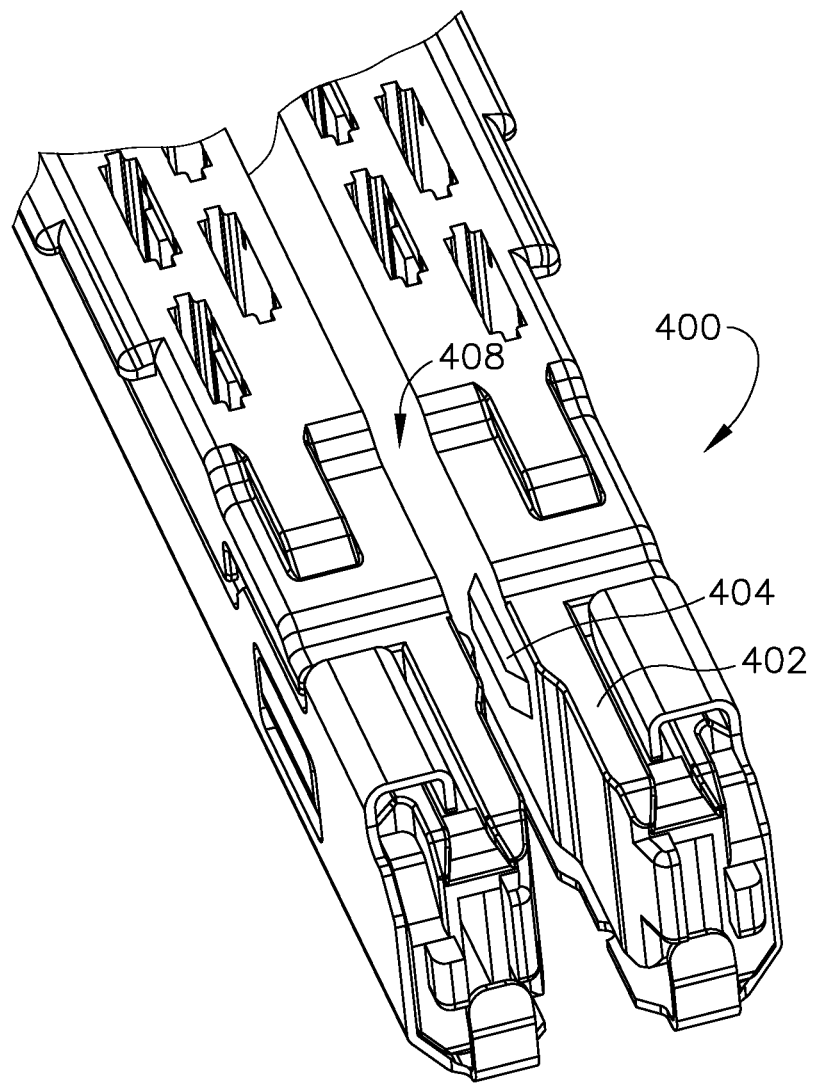
FIG. 47 depicts a perspective view of the proximal end of yet another exemplary alternative cartridge that may be incorporated into the end effector of FIG. 13.
Figure 48:
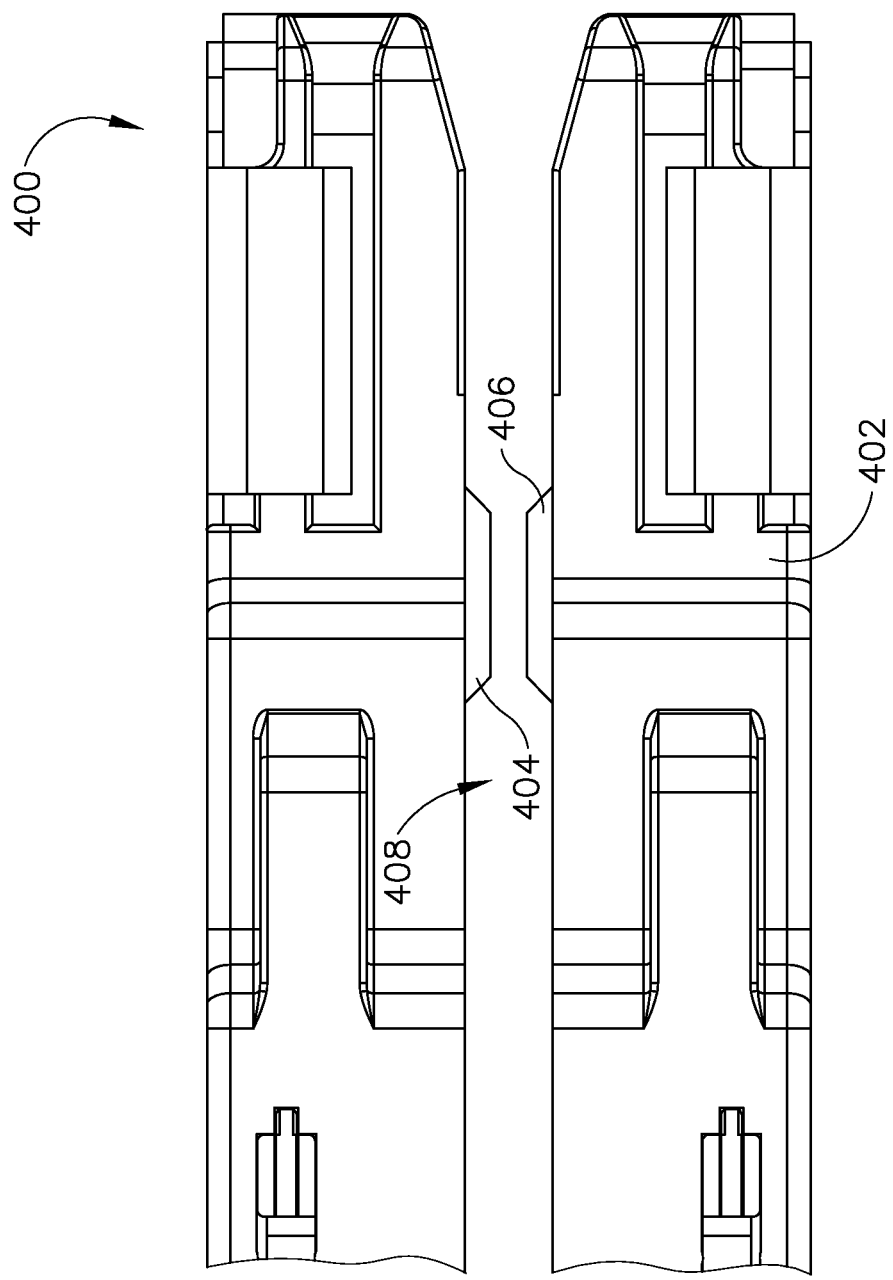
FIG. 48 depicts a top view of the proximal end of the cartridge of FIG. 47.

FIG. 46 shows end effector (240) in an initial position. In the initial position, upper extension (290) of knife member (280) is positioned above engagement features (222, 224) of frame member (238). Also in the initial position, a distal protrusion (299) of knife member (280) is in contact with a top surface of pins (468) of cartridge (460) or fins (472, 474) of cartridge (470). (Although cartridge (470) is being discussed in the present example, it should be appreciated that cartridge (460) may alternatively be used.) As knife member (280) is fired distally, distal protrusion (299) of knife member (280) continues to engage the top surface of pins (468) or fins (472, 474) so as to maintain the vertical position of knife member (280). Because pins (468) or fins (472, 474) maintain the vertical position of knife member (280), tab (298) of knife member (280) translates distally above engagement features (222, 224) of frame member (238) such that tab (298) does not fall between engagement features (222, 224) to prevent the distal movement of knife member (280). As knife member (280) is fired further distally, knife member (280) breaks and/or cuts pins (468) or drives fins (472, 474) outwardly into the open position as knife member (280) drives wedge sled (278) distally as described above. After knife member (280) is fired distally, knife member (280) may be retracted proximally within lower jaw (250). If an operator attempts to fire knife member (280) a second time, without pins (468) or fins (472, 474) to maintain the vertical position of knife member (280), resilient member (210) will resiliently drive knife member (280) downwardly to the lockout position as discussed above with reference to FIG. 23B.

IV. EXEMPLARY PERMANENT LOCKOUT BYPASS FEATURES IN CARTRIDGE

In some instances, it may be desirable to provide other features in a staple cartridge (270) that enable the knife member (280) to bypass lockout features (222, 224) of frame member (238) discussed above to thereby allow continuous firing (i.e. distal advancement) of firing beam (282) and knife member (280) so that tissue positioned between anvil (260) and lower jaw (250) may be severed and stapled. For example, such a feature may prevent knife member (280) from engaging the lockout features of frame member (238) discussed above upon being fired. The examples below include several merely illustrative versions of lockout bypass features that may be readily incorporated into a staple cartridge (270) that is coupled with an end effector such as end effector (240). The examples discussed below provide a lockout bypass in lieu of having wedge sled (278) provide a lockout bypass as discussed above. The examples discussed below are also permanent, permitting re-firing of firing beam (282) and knife member (280) through a spent staple cartridge (270).

A. Exemplary Cartridge Body with Projections

FIGS. 47-49B show an exemplary staple cartridge (400) having a lockout bypass feature. It should be understood that cartridge (400) may be readily used in end effector (240) or in other end effectors. Cartridge (400) of the present example is configured to operate substantially similar to cartridges (70, 270) discussed above except for the differences discussed below. Cartridge (400) includes a cartridge body (402) having a longitudinal channel (408) through which wedge sled (278) and knife member (280) may be longitudinally translated. The lockout bypass feature of the present example comprises a pair of inwardly extending projections (404, 406) extending inwardly from opposing interior surfaces of channel (408) of cartridge body (402). Projections (404, 406) are configured to engage distal tip (297) of knife member (280) as knife member (280) is fired; yet projections (404, 406) provide enough clearance for knife member (280) to translate longitudinally through channel (408) of cartridge (400). As will be discussed in more detail below, projections (404, 406) are configured to allow for firing of knife member (280) by preventing engagement of knife member (280) with the lockout features of frame member (238) as discussed above.

Figure 49A:
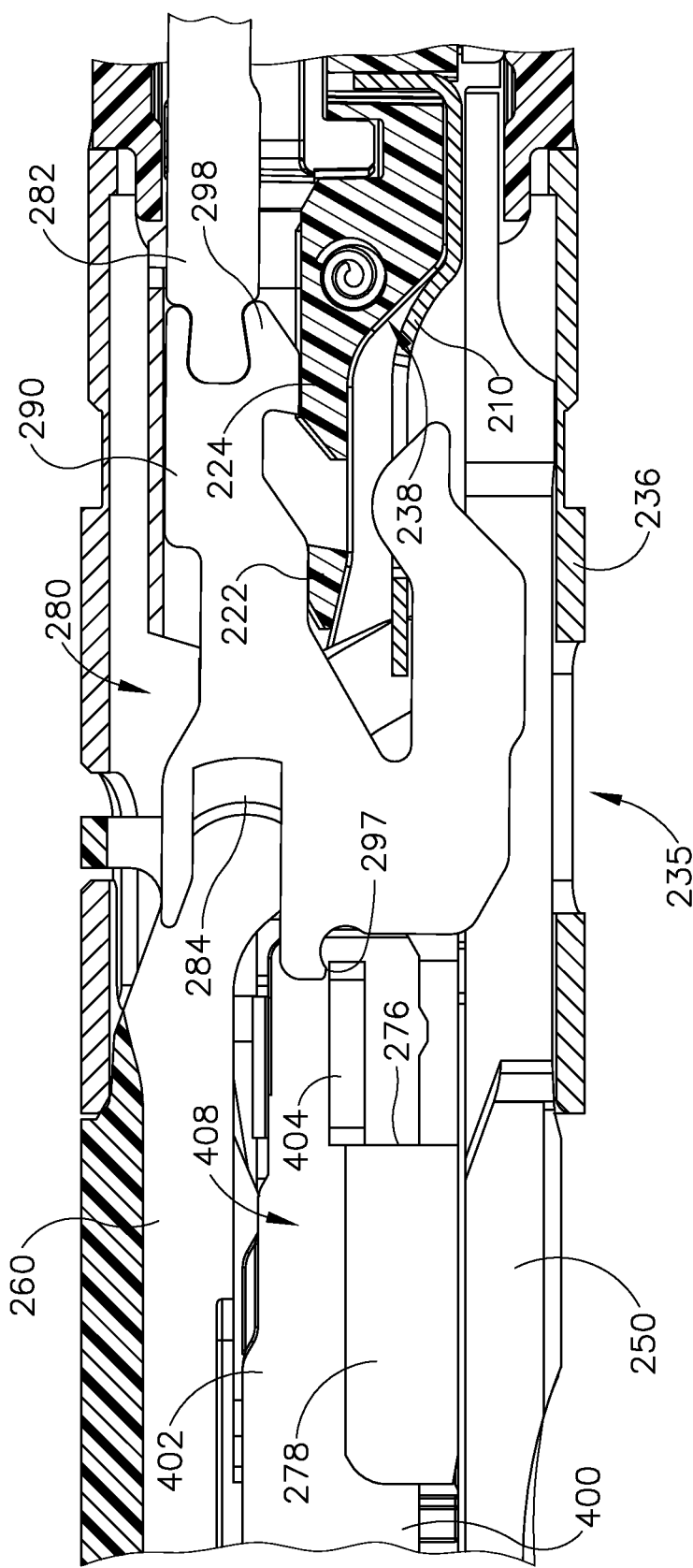
FIG. 49A depicts a cross-sectional view of the proximal end of the cartridge of FIG. 47 disposed within the end effector of FIG. 13, with a knife of the end effector in a first longitudinal position.
Figure 49B:
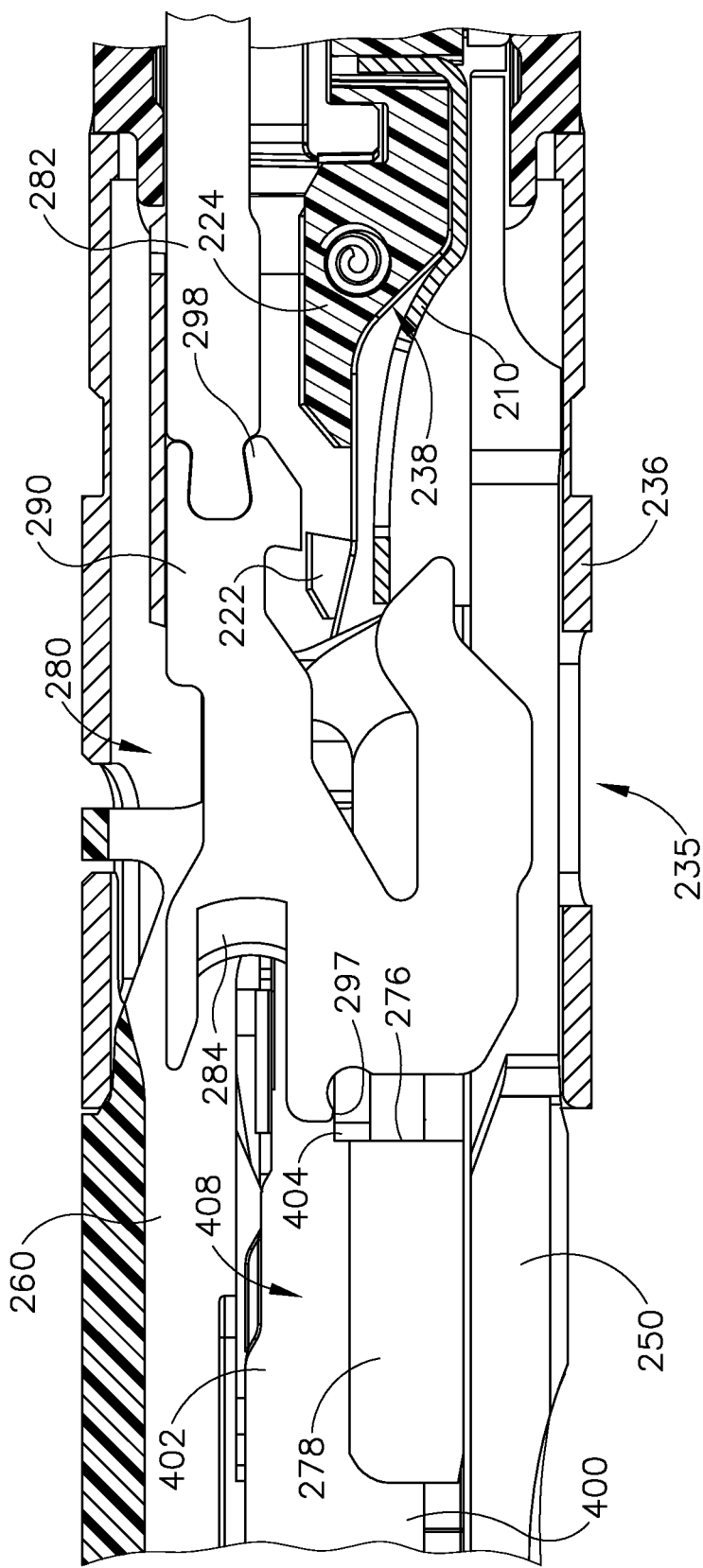
FIG. 49B depicts a cross-sectional view of the proximal end of the cartridge of FIG. 47 disposed within the end effector of FIG. 13, with the knife of the end effector moved into a second longitudinal position.
Figure 50:
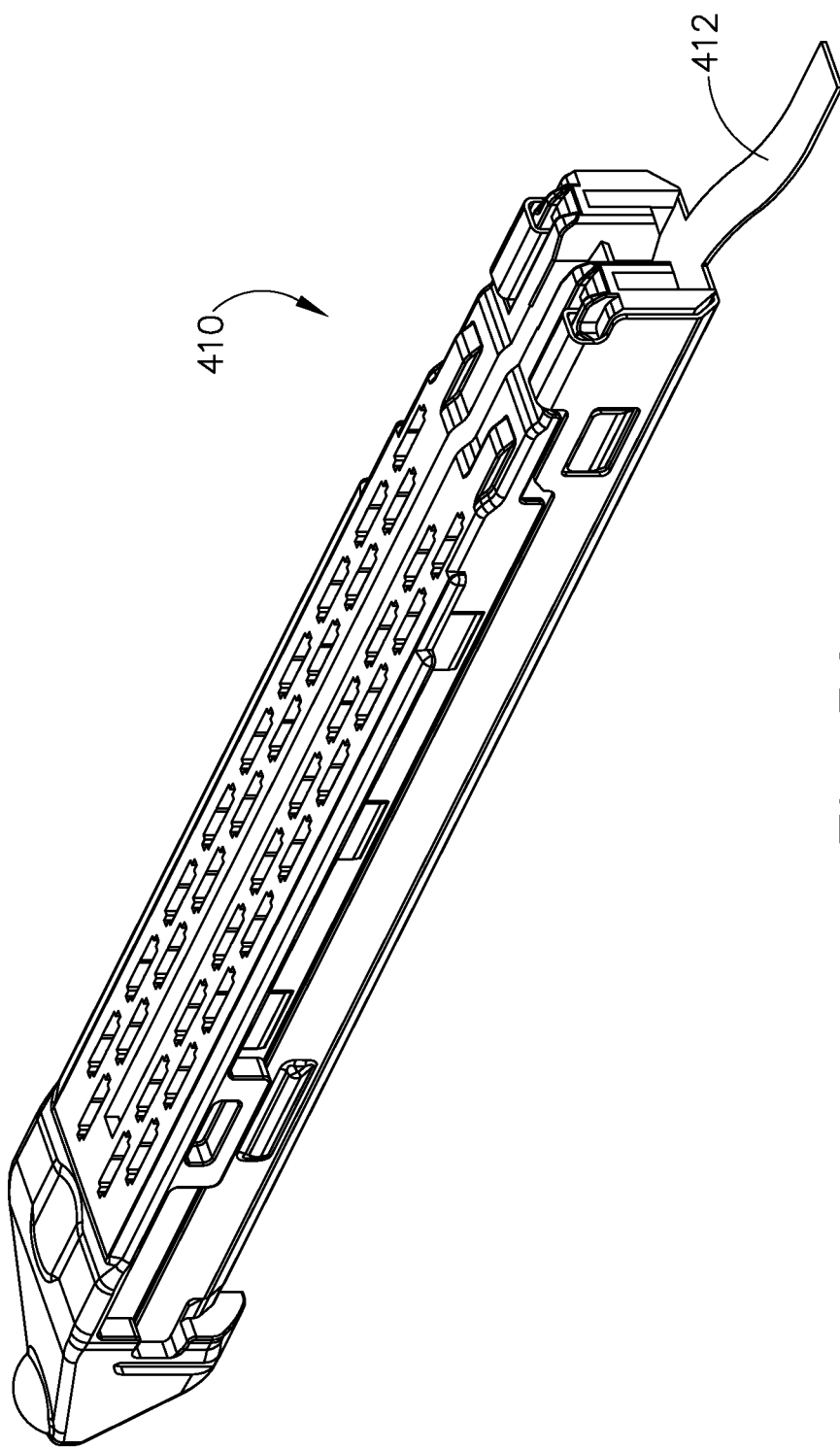
FIG. 50 depicts a perspective view of yet another exemplary alternative cartridge that may be incorporated into the end effector of FIG. 13.
Figure 51:
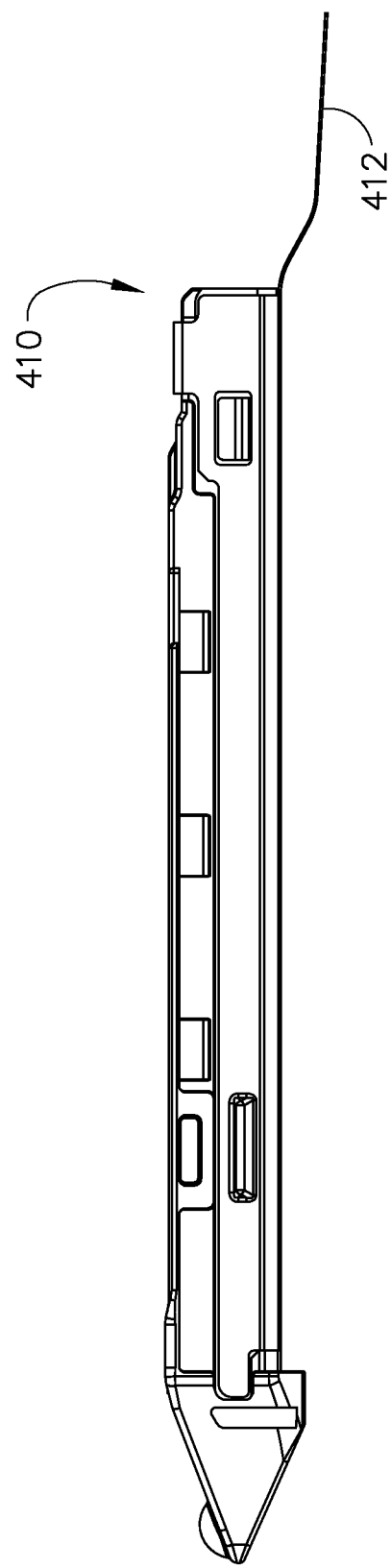
FIG. 51 depicts a side view of the cartridge of FIG. 50.
Figure 52:
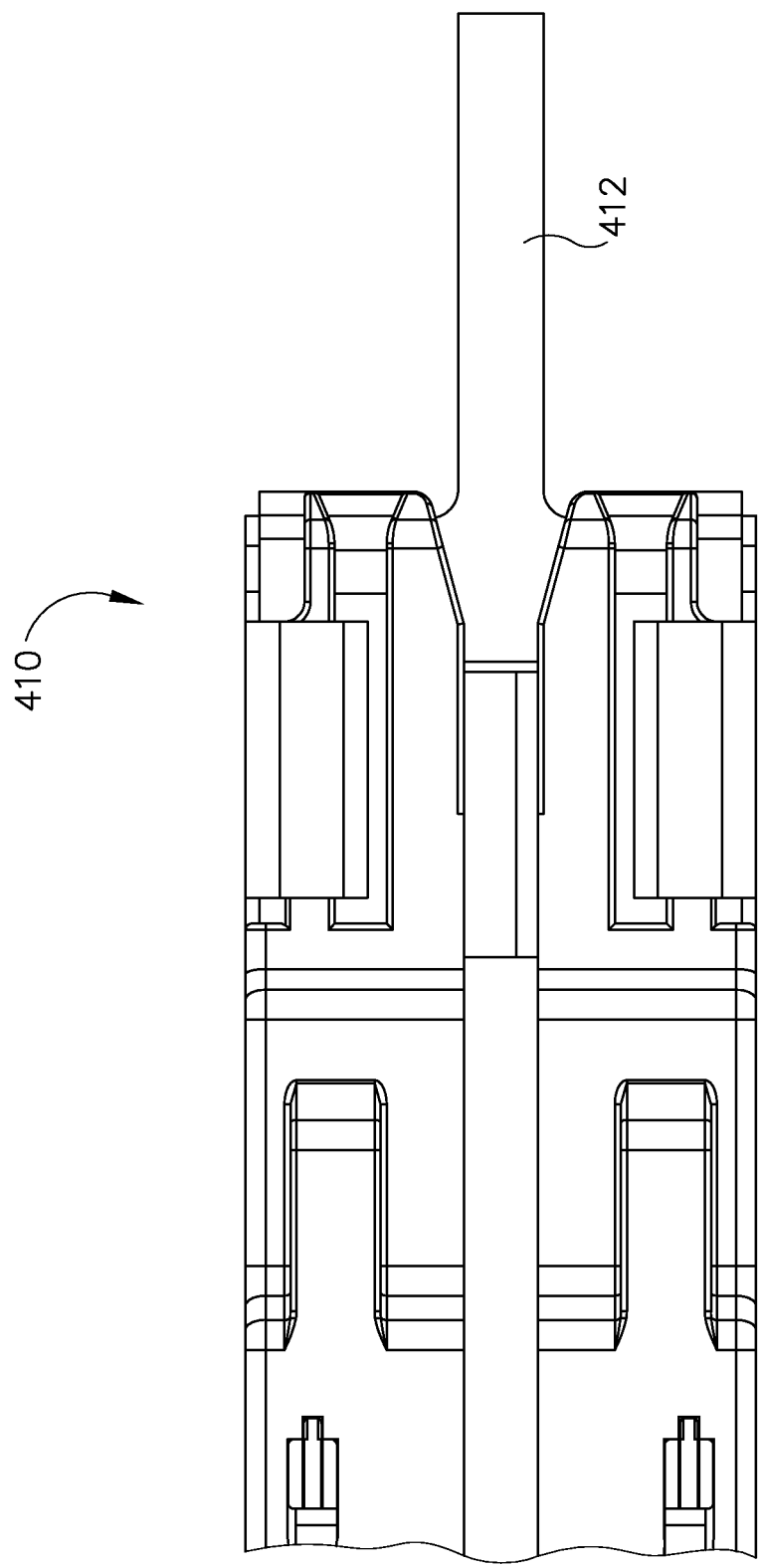
FIG. 52 depicts a top view of the proximal end of the cartridge of FIG. 50.

FIG. 49A shows end effector (240) in an initial position. In the initial position, upper extension (290) of knife member (280) is positioned above engagement features (222, 224) of frame member (238). As knife member (280) is fired distally to the position shown in FIG. 49B, distal tip (297) of knife member (280) engages a top surface of one or both projections (404, 406). Engagement between distal tip (297) and one or both projections (404, 406) maintains the vertical position of knife member (280). Because one or both projections (404, 406) maintain the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280).

B. Exemplary Cartridge with Proximal Ramp

Figure 53:
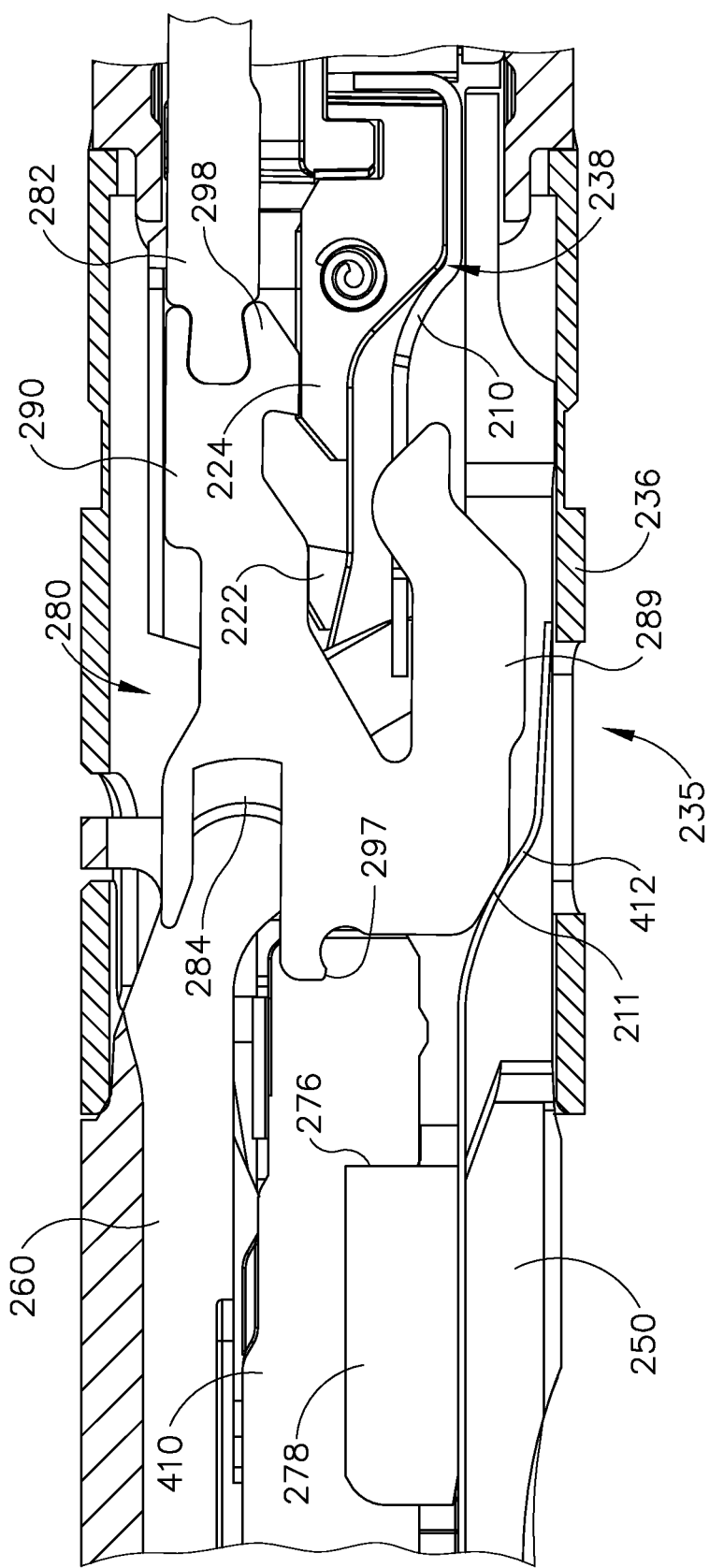
FIG. 53 depicts a cross-sectional view of the proximal end of the cartridge of FIG. 50 disposed within the end effector of FIG. 13.
Figure 54:
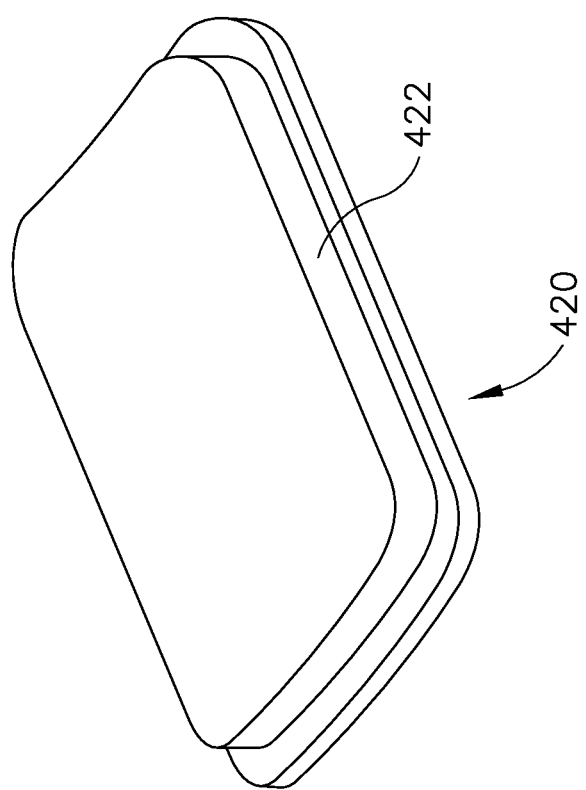
FIG. 54 depicts a perspective view of an exemplary tab insert.
Figure 55B:
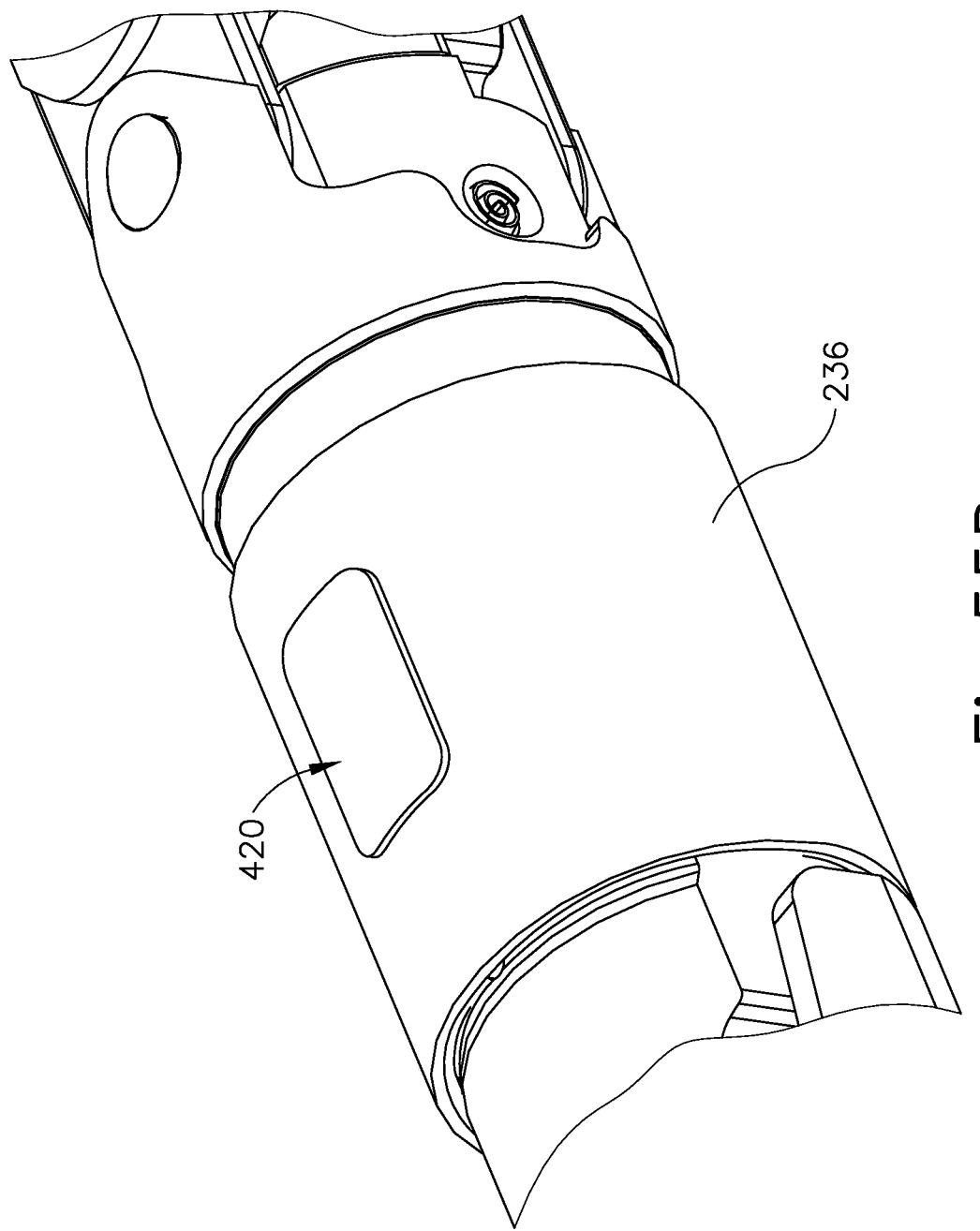
FIG. 55B depicts a perspective view of the end effector of FIG. 13, with the tab insert of FIG. 54 positioned within the end effector.

FIGS. 50-53 show another exemplary staple cartridge (410) having a lockout bypass feature. It should be understood that cartridge (410) may be readily used in end effector (240) or in other end effectors. Cartridge (410) of the present example is configured to operate substantially similar to cartridges (70, 270) discussed above except for the differences discussed below. The lockout bypass feature of the present example comprises a resilient ramp (412) extending proximally from a proximal end of cartridge (410). Ramp (412) is configured to engage ramped wall (211) and/or tab (289) of knife member (280) as knife member (280) is fired distally. Ramp (412) is configured to allow for firing of knife member (280) by preventing engagement of knife member (280) with the lockout features of frame member (238) as discussed above upon being fired. In particular, as shown in FIG. 53, with cartridge (410) positioned within lower jaw (250), ramp (410) covers opening (235) of closure ring (236) and provides a surface operable to engage ramped wall (211) and/or tab (289) of knife member (280) as knife member (280) is fired. As knife member (280) is fired distally, ramped wall (211) and/or tab (289) of knife member (280) engages a top surface of ramp (412). Engagement between ramped wall (211) and/or tab (289) and ramp (412) maintains the vertical position of knife member (280). Because ramp (412) maintains the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280).

It should also be understood that a variation of cartridge (410) may be used in other kinds of surgical staplers. By way of example only, a variation of cartridge (410) may be used in any of the various surgical staplers disclosed in U.S. Pat. No. 7,380,695, entitled "Surgical Stapling Instrument Having a Single Lockout Mechanism for Prevention of Firing," issued Jun. 3, 2008, the disclosure of which is incorporated by reference herein. For instance, ramp (412) may engage the "middle pin 46" of the "firing bar 14" of that stapler, such that the "middle pin 46" rides along the top surface of ramp (412). This may provide a bypass of a lockout assembly as taught in that reference, such that ramp (412) enables the "firing bar 14" to advance distally without being locked out. Various other suitable ways in which ramp (412) and other lockout bypass features described herein may be incorporated into other stapling instruments will be apparent to those of ordinary skill in the art in view of the teachings herein.

Figure 56A:
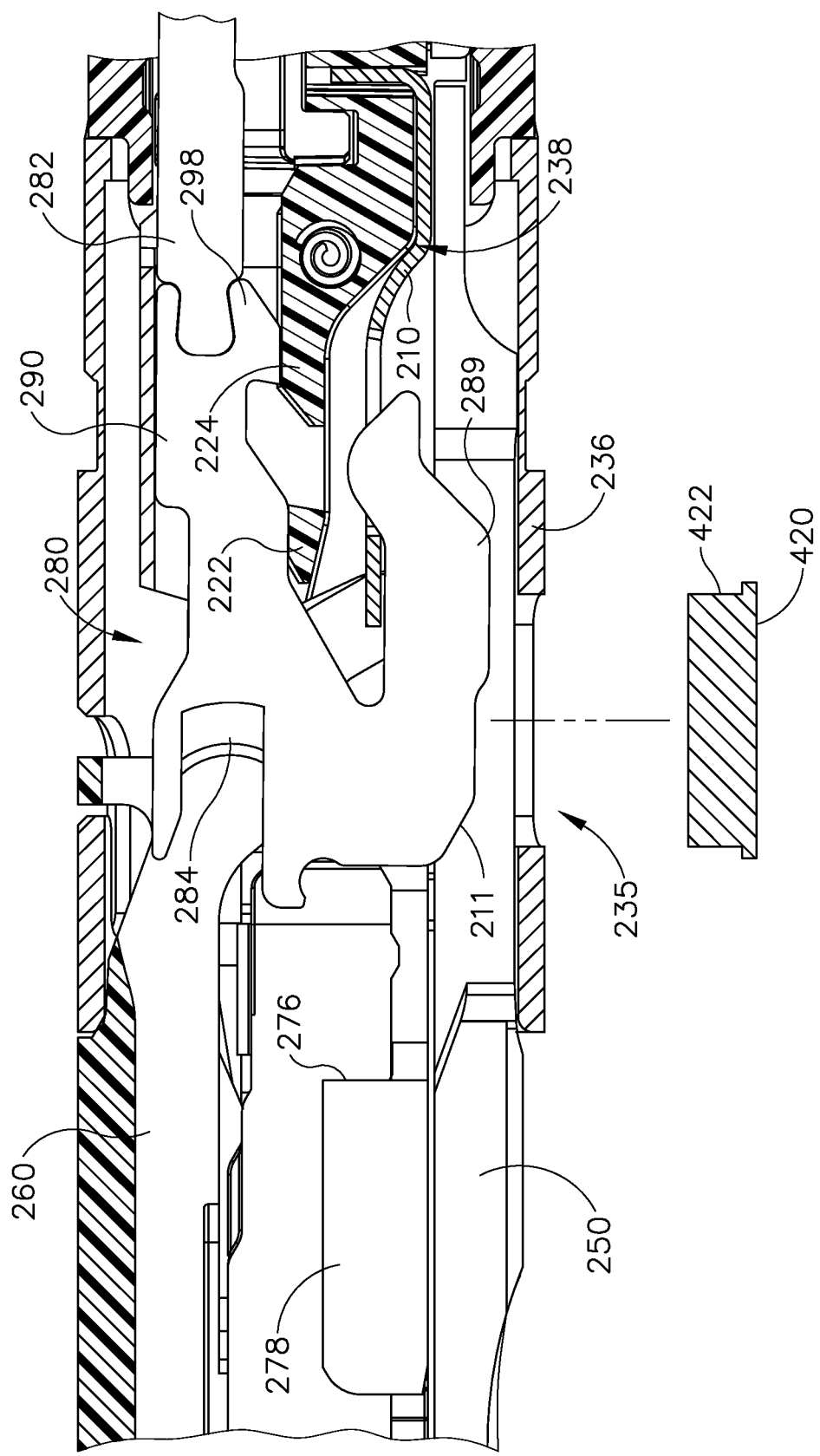
FIG. 56A depicts a cross-sectional side view of the end effector of FIG. 13, with the tab insert of FIG. 54 positioned to couple with the end effector.
Figure 56B:
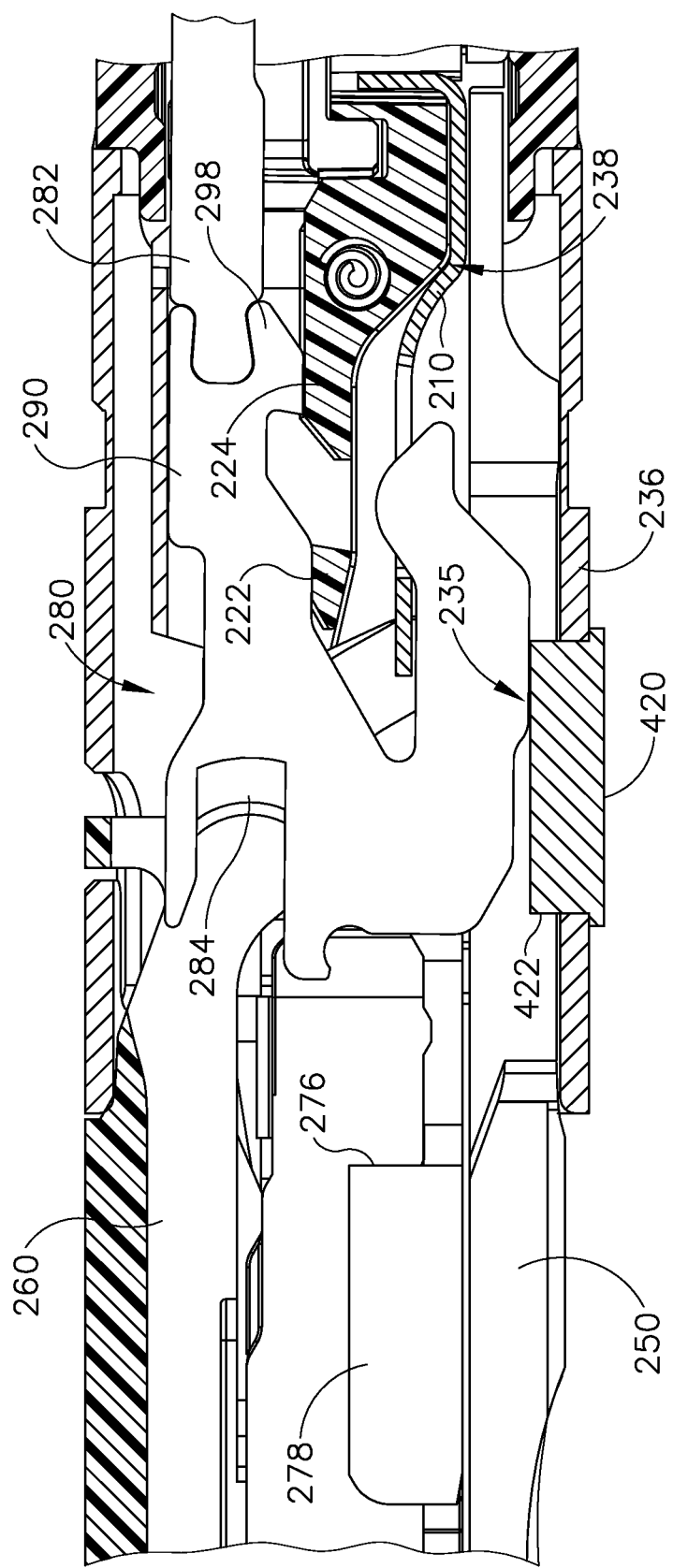
FIG. 56B depicts a cross-sectional side view of the end effector of FIG. 13, with the tab insert of FIG. 54 positioned within the end effector.

FIGS. 54-56B show another exemplary lockout bypass feature. The lockout bypass feature of the present example comprises a snap-fit cover (420). Cover (420) is configured to engage tab (289) of knife member (280) as knife member (280) is fired. Cover (420) is configured to allow for firing of knife member (280) by preventing engagement of knife member (280) with the lockout features of frame member (238) as discussed above upon firing of knife member (280). In particular, as best seen in FIGS. 56A and 56B, cover (420) is configured to be positioned within opening (235) of closure ring (236) such that a projection (422) of cover (420) extends inwardly within closure ring (236). As knife member (280) is fired distally, tab (289) of knife member (280) engages a top surface of projection (422) of cover (420). Engagement between tab (289) and projection (422) maintains the vertical position of knife member (280). Because projection (422) maintains the vertical position of knife member (280), tab (289) of knife member (280) translates distally above engagement features (222, 224) of frame member (238) such that resilient member (210) does not drive tab (298) downwardly between engagement features (222, 224) to prevent the distal movement of knife member (280). It should be understood that cover (420) may be readily used in end effector (240) or in other end effectors.

D. Exemplary Snap-Fit Ramp

Figure 57:
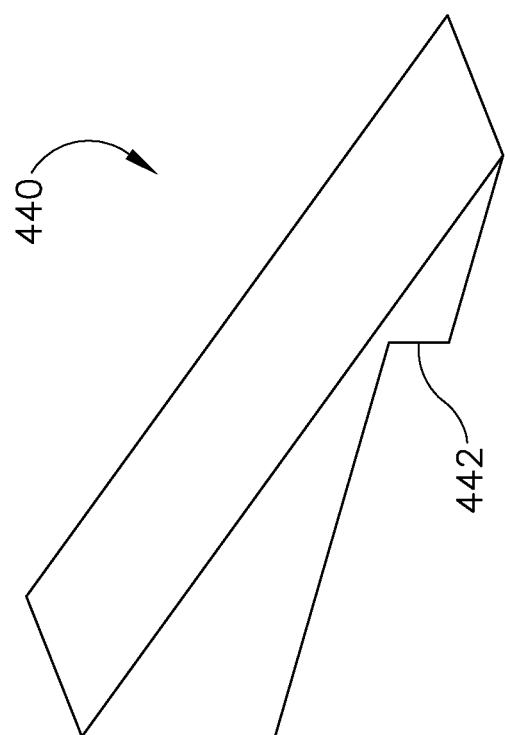
FIG. 57 depicts a perspective view of an exemplary ramp insert.
Figure 58:
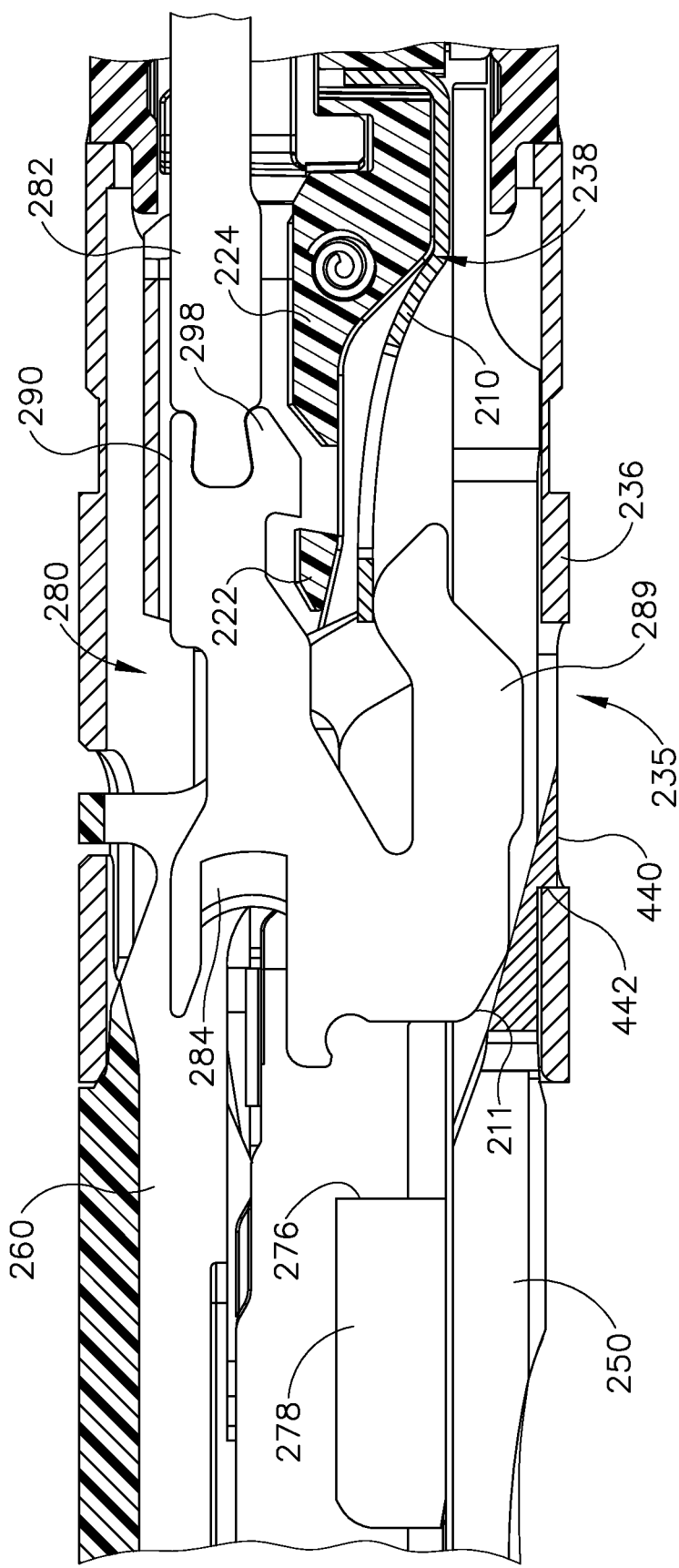
FIG. 58 depicts a cross-sectional side view of the end effector of FIG. 13 with the ramp insert of FIG. 57 positioned within the end effector.

FIGS. 57 and 58 show another exemplary lockout bypass feature. The lockout bypass feature of the present example comprises a snap-fit ramp (440). Ramp (440) is configured to engage ramped wall (211) and/or tab (289) of knife member (280) as knife member (280) is fired. Ramp (440) is configured to allow for firing of knife member (280) by preventing engagement of knife member (280) with the lockout features of frame member (238) as discussed above upon being fired. In particular, as best seen in FIG. 58, ramp (440) is configured to be positioned within opening (235) of closure ring (236) such that ramp (440) extends inwardly within closure ring (236). A step (442) of ramp (440) engages a distal edge of opening (235) to maintain the position of ramp (440) during firing of knife member (280). As knife member (280) is fired distally, ramped wall (211) and/or tab (289) of knife member (280) engages a top surface of ramp (440). Engagement between ramped wall (211) and/or tab (289) and ramp (440) maintains the vertical position of knife member (280). Because ramp (440) maintains the vertical position of knife member (280), tab (298) of knife member (280) translates distally above engagement features (222, 224) of frame member (238) such that resilient member (210) does not drive tab (298) downwardly between engagement features (222, 224) to prevent the distal movement of knife member (280). It should be understood that ramp (440) may be readily used in end effector (240) or in other end effectors.

V. EXEMPLARY FEATURES TO PREVENT USE OF STAPLE CARTRIDGE IN INCORRECT END EFFECTOR

Various surgical stapling instruments are available for purchase and use. These various surgical stapling instruments may use different staple cartridges. In some instances, an operator may have difficulty in immediately discerning which staple cartridge corresponds to which surgical stapling instrument. An operator may therefore inadvertently place and attempt to use a staple cartridge in an incorrect surgical stapling device. Thus, it may be desirable to provide features that prevent a staple cartridge that is intended to be used in one particular surgical stapling instrument from being used in other, incorrect surgical stapling instruments. For instance, such features may prevent insertion of an improper staple cartridge and/or may prevent firing of a knife member or a firing beam in the presence of an incorrect staple cartridge. The example below includes merely illustrative versions of features that may be readily introduced to any of the cartridges discussed above.

A. Exemplary End Effector with "E-Beam"

Some surgical stapling instruments may include an "E-Beam" type of knife member or firing beam, instead of including a structure like the combination of knife member (80, 280) and firing beam (82, 282) described above. An example of such a stapling instrument (710) is shown in FIGS. 59-69. Instrument (710) comprises an end effector (740) having an E-beam firing mechanism ("firing bar") (714) that controls the spacing of the end effector (740). In particular, a lower jaw (716) and a pivotally translatable anvil (760) are maintained at a spacing that assures effective stapling and cutting.

Instrument (710) includes a handle portion (720) connected to a shaft assembly (722), shaft assembly (722) comprising a shaft (723) distally terminating in end effector (740). Handle portion (720) includes a pistol grip (724) toward which a closure trigger (726) is pivotally drawn by the operator to cause clamping, or closing, of anvil (760) toward lower jaw (716) of end effector (740). A firing trigger (728) is farther outboard of closure trigger (726) and is pivotally drawn by the operator to cause the stapling and cutting of clamped tissue in end effector (740). A closure sleeve (732) encloses a frame (734), which in turn encloses a firing drive member (736) that is positioned by firing trigger (728). Frame (734) connects handle portion (720) to end effector (740). With closure sleeve (732) withdrawn proximally by closure trigger (726) as depicted, anvil (760) springedly opens, pivoting away from lower jaw (716) and translating proximally with closure sleeve (732).

Figure 60:
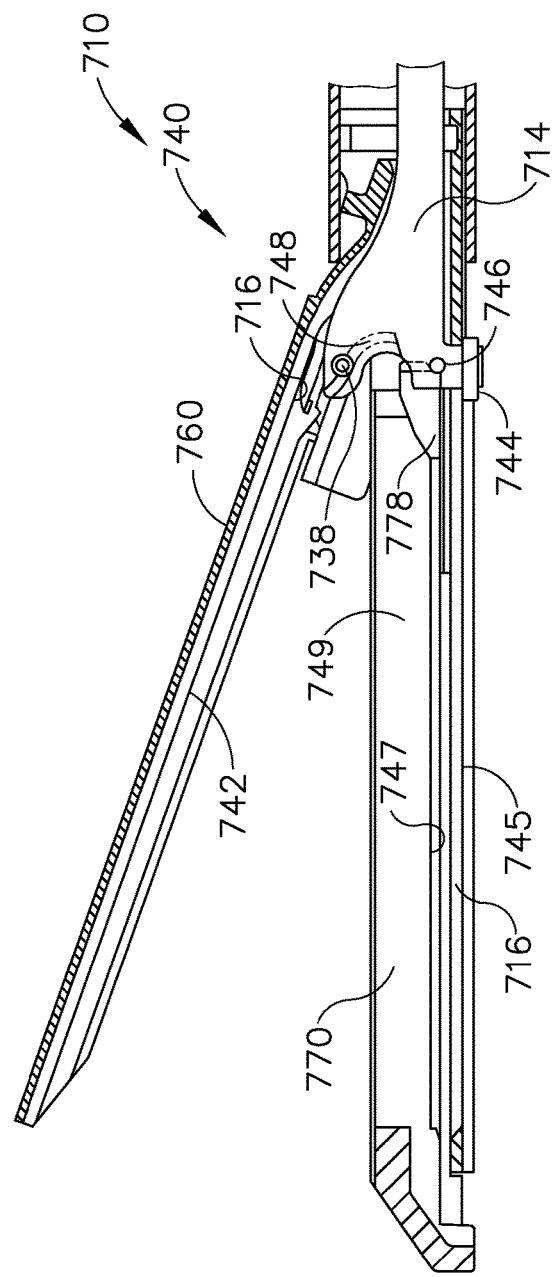
FIG. 60 depicts a cross-sectional side view of an end effector of the instrument of FIG. 59.
Figure 61:
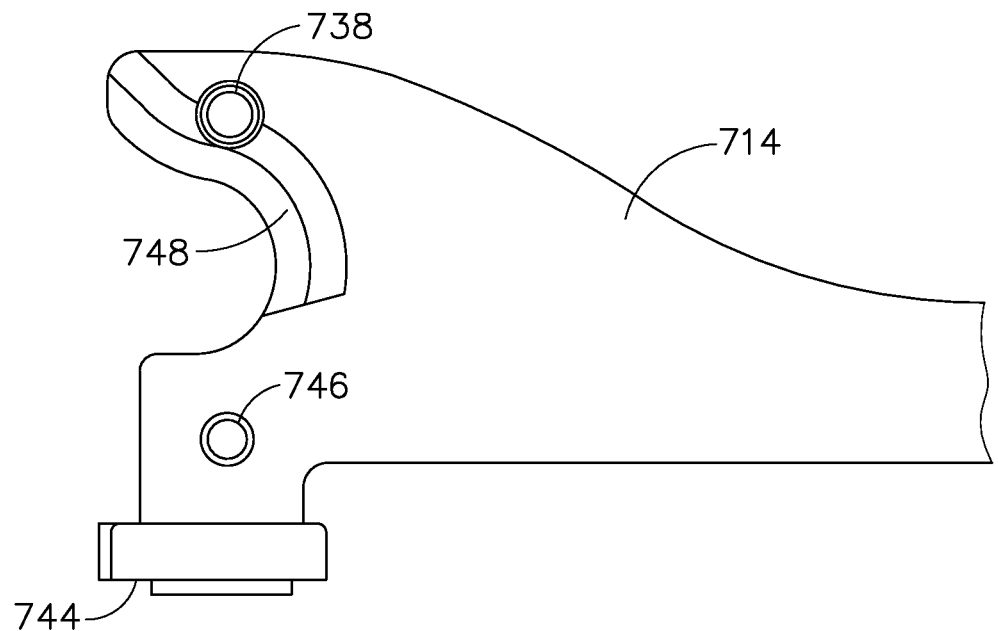
FIG. 61 depicts a side elevation view of a firing bar of the surgical instrument of FIG. 59.
Figure 62:
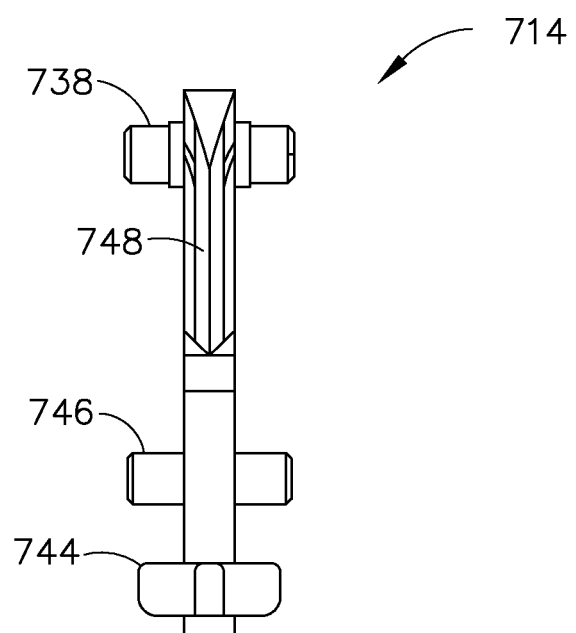
FIG. 62 depicts a front elevational iew of the firing bar of FIG. 61.

As shown in FIGS. 60-62, firing bar (714) includes three vertically spaced pins (738, 744, 746) that control the spacing of end effector (740) during firing. In particular, an upper pin (738) is staged to enter an anvil pocket (716) near the pivot between anvil (760) and lower jaw (716). When fired with anvil (760) closed, the upper pin (738) advances distally within a longitudinal anvil slot (742) extending distally through anvil (760). Any minor upward deflection in anvil (760) is overcome by a downward force imparted by upper pin (738). Firing bar (714) also includes a lower most pin, or firing bar cap (744), that upwardly engages a channel slot (745) in lower jaw (716), thereby cooperating with upper pin (738) to draw anvil (760) and lower jaw (716) slightly closer together in the event of excess tissue clamped therebetween.

Firing bar (714) further includes a middle pin (746) that passes through a firing drive slot (747) formed in a lower surface of cartridge (770) and an upward surface of lower jaw (716), thereby driving the staples therein. Middle pin (746), by sliding against lower jaw (716), resists any tendency for end effector (740) to be pinched shut at its distal end. A distally presented cutting edge (748) between upper and middle pins (738, 746) on firing bar (714) traverses through a proximally presented, vertical slot (749) in cartridge (770) to cut clamped tissue. The affirmative positioning of firing bar (714) with regard to lower jaw (716) and anvil (760) assure that an effective cut is performed.

Figure 59:
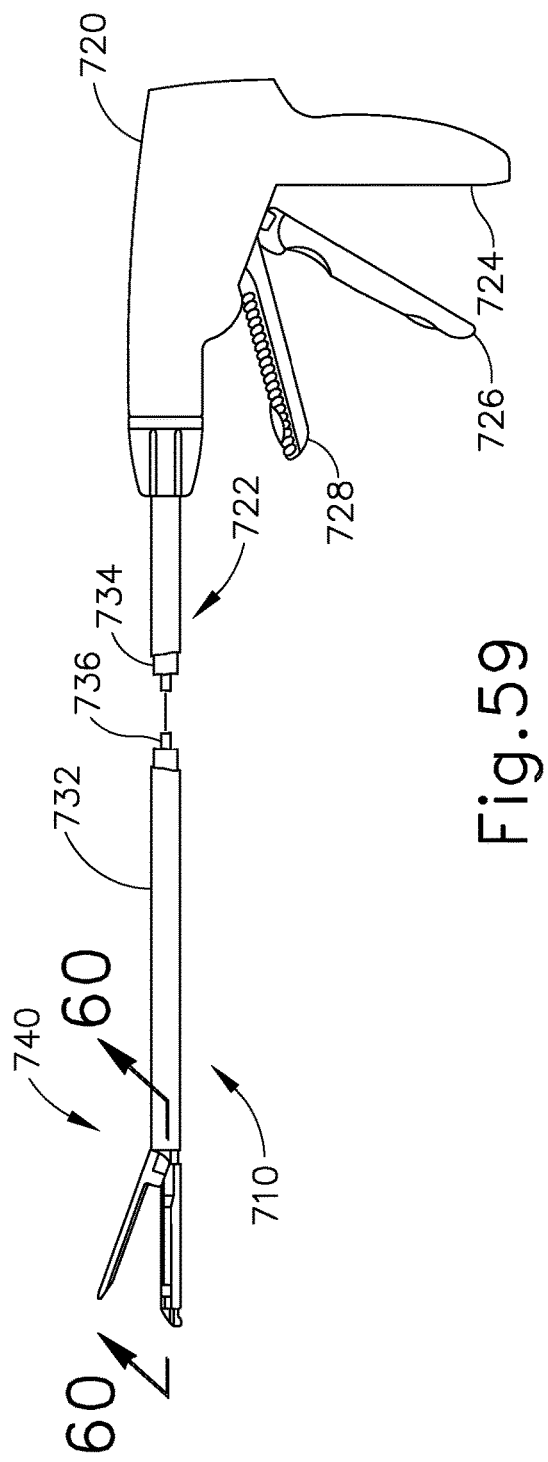
FIG. 59 depicts a side elevation view of an exemplary alternative surgical stapling instrument.
Figure 63:
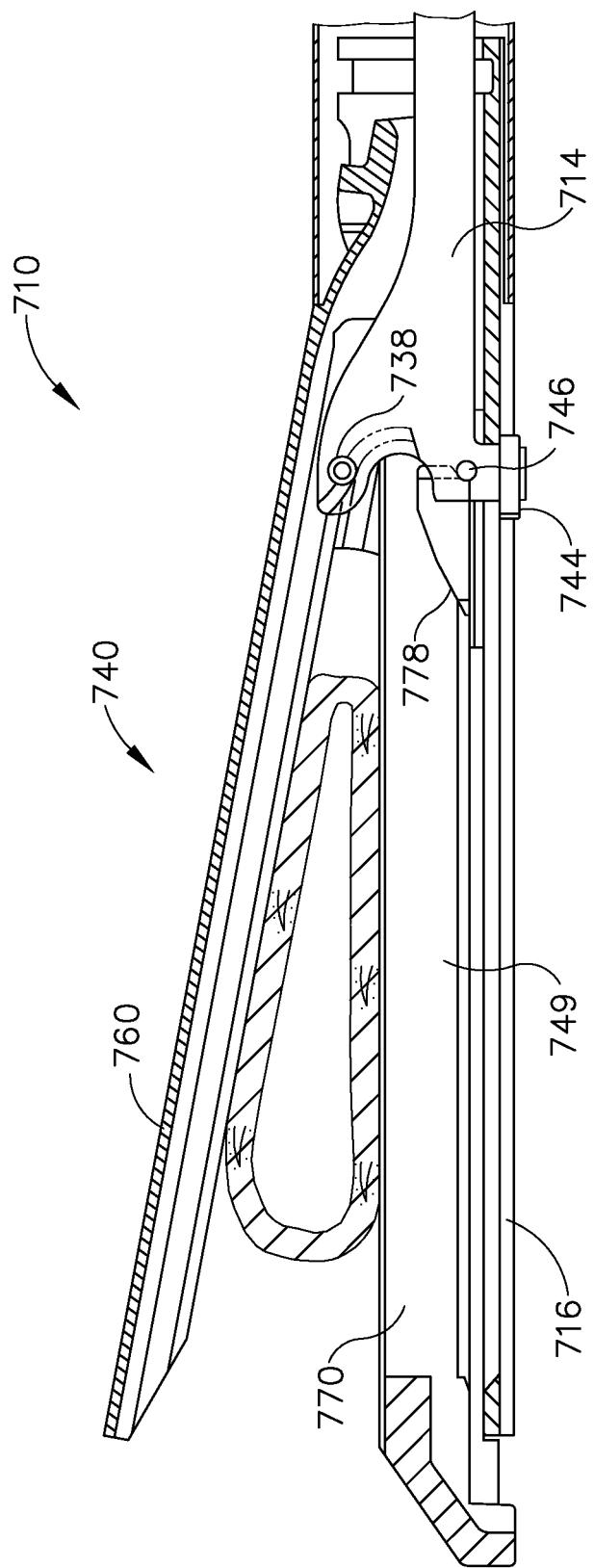
FIG. 63 depicts a cross-sectional side view of the end effector of FIG. 60 in a partially closed but unclamped position gripping tissue.

An exemplary use of instrument (710) is depicted in FIGS. 59, 60, and 63-69. In FIGS. 59 and 60, instrument (710) is in its start position, having had an unfired, fully loaded staple cartridge (770) snap-fitted into the distal end of lower jaw (716). Both triggers (726, 728) are forward and end effector (740) is open. Instrument (710) is then manipulated by the operator such that tissue to be stapled and severed is positioned between staple cartridge (770) and anvil (760), as depicted in FIG. 63. As shown in FIGS. 64 and 65, the operator moves closure trigger (726) proximally until positioned directly adjacent to pistol grip (724). With anvil (760) closed and clamped, firing bar (714) is aligned for firing through end effector (740). In particular, upper pin (738) is aligned with anvil slot (742) and lower jaw (716) is affirmatively engaged about channel slot (745) by middle pin (746) and firing bar cap (744).

As shown in FIGS. 66 and 67, after tissue clamping has occurred, the operator moves firing trigger (728) proximally causing firing bar (714) to move distally into end effector (740). In particular, middle pin (746) enters staple cartridge (770) through firing drive slot (747) to effect firing of staples (790) (not shown in FIGS. 66 and 67) via a wedge sled (778) toward anvil (760). Lower most pin, or firing bar cap (744), cooperates with middle pin (746) to slidingly position cutting edge (748) of firing bar (714) to cut tissue. The two pins (744, 746) also position upper pin (738) of firing bar (714) within longitudinal anvil slot (742) of anvil (760), affirmatively maintaining the spacing between anvil (760) and lower jaw (716) throughout its distal firing movement.

Figure 68:
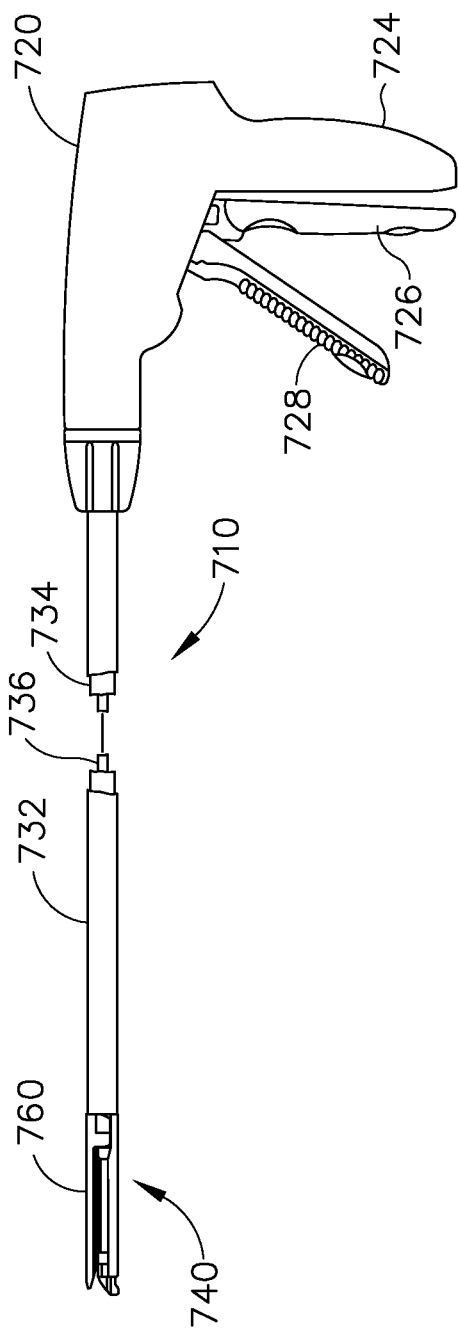
FIG. 68 depicts a side view of the surgical stapling instrument of FIG. 59 in a fully fired position.
Figure 69:
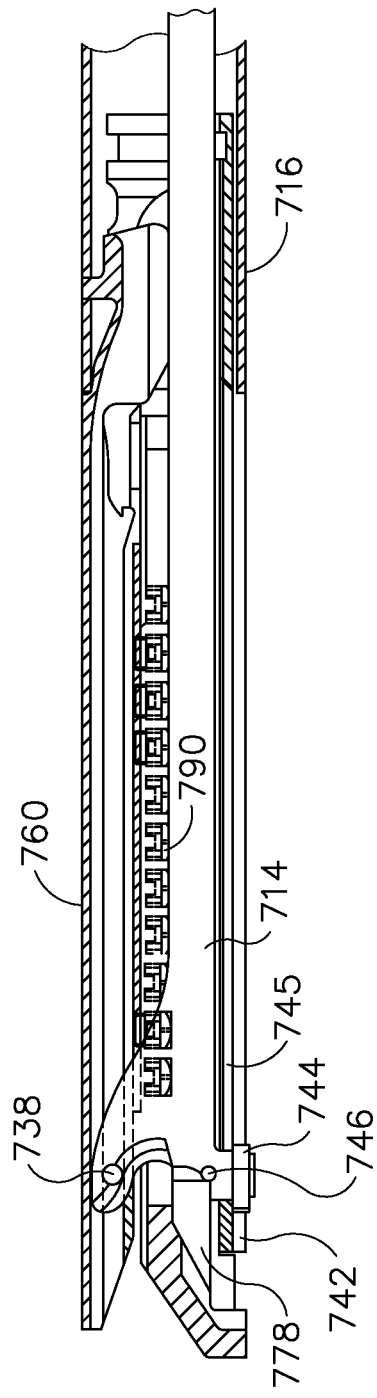
FIG. 69 depicts a cross-sectional side view of the end effector of FIG. 60 in the fully fired position.

With reference to FIGS. 68 and 69, the operator continues moving firing trigger (728) until brought proximal to closure trigger (726) and pistol grip (724). Thereby, all of the ends of staples (790) are bent over as a result of their engagement with anvil (760). Firing bar cap (744) is arrested against a firing bar stop (792) projecting toward the distal end of channel slot (745). Cutting edge (748) has traversed completely through the tissue.

It should be understood that instrument (710) of the present example may be further constructed and/or operable in accordance with at least some of the teachings of U.S. Pat. No. 7,380,695, entitled "Surgical Stapling Instrument Having a Single Lockout Mechanism for Prevention of Firing," issued Jun. 3, 2008, the disclosure of which is incorporated by reference herein.

B. Exemplary Lockout to Prevent Use of Staple Cartridge in E-Beam End Effector In some instances, it may be desirable to provide lockout features that prevent firing of firing bar (714) of instrument (710) if an inappropriate staple cartridge is inserted into end effector (740). Accordingly, lockout features may be provided on a staple cartridge that is not intended to be used with instrument (710) to thereby prevent firing of firing bar (714).

Figure 70:
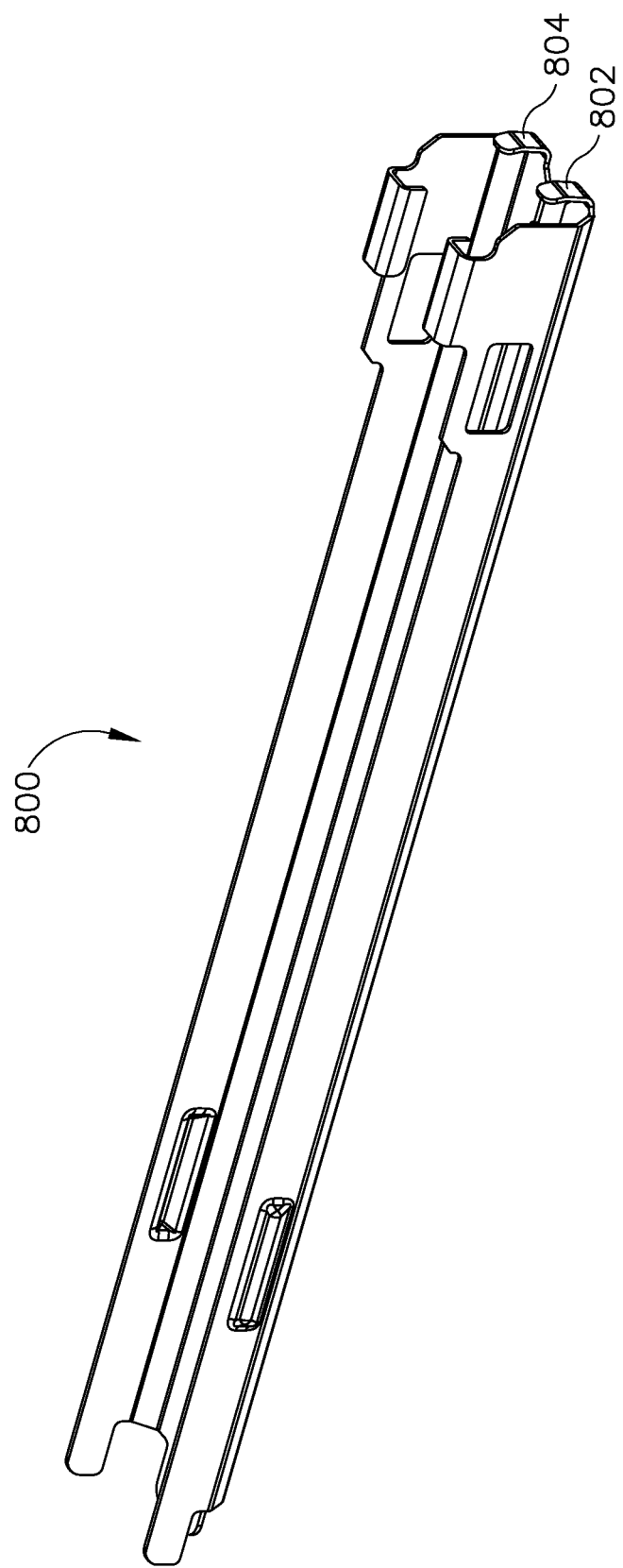
FIG. 70 depicts a perspective view of an exemplary alternative cartridge tray that may be incorporated into the cartridge of the end effector of FIG. 13.
Figure 71:
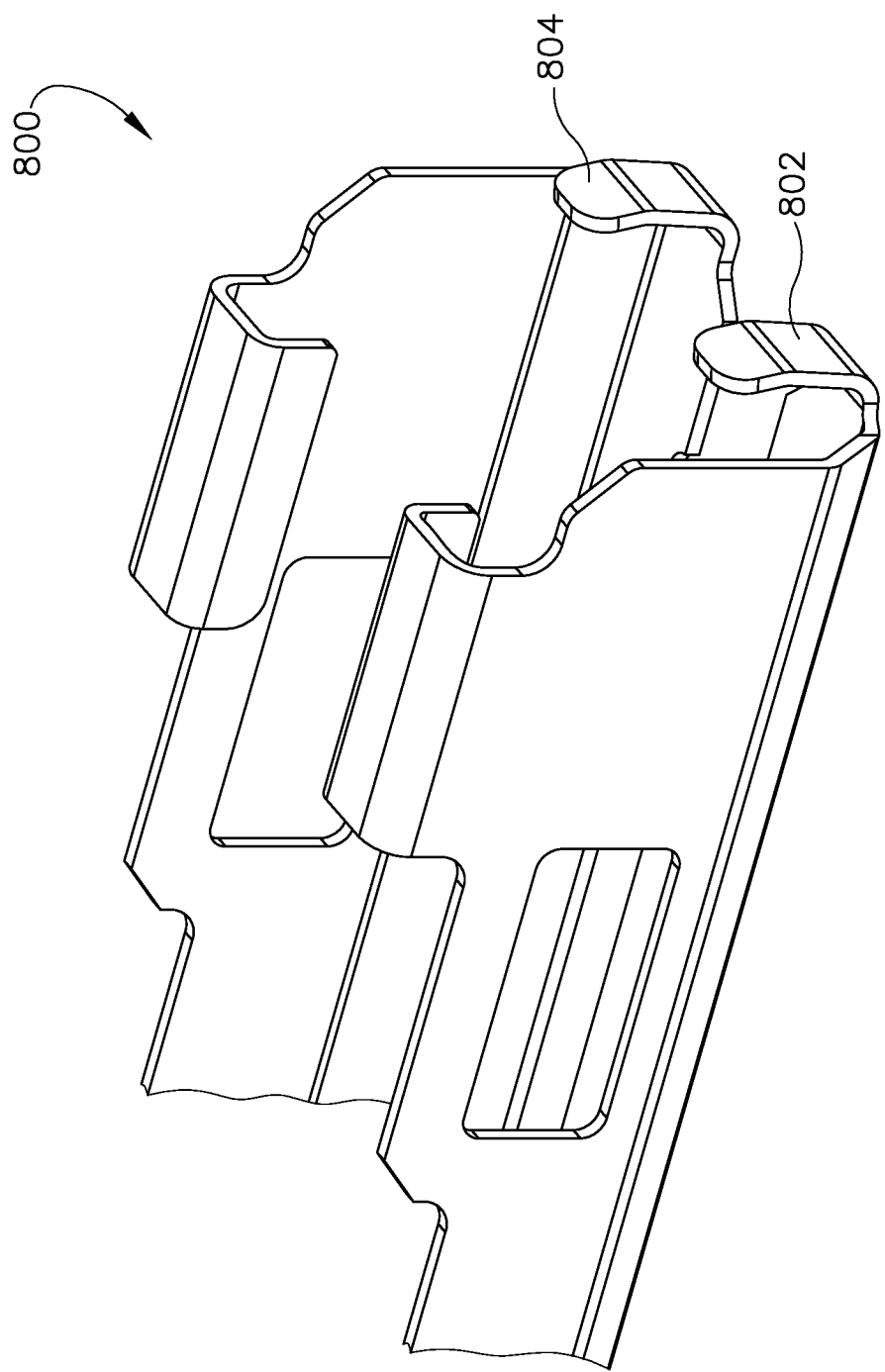
FIG. 71 depicts a detailed perspective view of the proximal end of the cartridge tray of FIG. 70.
Figure 72:
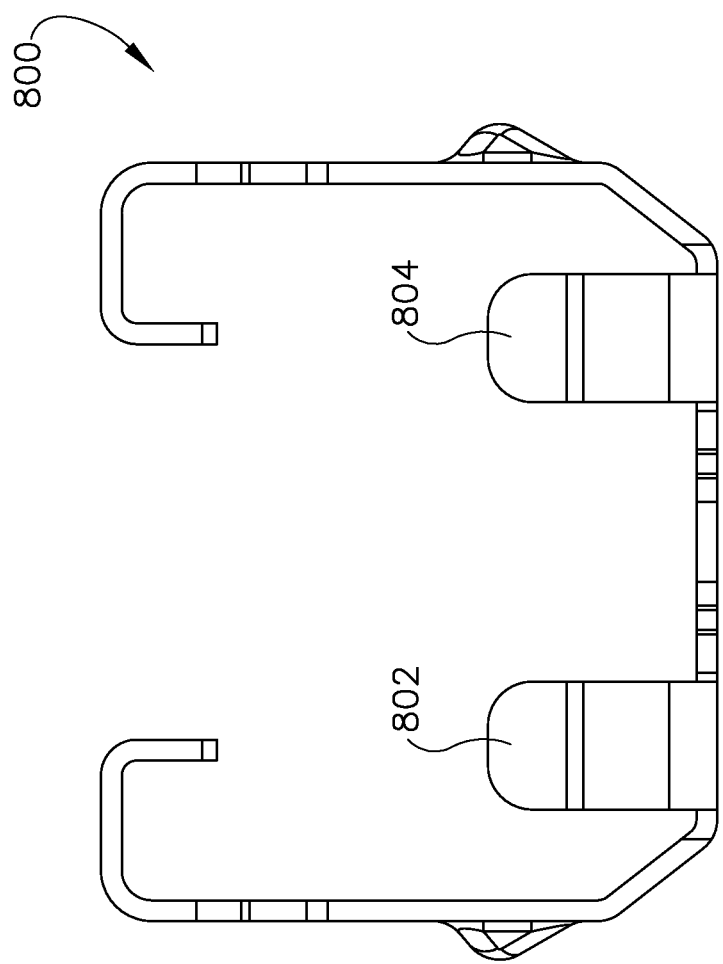
FIG. 72 depicts a rear view of the cartridge tray of FIG. 70.
Figure 73:
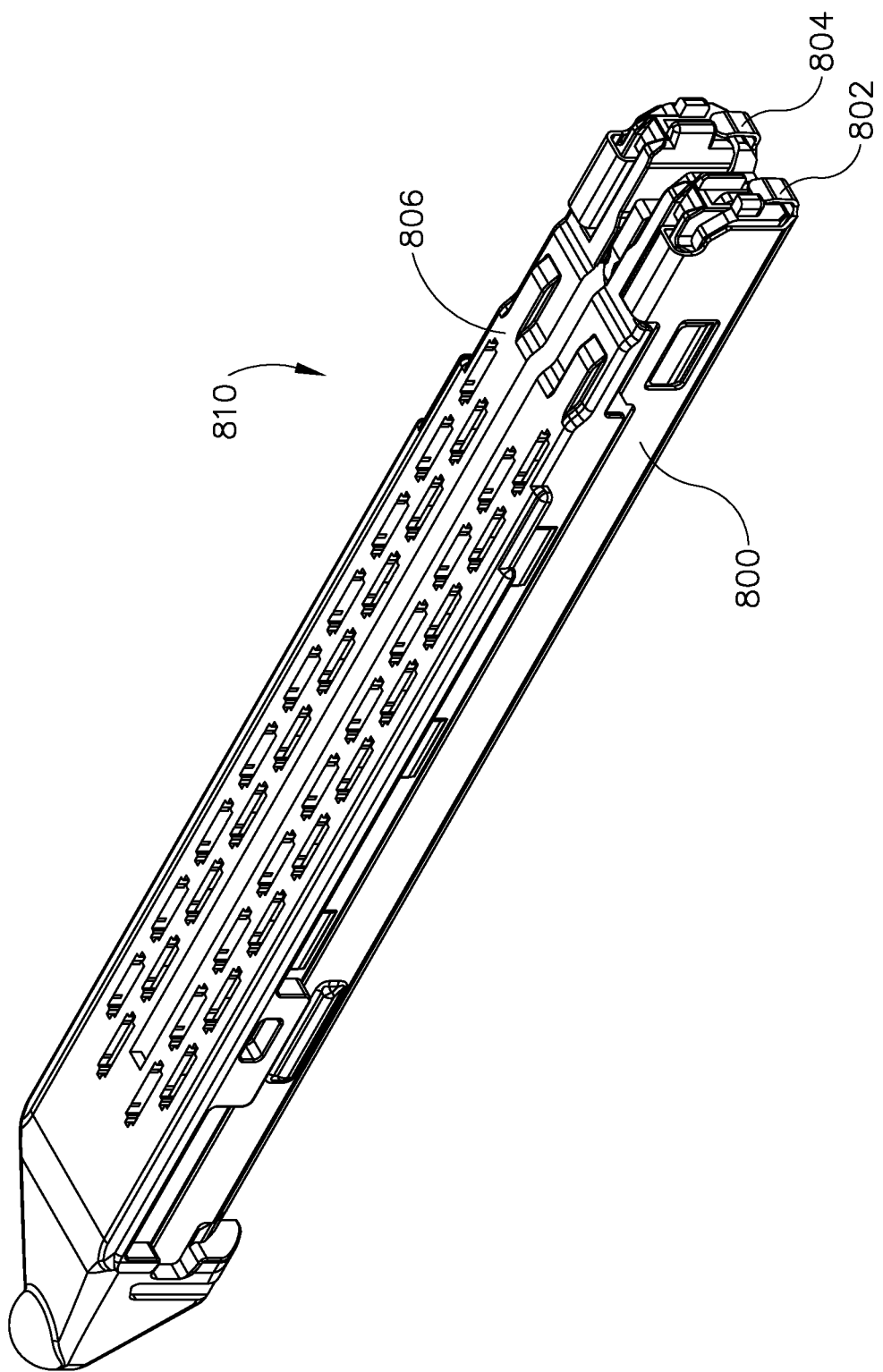
FIG. 73 depicts a perspective view of yet another exemplary cartridge having the cartridge tray of FIG. 70.
Figure 74:
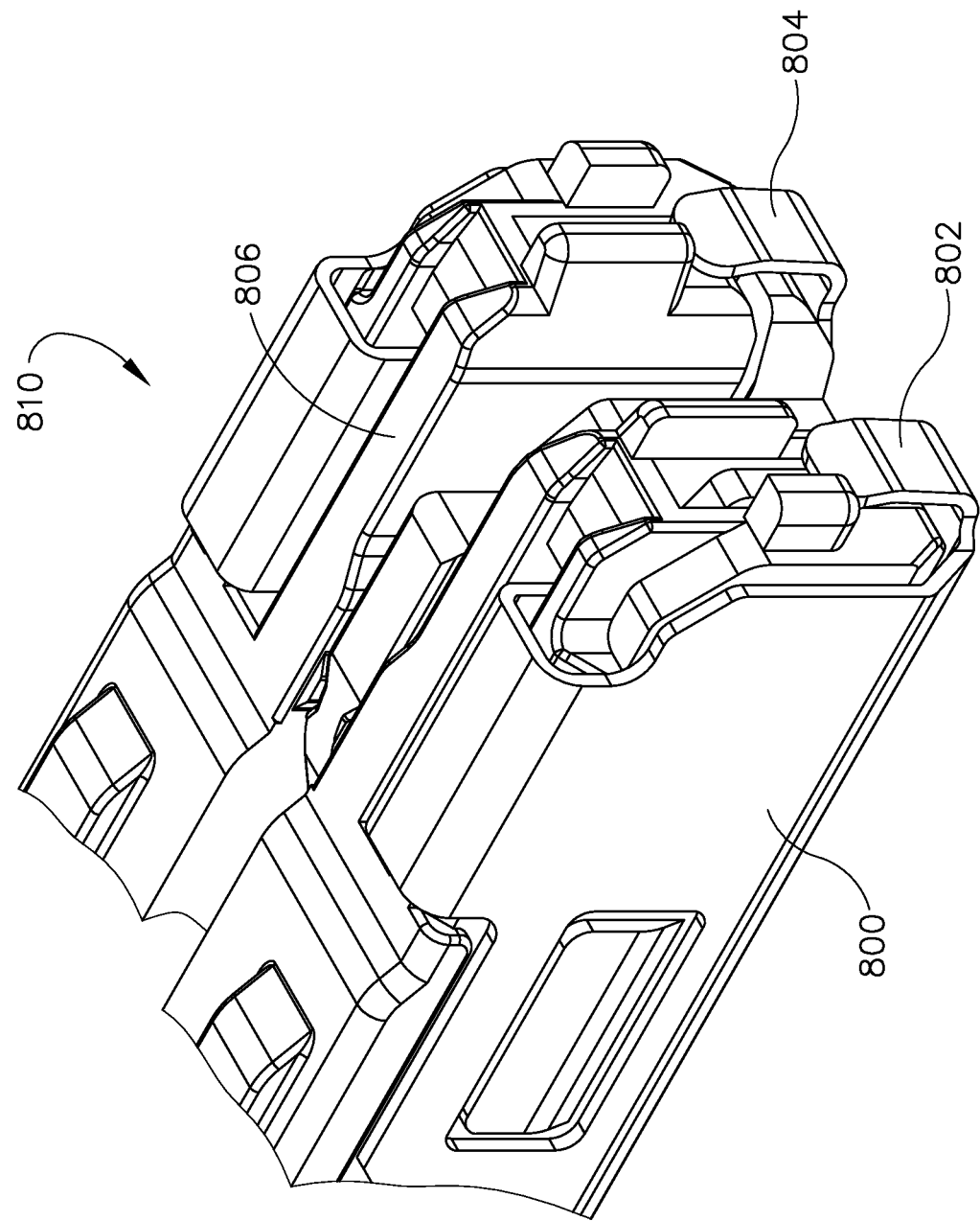
FIG. 74 depicts a perspective view of the proximal end of the cartridge of FIG. 73 having the cartridge tray of FIG. 70.
Figure 75:
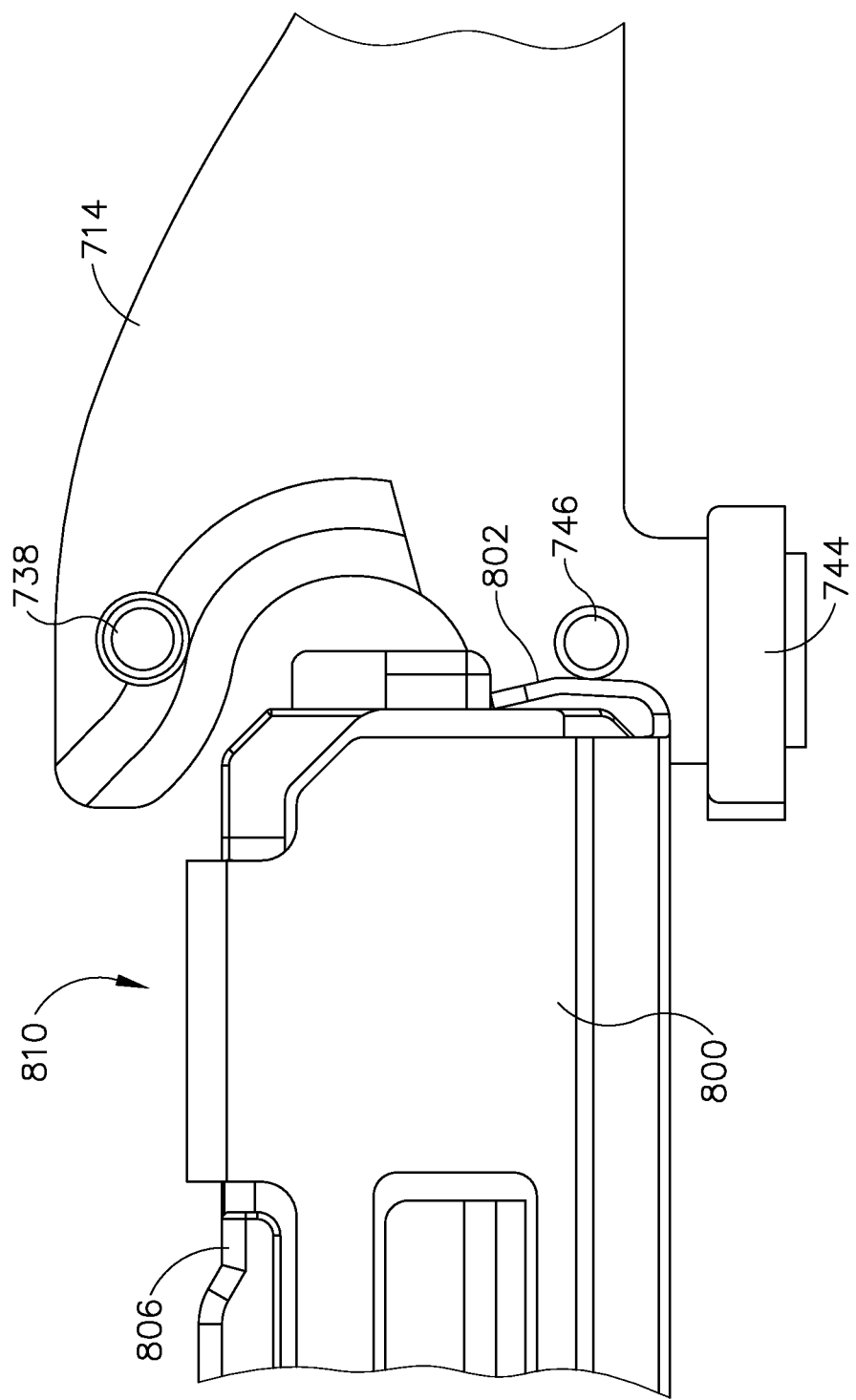
FIG. 75 depicts a side view of the firing bar of FIG. 61 contacting the proximal end of the cartridge tray of FIG. 70.

FIGS. 70-75 show an exemplary alternative cartridge tray (800) having lockout features. Cartridge tray (800) is incorporated into a staple cartridge (810) (FIG. 73) that is intended for use in end effector (40, 240) but not in end effector (740). Cartridge tray (800) of the present example is configured to operate substantially similar to cartridge trays (76, 276) discussed above except for the differences discussed below. As best seen in FIGS. 70-72, the lockout features of cartridge tray (800) of the present example comprise a pair of rigid tabs (802, 804) extending upwardly from a proximal end of a top surface of a base of cartridge tray (800). As shown in FIGS. 73 and 74, with a cartridge body (806) disposed within cartridge tray (800), tabs (802, 804) are positioned proximally of a proximal end of cartridge body (806). As shown in FIG. 75, tabs (802, 804) are configured to engage middle pin (746) so as to prevent distal firing of firing bar (714) in the event that cartridge (810) having cartridge tray (800) is inserted into lower jaw (716). Thus, tabs (802, 804) prevent cartridge (810) from being used in end effector (740). However, tabs (802, 804) do not prevent cartridge (810) from being used in end effectors (40, 240). End effectors (40, 240) include no moving components whose movement would be blocked by tabs (802, 804).

VI. EXEMPLARY ALTERNATIVE LOCKOUT FEATURES

FIGS. 76-80 show features of an exemplary alternative end effector (1000) that may be used in place of any of the end effectors (40, 240) described herein. End effector (1000) of this example comprises an anvil (1010), a staple cartridge (1012), a lower jaw (1020), and a knife member (1040). Anvil (1010) of this example is identical to anvils (60, 260) described above. Similarly, staple cartridge (1012) of this example is identical to staple cartridges (70, 270) described above. It should be understood that end effector (1000) may be readily incorporated into instrument (10) in place of end effector (40, 240).

Figure 76:
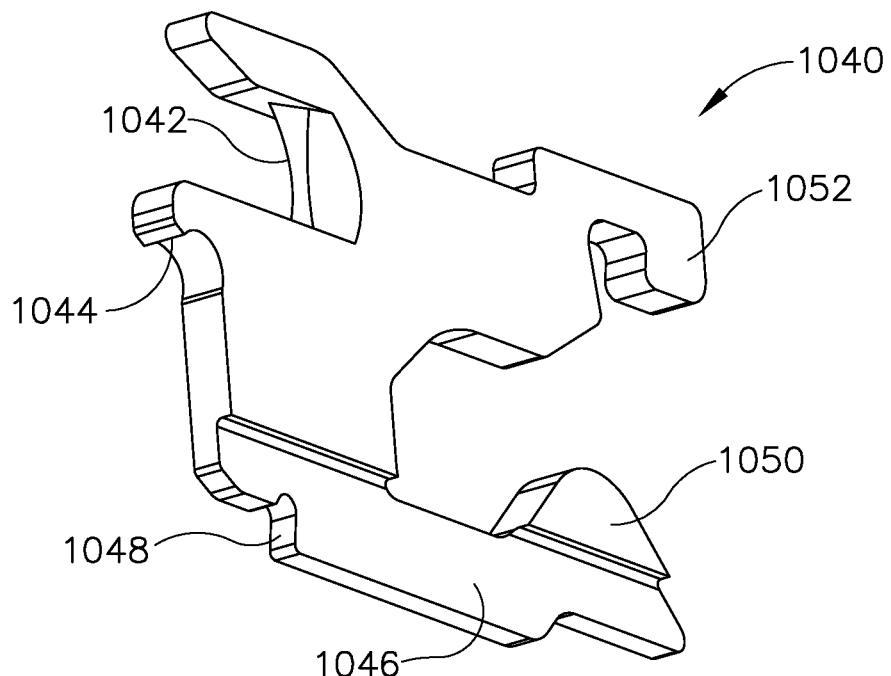
FIG. 76 depicts a perspective view of an exemplary alternative knife member that may be incorporated into an exemplary alternative end effector for the instrument of FIG. 1.
Figure 77:
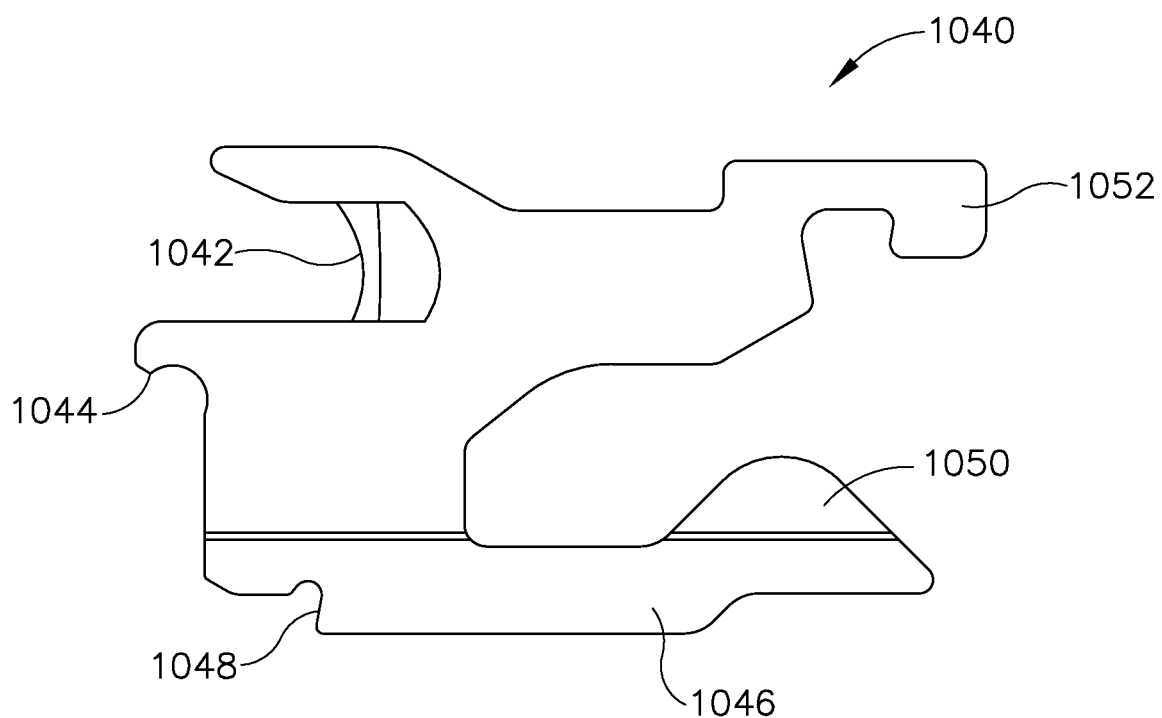
FIG. 77 depicts a side elevational view of the knife member of FIG. 76.
Figure 79:
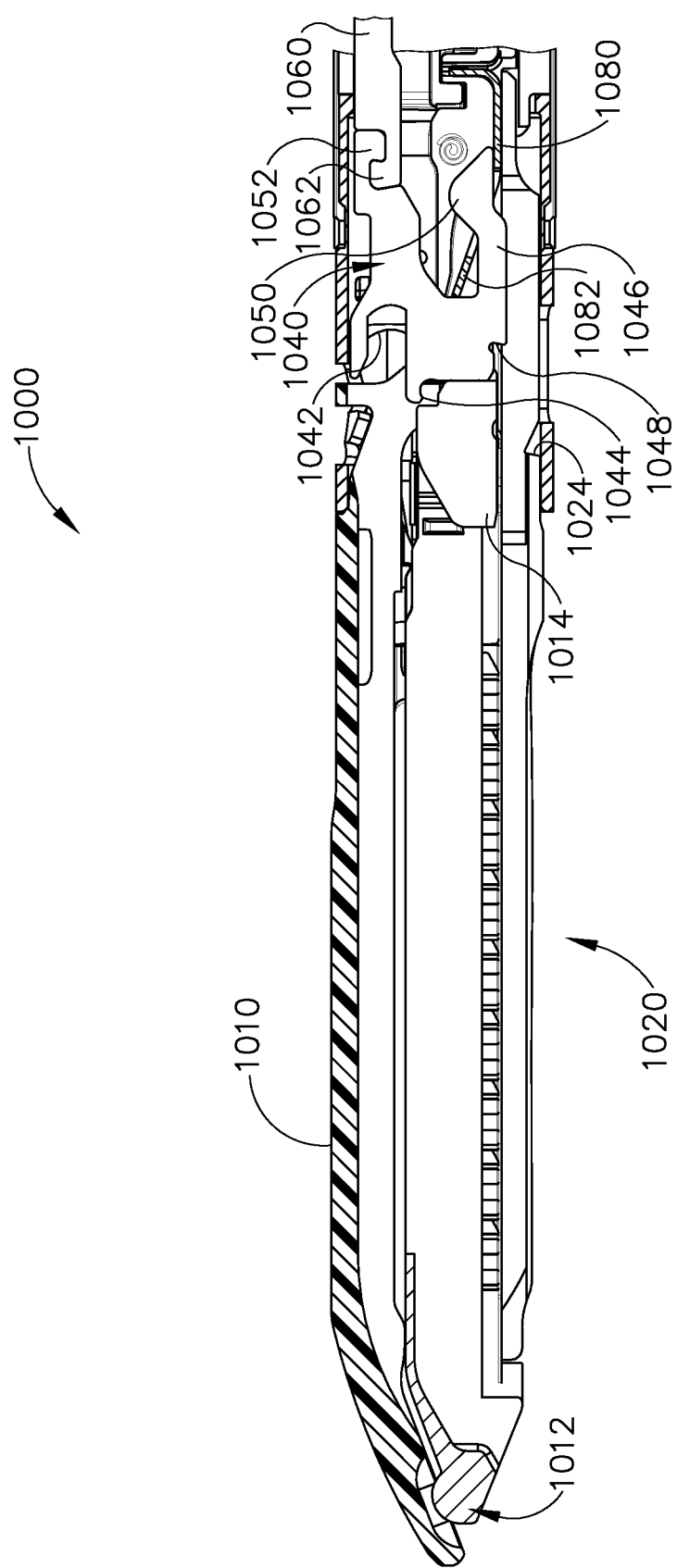
FIG. 79 depicts a cross-sectional side view of an exemplary alternative end effector incorporating the knife member of FIG. 76 and the lower jaw of FIG. 78, with the knife member in a proximal position.
Figure 80:
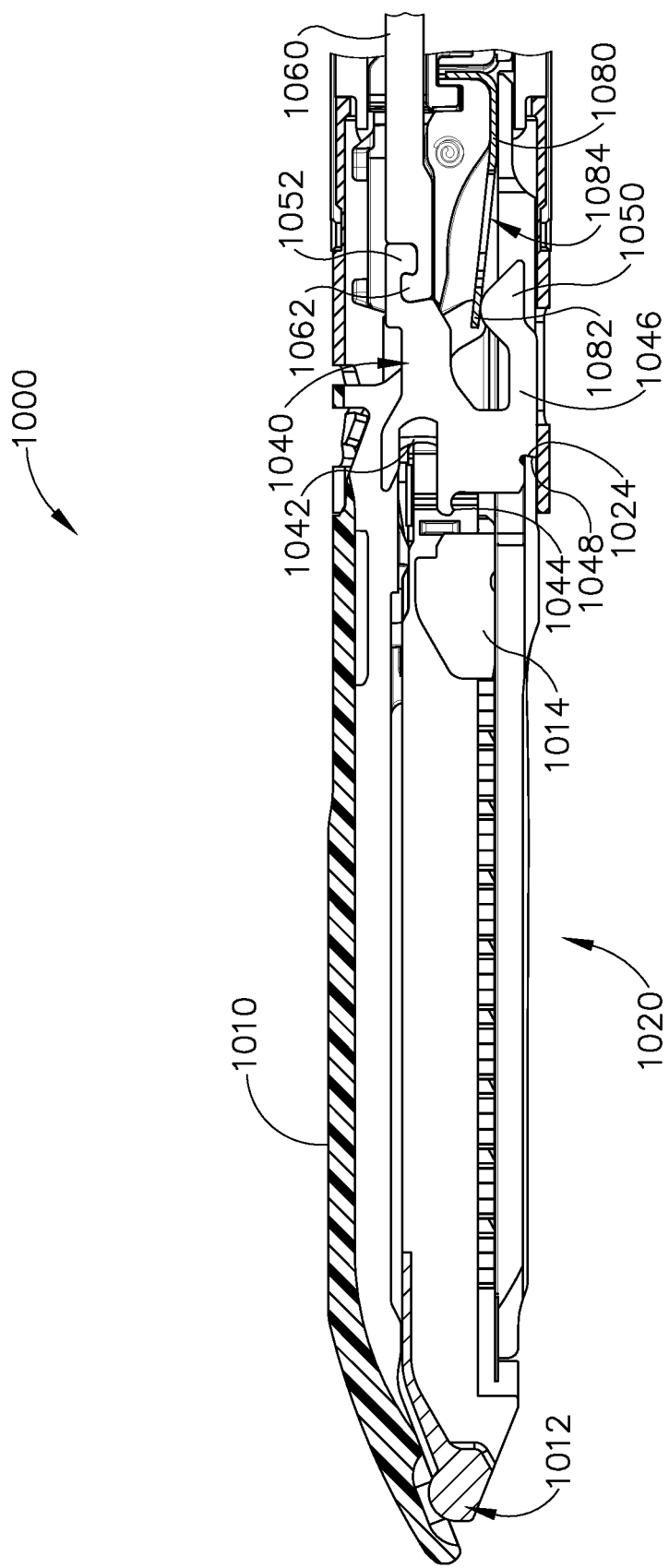
FIG. 80 depicts a cross-sectional side view of the end effector of FIG. 79, with the knife member in a locked out position.

As best seen in FIGS. 76-77, knife member (1040) of the present example is substantially identical to knife members (80, 280) described above, except for the differences described below. Knife member (1040) of this example includes a distal cutting edge (1042), a distal tip (1044), a downwardly extending protrusion (1046), and a firing beam engagement feature (1052). Protrusion (1046) includes a distally facing lockout surface (1048), which will be described in greater detail below. An upwardly extending tab (1050) is located at the proximal end of protrusion (1046). As best seen in FIGS. 79-80, firing beam engagement feature (1052) is configured to couple with a complementary engaging feature (1062) of a firing beam (1060). Such coupling may be secured using welding (e.g., spot welds, etc.), adhesives, and/or any other suitable techniques/features/etc. It should also be understood that the combination of firing beam (1060) and knife member (1040) may be translated distally and proximally using the same features and techniques described above with respect to firing beam (82, 282). Other suitable ways in which the combination of firing beam (1060) and knife member (1040) may be translated distally and proximally will be apparent to those of ordinary skill in the art in view of the teachings herein.

Figure 78:
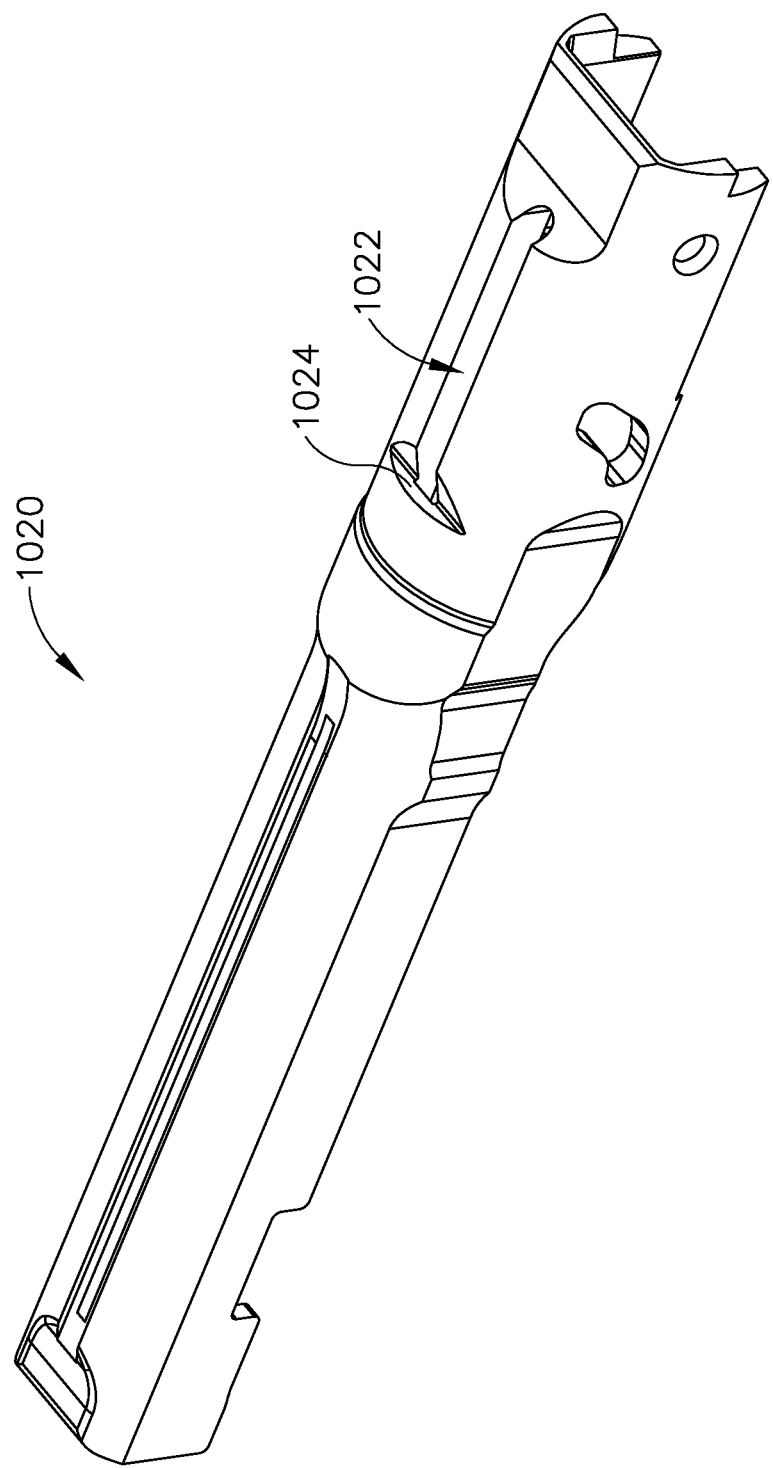
FIG. 78 depicts a perspective view showing the underside of an exemplary alternative lower jaw that may be combined with the knife member of FIG. 76 in an exemplary alternative end effector for the instrument of FIG. 1.

FIG. 78 shows lower jaw (1020) of the present example in greater detail. Lower jaw (1020) is substantially identical to lower jaws (50, 250) described above, except for the differences described below. Lower jaw (1020) is configured to removably receive staple cartridge (1012) as shown in FIGS. 79-80. Lower jaw (1020) is also pivotably coupled with anvil (1010), such that anvil (1010) is operable to pivot toward and away from the combination of staple cartridge (1012) and lower jaw (1020), as described in other examples above. Turning back to FIG. 78, lower jaw (1020) of this example includes a proximal slot (1022). The distal end of slot (1022) terminates at a proximally facing lockout surface (1024). As will be described in greater detail below, lockout surface (1048) of knife member (1040) is configured to engage lockout surface (1024) of lower jaw (1020) in order to provide a lockout condition when either staple cartridge (1012) has already been fired once or staple cartridge (1012) is missing.

FIG. 79 shows end effector (1000) in a ready to fire state. In particular, staple cartridge (1012) is loaded in lower jaw (1020), anvil (1010) is in a closed position, and knife member (1040) is in a proximal position. In this state, knife member (1040) is also in an upper position. Knife member (1040) is positioned such that a portion of knife member (1040) is disposed in an opening (1084) of a resilient member (1080). Resilient member (1080) of this example is identical to resilient member (210) described above. In this state, a distal end (1082) is positioned above protrusion (1046) and distal to tab (1050). Resilient member (1080) resiliently bears downwardly on knife member (1040) in this state. However, distal tip (1044) of knife member (1040) engages an upwardly facing surface at the proximal end of a sled (1014) in staple cartridge (1012). Sled (1014) thus cooperates with distal tip (1044) to provide support for knife member (1040), holding knife member (1040) in the upper position despite the downward bias imposed by resilient member (1080). It should be noted that lockout surface (1048) of knife member (1040) is located at a vertical position that is higher than the vertical position of lockout surface (1024) in this state. Sled (1014) of this example is substantially identical to sleds (78, 278) described above.

As firing beam (1060) and knife member (1040) are advanced distally from the position shown in FIG. 79 to actuate end effector (1000), driving staples from staple cartridge (1012) into tissue and severing the tissue with edge (1042), sled (1014) continues to cooperate with distal tip (1044) to provide support for knife member (1040). Knife member (1040) thus maintains the vertical positioning shown in FIG. 79 as knife member (1040) translates from a proximal position to a distal position. It should therefore be understood that lockout surface (1048) of knife member (1040) passes over lockout surface (1024) of lower jaw (1020), such that lockout surface (1048) does not engage lockout surface (1024) during the distal translation of knife member (1040) when sled (1014) provides support for knife member (1040). It should also be understood that, in the present example, sled (1014) will only provide support for knife member (1040) when cartridge (1012) has been properly loaded in lower jaw (1020) and cartridge (1012) has not yet been fired.

In the event that cartridge (1012) is not loaded in lower jaw (1020), lockout surface (1048) of knife member (1040) will engage lockout surface (1024) of lower jaw (1020), thereby effectively locking knife member (1040) by preventing further distal translation of knife member (1040). Similarly, in the event that an operator attempts to drive knife member (1040) distally after cartridge (1012) has been fired (or even partially fired), lockout surface (1048) of knife member (1040) will engage lockout surface (1024) of lower jaw (1020), thereby effectively locking knife member (1040) by preventing further distal translation of knife member (1040). For instance, FIG. 80 shows end effector (1000) in a state where sled (1014) is positioned distally in relation to the position of sled (1014) in FIG. 79. Sled (1014) is thus spaced away from distal tip (1044), such that sled (1014) will not provide support for knife member (1040). Without the support of sled (1014), resilient member (1080) drives knife member (1040) downwardly as knife member (1040) is advanced distally. This causes lockout surface (1048) of knife member (1040) to engage lockout surface (1024) of lower jaw (1020), as shown in FIG. 80. With surfaces (1048, 1024) so engaged, knife member (1040) may not be translated any further distally.

If the operator subsequently retracts knife member (1040) proximally from the position shown in FIG. 80, a camming feature in end effector (1000) may drive knife member (1040) upwardly, such that knife member (1040) and resilient member (1080) return to the positions shown in FIG. 79. This may enable the operator to load an unfired staple cartridge (1012) in end effector (1000) and actuate end effector (1000) properly.

It should be understood from the foregoing that the lockout features of lower jaw (1020) and knife member (1040) may serve as a substitute for the lockout features of frame member (238) and knife member (280) described above. It should also be understood that the various kinds of lockout bypass features described above with reference to FIGS. 26-58 may also be readily incorporated into or otherwise combined with end effector (1000). Various suitable ways in which end effector (1000) may be combined with other teachings herein will be apparent to those of ordinary skill in the art.

VII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims. It should also be understood that the various teachings herein may be readily combined with the teachings of the various references that are cited herein. In addition, the various teachings herein may be readily combined with the teachings of U.S. patent application Ser. No. 14/314,108, filed Jun. 25, 2014, published as U.S. Patent Pub. No. 2015/0374373 on Dec. 31, 2015, issued as U.S. Pat. No. 10,335,147 on Jul. 2, 2019, entitled "Method of Using Lockout Features for Surgical Stapler Cartridge," filed on even date herewith, the disclosure of which is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/

0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012 now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple cartridge for use with a surgical stapling instrument, comprising:
   (a) a body;
   (b) a deck configured to engage tissue, wherein the deck includes a plurality of openings configured to house a plurality of staples, wherein the staple cartridge is operable to eject the staples into tissue engaged by the deck;
   (c) a channel extending longitudinally through the body and the deck, wherein the channel is configured to slidably receive a knife member operable to translate distally through the channel to cut the tissue engaged by the deck; and
   (d) a lockout feature disposed within the channel and confined to a region between the deck and a floor of the channel, wherein the lockout feature is movably coupled to a sidewall of the channel,
   wherein the lockout feature is movable relative to the sidewall between a first position in which the lockout feature is configured to permit distal translation of the knife member through the channel, and a second position in which the lockout feature is configured to promote hindrance of distal translation of the knife member through the channel,
   wherein the lockout feature is configured to assume and maintain the second position after the knife member is advanced distally through the channel.

2. The staple cartridge of claim 1, wherein the lockout feature is pivotably coupled to the sidewall of the channel.

3. The staple cartridge of claim 2, wherein the lockout feature is pivotably coupled to the sidewall with a living hinge.

4. The staple cartridge of claim 1, wherein the lockout feature is disposed below the deck and distal to a proximal-most end of the body.

5. The staple cartridge of claim 1, further comprising a recess arranged in a sidewall of the channel, wherein the lockout feature extends outwardly from the recess in one of the first position or the second position, wherein the lockout feature is at least partially retracted within the recess in the other of the first position or the second position.

6. The staple cartridge of claim 1, further comprising a sled member, wherein the sled member is operable to translate distally through the body to drive staples from the openings and into tissue engaged by the deck, wherein the lockout feature is configured to assume and maintain the second position when the sled member is disposed at a distal end of the channel while the knife member is disposed at a proximal end of the channel.

7. The staple cartridge of claim 1, wherein the lockout feature comprises a tab.

8. The staple cartridge of claim 7, wherein the tab is pivotably coupled to the sidewall of the channel and is configured to pivot between the first position and the second position.

9. The staple cartridge of claim 1, wherein the lockout feature is configured to extend into the channel in the second position.

10. The staple cartridge of claim 1, wherein the lockout feature is biased toward the second position.

11. The staple cartridge of claim 1, wherein in the first position the lockout feature is oriented in non-contact relation with a distal feature of the knife member, wherein in the second position the lockout feature is oriented to contact the distal feature.

12. The staple cartridge of claim 1, wherein in the first position the lockout feature is oriented to contact a distal feature of the knife member, wherein in the second position the lockout feature is oriented in non-contact relation with the distal feature.

13. The staple cartridge of claim 1, wherein the lockout feature comprises a pair of tabs pivotably coupled to opposed sidewalls of the channel.

14. The staple cartridge of claim 13, wherein the tabs are movably coupled to the sidewalls such that the tabs extend toward one another within the channel when the lockout feature is in the first position, wherein the tabs are configured to pivot away from one another in response to distal translation of the knife member through the channel.

15. A staple cartridge for use with a surgical stapling instrument, comprising:
(a) a body;
(b) a deck configured to engage tissue, wherein the deck includes a plurality of openings configured to house a plurality of staples, wherein the staple cartridge is operable to eject the staples into tissue engaged by the deck;
(c) a channel extending longitudinally through the body and the deck, wherein the channel is configured to slidably receive a knife member operable to translate distally through the channel to cut the tissue engaged by the deck;
(d) a recess arranged in a sidewall of the channel at a location between the deck and a floor of the channel such that the recess opens transversely to the channel; and
(e) a lockout feature movably disposed within the channel,
wherein the lockout feature is movable relative to the sidewall between an exposed position in which the lockout feature extends outwardly from the recess and into the channel, and an unexposed position in which the lockout feature is at least partially retracted within the recess,
wherein in the exposed position the lockout feature is oriented to contact a distal feature of the knife member,
wherein in the unexposed position the lockout feature is oriented in non-contact relation with the distal feature of the knife member.

16. The staple cartridge of claim 15, wherein the lockout feature is configured to permit distal translation of the knife member through the channel when in one of the exposed position or the unexposed position, wherein the lockout feature is further configured to promote hindrance of distal translation of the knife member through the channel when in the other of the exposed position or the unexposed position.

17. The staple cartridge of claim 15, wherein the lockout feature comprises a tab pivotably coupled with the sidewall of the channel.

18. A surgical stapling instrument comprising:
(a) an instrument body;
(b) a shaft assembly extending distally from the instrument body; and
(c) an end effector at a distal end of the shaft assembly, wherein the shaft assembly comprises:
(i) a first jaw,
(ii) a second jaw, wherein the first and second jaws are configured to clamp tissue therebetween,
(iii) a knife member configured to translate along a longitudinal axis of the end effector to cut the clamped, and
(iv) a staple cartridge coupled with one of the first jaw or the second jaw, wherein the staple cartridge comprises:
(A) a cartridge body,
(B) a deck configured to engage the clamped tissue, wherein the deck includes a plurality of openings configured to house a plurality of staples, wherein the end effector is operable to eject the staples into the clamped tissue,
(C) a channel extending longitudinally through the cartridge body and the deck, wherein the knife member is configured to translate distally through the channel to cut the clamped tissue, and
(D) a tab disposed within the channel and pivotably coupled to a sidewall of the channel, wherein the tab is confined to a region between the deck and a floor of the channel,
wherein the tab is pivotable between a first position in which the tab is configured to permit distal translation of the knife member through the channel, and a second position in which the tab is configured to promote hindrance of distal translation of the knife member through the channel.

19. The surgical stapling instrument of claim 18, wherein the tab is pivotably coupled to a sidewall of the channel.

20. The surgical stapling instrument of claim 18, wherein the tab is configured to extend parallel to the sidewall of the channel when in one of the first position or the second position, wherein the tab is configured to extend transversely across at least a portion of the channel in the other of the first position or the second position.

* * * * *